(12) United States Patent
Cave

(10) Patent No.: US 10,629,307 B2
(45) Date of Patent: *Apr. 21, 2020

(54) METHOD, SYSTEM, AND COMPUTER PROGRAM PRODUCT FOR PHYSICIAN EFFICIENCY MEASUREMENT AND PATIENT HEALTH RISK STRATIFICATION

(71) Applicant: CAVE CONSULTING GROUP, INC., San Mateo, CA (US)

(72) Inventor: Douglas G. Cave, San Mateo, CA (US)

(73) Assignee: Cave Consulting Group, Inc., San Mateo, CA (US)

( * ) Notice: Subject to any disclaimer, the term of this patent is extended or adjusted under 35 U.S.C. 154(b) by 231 days.

This patent is subject to a terminal disclaimer.

(21) Appl. No.: 15/882,844

(22) Filed: Jan. 29, 2018

(65) Prior Publication Data

US 2019/0051404 A1 Feb. 14, 2019

Related U.S. Application Data

(63) Continuation of application No. 14/269,084, filed on May 3, 2014, now Pat. No. 9,881,129, which is a
(Continued)

(51) Int. Cl.
*G16H 50/30* (2018.01)
*G16H 40/20* (2018.01)
(Continued)

(52) U.S. Cl.
CPC ............. *G16H 50/30* (2018.01); *G06F 19/00* (2013.01); *G06Q 10/06398* (2013.01);
(Continued)

(58) Field of Classification Search
CPC ........ G06Q 50/22; G06Q 30/02; G06Q 40/08; G06Q 10/10; G06Q 10/06398;
(Continued)

(56) References Cited

U.S. PATENT DOCUMENTS 3,566,365 A 2/1971 Rawson et al.
3,697,957 A 10/1972 Barron
(Continued)

FOREIGN PATENT DOCUMENTS

WO 199512857 A1 5/1995

OTHER PUBLICATIONS

Chilingerian, "Evaluating Physician Efficiency in Hospitals: A Multivariate Analysis of Best Practices", European Journal of Operational Research, vol. 80, Issue 3, Feb. 2, 1995, pp. 548-574 (Year: 1995).*
(Continued)

*Primary Examiner* — Joy Chng
(74) *Attorney, Agent, or Firm* — Armstrong Teasdale LLP

(57) ABSTRACT

A method for measuring physician efficiency and patient health risk stratification is disclosed. Episodes of care are formed from medical claims data and an output process is performed. Physicians are assigned to report groups, and eligible physicians and episode assignments are determined. Condition-specific episode statistics and weighted episode statistics are calculated, from which physician efficiency scores are determined.

21 Claims, 6 Drawing Sheets

Related U.S. Application Data continuation of application No. 13/794,765, filed on Mar. 11, 2013, now Pat. No. 8,768,726, which is a continuation of application No. 13/621,234, filed on Sep. 15, 2012, now Pat. No. 8,639,528, which is a continuation of application No. 13/012,219, filed on Jan. 24, 2011, now Pat. No. 8,340,981, which is a continuation-in-part of application No. 12/769,090, filed on Apr. 28, 2010, now abandoned, which is a continuation of application No. 10/794,216, filed on Mar. 5, 2004, now Pat. No. 7,739,126.

(60) Provisional application No. 60/549,601, filed on Mar. 2, 2004.

(51) Int. Cl.
| | | |
|---|---|---|
| *G06Q 10/10* | (2012.01) | |
| *G06Q 50/22* | (2018.01) | |
| *G16Z 99/00* | (2019.01) | |
| *G06Q 30/02* | (2012.01) | |
| *G06Q 10/06* | (2012.01) | |
| *G06F 19/00* | (2018.01) | |

(52) U.S. Cl.
CPC ............ *G06Q 10/10* (2013.01); *G06Q 30/02* (2013.01); *G06Q 50/22* (2013.01); *G16H 40/20* (2018.01); *G16Z 99/00* (2019.02); *A61B 2505/05* (2013.01)

(58) Field of Classification Search
CPC ....... G06F 19/327; G06F 19/00; G16H 50/30; G16H 40/20; G16Z 99/00
USPC .......................................................... 705/2–3
See application file for complete search history.

(56) References Cited

U.S. PATENT DOCUMENTS

| | | |
|---|---|---|
| 3,716,840 A | 2/1973 | Masten et al. |
| 4,286,330 A | 8/1981 | Isaacson |
| 4,290,114 A | 9/1981 | Sinay |
| 4,315,309 A | 2/1982 | Coli |
| 4,319,225 A | 3/1982 | Klose |
| 4,326,259 A | 4/1982 | Cooper et al. |
| 4,328,491 A | 5/1982 | Demetrescu et al. |
| 4,360,875 A | 11/1982 | Behnke |
| 4,368,059 A | 1/1983 | Doerges et al. |
| 4,435,769 A | 3/1984 | Nagano et al. |
| 4,454,414 A | 6/1984 | Benton |
| 4,479,176 A | 10/1984 | Grimshaw |
| 4,489,387 A | 12/1984 | Lamb et al. |
| 4,491,725 A | 1/1985 | Pritchard |
| 4,553,206 A | 11/1985 | Smutek et al. |
| 4,632,428 A | 12/1986 | Brown |
| 4,648,037 A | 3/1987 | Valentino |
| 4,658,370 A | 4/1987 | Erman et al. |
| 4,667,292 A | 5/1987 | Mohlenbrock et al. |
| 4,700,297 A | 10/1987 | Hagel, Sr. et al. |
| 4,731,725 A | 3/1988 | Suto et al. |
| 4,733,354 A | 3/1988 | Potter et al. |
| 4,803,641 A | 2/1989 | Hardy et al. |
| 4,858,121 A | 8/1989 | Barber et al. |
| 4,866,634 A | 9/1989 | Reboh et al. |
| 4,872,122 A | 10/1989 | Altschuler et al. |
| 4,878,175 A | 10/1989 | Norden-Paul et al. |
| 4,916,633 A | 4/1990 | Tychonievich et al. |
| 4,937,743 A | 6/1990 | Rassman et al. |
| 4,945,476 A | 7/1990 | Bodick et al. |
| 4,975,840 A | 12/1990 | De Tore et al. |
| 4,987,538 A | 1/1991 | Johnson et al. |
| 5,001,630 A | 3/1991 | Willfong |
| 5,018,067 A | 5/1991 | Mohlenbrock et al. |
| 5,065,315 A | 11/1991 | Garcia |
| 5,070,452 A | 12/1991 | Doyle, Jr. et al. |
| 5,072,383 A | 12/1991 | Brimm et al. |
| 5,099,424 A | 3/1992 | Schneiderman |
| 5,225,976 A | 7/1993 | Tawil |
| 5,235,702 A | 8/1993 | Miller |
| 5,253,164 A | 10/1993 | Holloway et al. |
| 5,255,187 A | 10/1993 | Sorensen |
| 5,301,105 A | 4/1994 | Cummings, Jr. |
| 5,307,262 A | 4/1994 | Ertel |
| 5,319,543 A | 6/1994 | Wilhelm |
| 5,324,077 A | 6/1994 | Kessler et al. |
| 5,325,293 A | 6/1994 | Dome |
| 5,359,509 A | 10/1994 | Little et al. |
| 5,365,425 A | 11/1994 | Torma et al. |
| 5,392,209 A | 2/1995 | Eason et al. |
| 5,404,292 A | 4/1995 | Hendrickson |
| 5,467,268 A | 11/1995 | Sisley |
| 5,471,382 A | 11/1995 | Tallman et al. |
| 5,483,443 A | 1/1996 | Milstein et al. |
| 5,486,999 A | 1/1996 | Mebane |
| 5,508,912 A | 4/1996 | Schneiderman |
| 5,517,405 A | 5/1996 | McAndrew et al. |
| 5,519,607 A | 5/1996 | Tawil |
| 5,521,814 A | 5/1996 | Teran et al. |
| 5,544,044 A | 8/1996 | Leatherman |
| 5,557,514 A * | 9/1996 | Seare ..................... G06Q 40/02 705/2 |
| 5,577,169 A | 11/1996 | Prezioso |
| 5,583,758 A | 12/1996 | McIlroy et al. |
| 5,594,637 A | 1/1997 | Eisenberg et al. |
| 5,613,072 A | 3/1997 | Hammond et al. |
| 5,644,778 A | 7/1997 | Burks et al. |
| 5,652,842 A | 7/1997 | Siegrist, Jr. et al. |
| 5,660,183 A | 8/1997 | Chiang et al. |
| 5,664,207 A | 9/1997 | Crumpler et al. |
| 5,706,441 A | 1/1998 | Lockwood |
| 5,724,379 A | 3/1998 | Perkins et al. |
| 5,819,228 A | 10/1998 | Spiro |
| 5,826,237 A | 10/1998 | Macrae et al. |
| 5,835,897 A | 10/1998 | Dang |
| 5,845,253 A | 12/1998 | Rensimer et al. |
| 5,855,395 A | 1/1999 | Foote et al. |
| 5,891,228 A | 4/1999 | Baker et al. |
| 5,909,669 A * | 6/1999 | Havens .................. G06Q 30/02 705/7.42 |
| 5,918,208 A | 6/1999 | Javitt |
| 5,970,463 A | 10/1999 | Cave et al. |
| 6,061,657 A | 5/2000 | Whiting-O'Keefe |
| 6,182,047 B1 | 1/2001 | Dirbas |
| 6,223,164 B1 | 4/2001 | Seare et al. |
| 7,222,079 B1 | 5/2007 | Seare et al. |
| 7,389,245 B1 * | 6/2008 | Ashford ................. G06Q 30/02 705/2 |
| 7,546,245 B2 | 6/2009 | Surpin et al. |
| 7,617,115 B2 * | 11/2009 | McNair .................. G06Q 50/22 705/3 |
| 7,739,126 B1 | 6/2010 | Cave et al. |
| 2004/0111291 A1 * | 6/2004 | Dust ..................... G06F 19/328 705/2 |

OTHER PUBLICATIONS

Anderson, S. et al., "The Gatekeeper Effect on Managing Acute Medical Conditions," Medical Interlace, Sep. 1996, pp. 122-129.
Bronskill, S. et al, "Longitudinal profiles of health care providers," Statistics in Medicine, 2002 (no month), pp. 1067-1088, vol. 21.
Cave, D., "Analyzing the content of physicians' medical practices,", Ambulatory Care Manage, Jul. 1994, pp. 15-36, vol. 17, No. 3.
Cave, D. et al., "Analyzing Patterns-of-Treatment Data to Provide Feedback to Physicians," Medical Interlace, Jul. 1994, pp. 117-128.
Cave, D. et al "Case Study: Integrating medical & drug claims data," Pharmacare Economics, Oct. 1996, pp. 30-32 and 36-38.
Cave, D., "Controlling Increases in the Volume and Intensity of Medical Services," International Foundation of Employee Benefit Plans, Brooksfield, WI., Jun. 1993, pp. 11-18.
Cave, D., "Evaluating Health Plan Efficiency", Compensation & Benefits Management, Summer 1992, vol. 8, No. 3.

(56) References Cited

OTHER PUBLICATIONS

Cave, D., "Pattern-of-Treatment Differences Among Primary Care Physicians in Alternative Systems of Care," Benefits Quarterly, Third Quarter 1994, pp. 6-19.
Cave, D. et al., "Pitney Bowes: Using comprehensive Cost Information to Build Provider Networks," Benefits Quarterly, Second Quarter 1995, pp. 19-25.
Cave, D., "Profiling Physician Practice Patterns Using Diagnostic Episode Clusters," Medical Care, May 1995, pp. 463-486, vol. 33, No. 5.
Cave, D., "Small-Area Variations in the treatment of prevalent medical conditions: a comparison of three cities in the Northeast," I of Ambulatory Care Manage, Jul. 1995, pp. 42-57, vol. 18, No. 3.
Cave D., "Today's Managed Care Market," Compensation & Benefits Management, Summer 1994, 6 pages.
Cave D., "Using Diagnostic Clusters to Evaluate Patterns of Treatment and Develop Capitation Rates," Employee Benefits Journal, Mar. 1995, pp. 24-30.
Cave, D. et al., Who Treats Medical Conditions More Cost Efficiently? Medical Interlace, May 1994, pp. 136-142.
Cave Consulting Group, "Cave Consulting Group—Efficiency Measurement Errors, Practice Patterns, Treatment Patterns, Efficiency, Health Care Costs, Quality of Care, Medical Guidelines", http://web.archive.org/web/20030217225948/http://www.cavegroup.com/efficiency_measurement_errors.html.
Chilingerian, J., "Evaluating physician efficiency in hospitals: A multivariate analyss of best practices," European Journal of Operational Research, 1995 (no month), pp. 548-574, vol. 80.
Cowen, M. et al., "Casemix Adjustment of Managed Care Claims Data Using the Clinical Classification for Health Policy Research Method," Medical Care, 1998 (no month), pp. 1108-1113, vol. 36, Na 7.
Fetter, R. et al., "Ambulatory Visit Groups: A Framework for Measuring Productivity in Ambulatory Care," Health Services Research, Oct. 1984, pp. 415-437, vol. 19, Na 4.
Fisher, E et al., "The Implications of Regional Variations in Medicare Spending. Part 1: The Content, Quality, and Accessibility of Care, Annals of Internal Medicine," Feb. 28, 2003, pp. 273-287, E288-E31 1, vol. 138, Na 4.
Beckman, F. et al., "Current Approaches to Improving the Value of Care: A Physician's Perspective," The Commonwealth Fund, Nov. 2007, 46 pages.
Fisher, E. et al., "The Implications of Regional Variations in Medicare Spending. Part 2: Health Outcomes and Satisfaction with Care, Annals of Internal Medicine," Feb. 28, 2003, pp. 288-298, E299-E322, vol. 138, Na 4.
Garnick, D. et al "Services and Charges by PPO Physicians for PPO and Indemnity Patients: An Episode of Care Comparison," Medical Care, Oct. 1990, pp. 894-906, vol. 28, Na 10.
Greene, R. et al., "Beyond the Efficiency Index: Finding a Better Way to Reduce Overuse and Increase Efficiency in Physician Care," DataWatch, May 20, 2008, pp. 250-25W.
Green, R. et al "Increasing Adherence to a Community-Based Guideline for Acute Sinusitis through Education, Physician Profiling, and Financial Incentives," American Journal of Managed Care, Oct. 2004, pp. 670-678, vol. 10, No. 10.
Guadagnoli, E., "Variation in the Use of Cardiac Procedures After Acute Myocardial Infarction," NEJM Aug. 31, 1995, pp. 573-578, vol. 333, No. W.
Hofer, T. et al ., "The Unreliability of Individual Physician "Report Cards" for Assessing the Costs and Quality of Care of a Chronic Disease," JAMA, Jun. 9, 1999, pp. 2098-2105, vol. 281, No. 22.
Hornbrook, M. et al., "Health Care Episodes: Definition, Measurement, and Use," Medical Care Review, Fall 1985, pp. 163-218, vol. 42, No. 2.
Hurwicz, M. et al "Care Seeking for Musculoskeletal and Respiratory Episodes in a Medicare Population," Medical Care, Nov. 1991, pp. 1130-1 145, vol. 29, No. 11.
Kessler, L. et al, "Episodes of Psychiatric Utilization", Medical Care, Dec. 1980, p. 1219-1 227, vol. XVIII, No. 1 2.

Ko, D. et al., "Regional Differences in Process of Care and Outcomes for Older Acute Myocardial Infarction Patients in the United States and Ontario, Canada," Journal of the American Heart Association, Circulation 2007: pp. 196-203, vol. 115.
Iezzoni, L. et al .,"A Description and Clinical Assessment of the Computerized Severity Index", QRB, Feb. 1992, pp. 44-52.
Miller, M. et al., "Physician Charges in the Hospital: Exploring Episodes of Care for Controlling Volume Growth", Medical Care, Jul. 1992, pp. 630-645, vol. 30, Na T.
Moscovice, I., "A Method for Analyzing Resource Use in Ambulatory Care Settings", Medical Care, Dec. 1977, pp. 1024-1044, vol. XV, Na 12.
Mullan, F., "Wrestling with Variation: An Interview with Jack Wennberg," Health Affairs—Web exclusive, pp. 73-80, Oct. 7, 2004.
Nickerson, C. et al., "A Methodology for Choosing a Physician Profiling System: The Case of First Option Health Plan", Journal of Health Care Finance, Winter 1999, pp. 5-12, vol. 26, No. 2.
Salkever, D. et al., "Episode-Based Efficiency Comparisons for Physicians and Nurse Practitioners", Medical Care, Feb. 1982, pp. 143-1 53, vol. XX, Na Z.
Schneewiss, R., et al ., "Diagnosis Clusters Adapted for ICD-9-CM and ICHPPC-2", The Journal of Family Practice, 1986 (no month), pp. 69-72, vol. 22, Not.
Coughlin, S. et al., "Measurement of Healthcare Quality and Efficiency: Resources for Healthcare Professionals," Society of Actuaries, Oct. 2009, 39 pages.
Schneewiss, R., et al ., "Diagnosis Clusters: A New Tool for Analyzing the Content of Ambulatory Medical Care", Medical Care, Jan. 1983, pp. 105-122, vol. XXI, Na t.
Thomas, J. et al, "Identifying "Practice Efficiency" Outliers Among Primary Care Physicians: Effects of Risk Adjustment Methodology and Practice Efficiency Metric", Report to the Robert Woods Johnson Foundation Health Care Financing and Organization (HCFO) Program, HFCO Grant # 36874, Blue Cross Blue Shield of Michigan Foundation Grant#243-11199, Mar. 18,2003,23 pages.
Weiner, J. et al., "Development and Application of a Population-Oriented Measure of Ambulatory Care Case-Mix," Medical Care, May 1991, pp. 452-472, vol. 29, Na 5.
Weinstein, J. et al., "United States' Trends and Regional Variations in Lumbar Spine Surgery: 1992-2003," Spine, Nov. 23, 2006, pp. 2707-2714, vol. 31, Na 21.
Welch, W. et al .,"Geographic Variation in Expenditures for Physicians' Services in the United States," The New England Journal of Medicine, Mar. 4, 1993, pp. 621-627, vol. 328, Na 9.
Wennberg, J., Unwarranted variations in healthcare delivery: implications for academic medical centres, BMJ, Oct. 26, 2002, pp. 961-964, vol. 325.
MaCurdy, T. et al., "Need for Risk Adjustment in Adapting Episode Grouping Software to Medicare Data," Health Care Financing Review, Summer 2009, pp. 33-46, vol. 30, Na 4.
Advancing Physician Performance Measurement: Using Administrative Data to Access Physician Quality and Efficiency, Pacific Business Group on Health, Sep. 2005, 36 pages.
Lucas, F. et al., "Temporal Trends in the Utilization of Diagnostic Testing and Treatments for Cardiovascular Disease in the United States, 1993-2001," Jan. 24, 2006, 12 pages, Circulation 113(3).
Stukel, T. et al., "Analysis of Observational Studies in the Presence of Treatment Selection Bias: Effects of Invasive Cardiac Management on AMI Survival Using Propensity Score and Instrumental Variable Methods," JAMA, Jan. 17, 2007, pp. 278-285, vol. 297, No. 3.
Sirovich, B. et al .,"Discretionary Decision Making by Primary Care Physicians and the Cost of U.S. Health Care," National Institute of Health, Jun. 24, 2008, pp. 813-823, vol. 27, Na I.
Stukel, T. et al., "Long-term Outcomes of Regional Variations in Intensity of Invasive vs. Medical Management of Medicare Patients With Acute Myocardial Infarction," JAMA, Mar. 16, 2005, pp. 1329-1337, vol. 293, Na it.
"Analytic Pathways System User's Guide", O'Pin Systems, Printed Aug. 1997. 313 Pages.

(56) References Cited

OTHER PUBLICATIONS

"Pathways: A powerful, clinically advanced provider profiling solution for understanding and managing health care costs and quality", Ingenix, Inc., Printed Jul. 1999. 247 Pages.

Cave, Douglas G., Proposal to Centers for Medicare and Medicaid Services ("CMS Proposal"), Dated Jan. 31, 2002. 43 Pages.

Forthman, M. Thane et al., "Episode Treatment Groups (ETGs): A Patient Classification System for Measuring Outcomes Performance by Episode of Illness", Topics in Health Information Management, Nov. 2000. 11 Pages.

"Episode Treatment Groups User's Guide: Release 4.4, Windows", Symmetry Health Data Systems Inc., Copyright 1993-2002. 175 Pages.

"Casualty Actuarial Society Forum: Winter 2000 Edition, Including the Ratemaking Papers and Health and Managed Care Call Papers", The Casualty Actuarial Society, 2000. 354 pages.

\* cited by examiner

Average Charge Per Episode of Care

| Medical Condition Name | SOI | Episode Count | Avg. Charge per Episode | Professional Outpt and Ambulatory | | | | | Prof Inpt | Facility | | Altern Sites (Svcs) | Other Med (Svcs) |
| --- | --- | --- | --- | --- | --- | --- | --- | --- | --- | --- | --- | --- | --- |
| | | | | Prof Visits | Diag Tests | Lab/ Path | Med/ Surg | Rx | | Outpt | Hosp Inpt | | |
| Peer Group Weighted Avg. | - | 46656 | $205 | $96 | $29 | $21 | $10 | $3 | $39 | $0 | $1 | $0 | $6 |
| Practitioner Weighted Avg. | - | 217 | $269 | $105 | $30 | $25 | $4 | $2 | $100 | $0 | $0 | $0 | $3 |
| Hypertension | 1 | 43 | $105 | $88 | $3 | $12 | $3 | $0 | $0 | $0 | $0 | $0 | $0 |
| Diabetes w/no complications | 1 | 23 | $217 | $113 | $25 | $54 | $25 | $0 | $0 | $0 | $0 | $0 | $0 |
| Diabetes with circulatory | 1 | 3 | $852 | $258 | $54 | $59 | $0 | $0 | $480 | $0 | $0 | $0 | $0 |
| Disorders of lipid metabolism | 1 | 26 | $61 | $23 | $0 | $38 | $0 | $0 | $0 | $0 | $0 | $0 | $0 |
| Ischemic heart disease | 1 | 8 | $207 | $89 | $19 | $24 | $0 | $0 | $75 | $0 | $0 | $0 | $0 |
| Congestive heart failure | 1 | 3 | $1620 | $350 | $99 | $63 | $0 | $0 | $1108 | $0 | $0 | $0 | $0 |
| Supraventricular arrhythmias | 1 | 5 | $126 | $55 | $32 | $31 | $0 | $0 | $0 | $0 | $0 | $0 | $7 |
| Heart valve disorders | 1 | 0 | $0 | $0 | $0 | $0 | $0 | $0 | $0 | $0 | $0 | $0 | $0 |
| COPD | 1 | 3 | $68 | $64 | $0 | $4 | $0 | $0 | $0 | $0 | $0 | $0 | $0 |
| Conduction disorders | 1 | 1 | $91 | $64 | $27 | $0 | $0 | $0 | $0 | $0 | $0 | $0 | $0 |
| Chest pain | 1 | 4 | $245 | $163 | $73 | $9 | $0 | $0 | $0 | $0 | $0 | $0 | $0 |
| Hypothyroidism | 1 | 14 | $98 | $49 | $3 | $41 | $5 | $0 | $0 | $0 | $0 | $0 | $0 |
| Low back pain | 1 | 9 | $89 | $31 | $19 | $0 | $0 | $0 | $0 | $0 | $0 | $0 | $40 |
| Cervical spine pain | 1 | 2 | $177 | $136 | $41 | $0 | $0 | $0 | $0 | $0 | $0 | $0 | $0 |
| Other arthropathy disorders | 1 | 4 | $103 | $84 | $9 | $10 | $0 | $0 | $0 | $0 | $0 | $0 | $0 |
| Anemia disorders | 1 | 4 | $280 | $156 | $40 | $82 | $0 | $0 | $0 | $0 | $0 | $0 | $1 |
| Urinary tract infections | 1 | 3 | $36 | $23 | $0 | $14 | $0 | $0 | $0 | $0 | $0 | $0 | $0 |
| Protatic hyperto & prostatitis | 1 | 4 | $69 | $31 | $9 | $29 | $0 | $0 | $0 | $0 | $0 | $0 | $0 |
| Acute bronchitis | 1 | 9 | $77 | $57 | $17 | $3 | $0 | $0 | $0 | $0 | $0 | $0 | $0 |
| Degenerative joint disease | 1 | 2 | $270 | $198 | $70 | $3 | $0 | $0 | $0 | $0 | $0 | $0 | $0 |
| Upper respiratory infections | 1 | 6 | $46 | $44 | $0 | $3 | $0 | $0 | $0 | $0 | $0 | $0 | $0 |
| Pneumonia | 1 | 3 | $367 | $53 | $12 | $0 | $0 | $0 | $302 | $0 | $0 | $0 | $0 |
| Asthma | 1 | 2 | $492 | $167 | $63 | $7 | $0 | $0 | $237 | $0 | $0 | $0 | $18 |
| Sinusitis | 1 | 3 | $48 | $48 | $0 | $0 | $0 | $0 | $0 | $0 | $0 | $0 | $0 |
| Gastroesphageal reflux | 1 | 1 | $48 | $48 | $0 | $0 | $0 | $0 | $0 | $0 | $0 | $0 | $0 |
| Abdominal pain | 1 | 10 | $104 | $63 | $34 | $7 | $0 | $0 | $0 | $0 | $0 | $0 | $0 |
| Vertiginous syndromes | 1 | 4 | $147 | $80 | $65 | $2 | $0 | $0 | $0 | $0 | $0 | $0 | $0 |
| Osteoporosis | 1 | 0 | $0 | $0 | $0 | $0 | $0 | $0 | $0 | $0 | $0 | $0 | $0 |
| Rheumatoid arthritis | 1 | 0 | $0 | $0 | $0 | $0 | $0 | $0 | $0 | $0 | $0 | $0 | $0 |
| Bursitis | 1 | 1 | $211 | $103 | $31 | $0 | $77 | $0 | $0 | $0 | $0 | $0 | $0 |
| Headaches | 1 | 4 | $234 | $48 | $34 | $6 | $0 | $0 | $146 | $0 | $0 | $0 | $0 |
| Cellul & abscess, other site | 1 | 0 | $0 | $0 | $0 | $0 | $0 | $0 | $0 | $0 | $0 | $0 | $0 |
| Gout | 1 | 3 | $242 | $150 | $7 | $32 | $0 | $0 | $0 | $0 | $0 | $0 | $53 |
| Dermatitis and eczema | 1 | 3 | $80 | $69 | $12 | $0 | $0 | $0 | $0 | $0 | $0 | $0 | $0 |
| General presenting symptoms | 1 | 7 | $90 | $60 | $20 | $5 | $0 | $0 | $0 | $0 | $0 | $0 | $5 |

FIG. 8

Average Utilization Per Episode of Care

| Medical Condition Name | SOI | Episode Count | Avg. Episode Duration (Days) | Professional Outpt and Ambulatory | | | | | Prof Inpt (Svcs) | Facility | | | Altern Sites (Svcs) | Other Med (Svcs) |
|---|---|---|---|---|---|---|---|---|---|---|---|---|---|---|
| | | | | Prof Visits | Diag Tests | Lab/ Path | Med/ Surg | Rx | | Outpt (Visits) | Hosp Inpt Admits | Hosp Inpt Days | | |
| Peer Group Weighted Avg. | - | 46656 | 122.8 | 1.77 | 0.75 | 3.05 | 0.14 | 0.06 | 0.65 | 0.00 | 0.00 | 0.00 | 0.00 | 0.00 |
| Practitioner Weighted Avg. | - | 217 | 123.6 | 2.00 | 1.09 | 3.43 | 0.07 | 0.04 | 1.92 | 0.00 | 0.00 | 0.00 | 0.00 | 0.00 |
| Hypertension | 1 | 43 | 180.0 | 1.72 | 0.12 | 1.74 | 0.02 | 0.00 | 0.00 | 0.00 | 0.00 | 0.00 | 0.00 | 0.00 |
| Diabetes w/no complications | 1 | 23 | 180.0 | 2.30 | 0.87 | 6.78 | 0.48 | 0.00 | 10.00 | 0.00 | 0.00 | 0.00 | 0.00 | 0.00 |
| Diabetes with circulatory | 1 | 3 | 180.0 | 5.00 | 3.33 | 7.33 | 0.00 | 0.00 | 0.00 | 0.00 | 0.00 | 0.00 | 0.00 | 0.00 |
| Disorders of lipid metabolism | 1 | 26 | 180.0 | 0.54 | 0.00 | 4.08 | 0.00 | 0.00 | 1.50 | 0.00 | 0.00 | 0.00 | 0.00 | 0.00 |
| Ischemic heart disease | 1 | 8 | 180.0 | 1.88 | 0.62 | 3.75 | 0.00 | 0.00 | 20.67 | 0.00 | 0.00 | 0.00 | 0.00 | 0.00 |
| Congestive heart failure | 1 | 3 | 180.0 | 6.33 | 3.33 | 10.67 | 0.00 | 0.00 | 0.00 | 0.00 | 0.00 | 0.00 | 0.00 | 0.00 |
| Supraventricular arrhythmias | 1 | 5 | 180.0 | 1.20 | 1.00 | 5.00 | 0.00 | 0.00 | 0.00 | 0.00 | 0.00 | 0.00 | 0.00 | 0.00 |
| Heart valve disorders | 1 | 0 | 0.0 | 0.00 | 0.00 | 0.00 | 0.00 | 0.00 | 0.00 | 0.00 | 0.00 | 0.00 | 0.00 | 0.00 |
| COPD | 1 | 3 | 180.0 | 1.33 | 0.00 | 0.33 | 0.00 | 0.00 | 0.00 | 0.00 | 0.00 | 0.00 | 0.00 | 0.00 |
| Conduction disorders | 1 | 1 | 180.0 | 1.00 | 1.00 | 0.00 | 0.00 | 0.00 | 0.00 | 0.00 | 0.00 | 0.00 | 0.00 | 0.00 |
| Chest pain | 1 | 4 | 8.0 | 2.00 | 4.00 | 0.75 | 0.00 | 0.00 | 0.00 | 0.00 | 0.00 | 0.00 | 0.00 | 0.00 |
| Hypothyroidism | 1 | 14 | 180.0 | 1.07 | 0.07 | 2.93 | 0.07 | 0.00 | 0.00 | 0.00 | 0.00 | 0.00 | 0.00 | 0.00 |
| Low back pain | 1 | 9 | 29.4 | 0.67 | 0.89 | 0.00 | 0.00 | 0.00 | 0.00 | 0.00 | 0.00 | 0.00 | 0.00 | 0.00 |
| Cervical spine pain | 1 | 2 | 42.5 | 3.50 | 2.00 | 0.00 | 0.00 | 0.00 | 0.00 | 0.00 | 0.00 | 0.00 | 0.00 | 0.00 |
| Other arthropathy disorders | 1 | 4 | 48.0 | 1.75 | 0.50 | 1.50 | 0.00 | 0.00 | 0.00 | 0.00 | 0.00 | 0.00 | 0.00 | 0.00 |
| Anemia disorders | 1 | 4 | 135.8 | 2.50 | 1.50 | 15.25 | 0.00 | 1.00 | 0.00 | 0.00 | 0.00 | 0.00 | 0.00 | 0.00 |
| Urinary tract infections | 1 | 3 | 8.3 | 0.67 | 0.00 | 1.67 | 0.00 | 0.00 | 0.00 | 0.00 | 0.00 | 0.00 | 0.00 | 0.00 |
| Prostatic hyperto & prostatitis | 1 | 4 | 45.8 | 0.50 | 0.50 | 2.25 | 0.00 | 0.00 | 0.00 | 0.00 | 0.00 | 0.00 | 0.00 | 0.00 |
| Acute bronchitis | 1 | 9 | 1.2 | 1.33 | 1.00 | 0.44 | 0.00 | 0.00 | 0.00 | 0.00 | 0.00 | 0.00 | 0.00 | 0.00 |
| Degenerative joint disease | 1 | 2 | 180.0 | 3.00 | 2.50 | 0.50 | 0.00 | 0.00 | 0.00 | 0.00 | 0.00 | 0.00 | 0.00 | 0.00 |
| Upper respiratory infections | 1 | 6 | 1.0 | 1.00 | 0.00 | 0.17 | 0.00 | 0.00 | 0.00 | 0.00 | 0.00 | 0.00 | 0.00 | 0.00 |
| Pneumonia | 1 | 3 | 5.0 | 1.00 | 0.67 | 0.00 | 0.00 | 0.00 | 6.00 | 0.00 | 0.00 | 0.00 | 0.00 | 0.00 |
| Asthma | 1 | 2 | 180.0 | 3.00 | 2.50 | 1.00 | 0.00 | 0.00 | 3.50 | 0.00 | 0.00 | 0.00 | 0.00 | 0.00 |
| Sinusitis | 1 | 3 | 1.0 | 1.00 | 0.00 | 0.00 | 0.00 | 0.00 | 0.00 | 0.00 | 0.00 | 0.00 | 0.00 | 0.00 |
| Gastroesphageal reflux | 1 | 1 | 1.0 | 1.00 | 0.00 | 0.00 | 0.00 | 0.00 | 0.00 | 0.00 | 0.00 | 0.00 | 0.00 | 0.00 |
| Abdominal pain | 1 | 10 | 16.5 | 1.30 | 0.50 | 1.20 | 0.00 | 0.00 | 0.00 | 0.00 | 0.00 | 0.00 | 0.00 | 0.00 |
| Vertiginous syndromes | 1 | 4 | 14.8 | 1.25 | 1.75 | 0.50 | 0.00 | 0.00 | 0.00 | 0.00 | 0.00 | 0.00 | 0.00 | 0.00 |
| Osteoporosis | 1 | 0 | 0.0 | 0.0 | 0.00 | 0.00 | 0.00 | 0.00 | 0.00 | 0.00 | 0.00 | 0.00 | 0.00 | 0.00 |
| Rheumatoid arthritis | 1 | 0 | 0.0 | 0.0 | 0.00 | 0.00 | 0.00 | 0.00 | 0.00 | 0.00 | 0.00 | 0.00 | 0.00 | 0.00 |
| Bursitis | 1 | 1 | 18.0 | 3.00 | 2.00 | 0.00 | 1.00 | 0.00 | 0.00 | 0.00 | 0.00 | 0.00 | 0.00 | 0.00 |
| Headaches | 1 | 4 | 14.0 | 1.00 | 0.50 | 1.25 | 0.00 | 0.00 | 2.75 | 0.00 | 0.00 | 0.00 | 0.00 | 0.00 |
| Cellul & abscess, other site | 1 | 0 | 0.0 | 0.0 | 0.00 | 0.00 | 0.00 | 0.00 | 0.00 | 0.00 | 0.00 | 0.00 | 0.00 | 0.00 |
| Gout | 1 | 3 | 180.0 | 2.67 | 0.67 | 4.00 | 0.00 | 0.00 | 0.00 | 0.00 | 0.00 | 0.00 | 0.00 | 0.00 |
| Dermatitis and eczema | 1 | 3 | 7.0 | 1.67 | 0.67 | 0.00 | 0.00 | 0.00 | 0.00 | 0.00 | 0.00 | 0.00 | 0.00 | 0.00 |
| General presenting symptoms | 1 | 7 | 7.0 | 0.86 | 0.71 | 0.71 | 0.00 | 0.00 | 0.00 | 0.00 | 0.00 | 0.00 | 0.00 | 0.00 |

FIG. 9

METHOD, SYSTEM, AND COMPUTER PROGRAM PRODUCT FOR PHYSICIAN EFFICIENCY MEASUREMENT AND PATIENT HEALTH RISK STRATIFICATION

CROSS-REFERENCE TO RELATED APPLICATIONS

This application is a Continuation of co-pending U.S. patent application Ser. No. 14/269,084, filed May 3, 2014, which is a Continuation of U.S. patent application Ser. No. 13/794,765, filed Mar. 11, 2013, and issued as U.S. Pat. No. 8,768,726 on Jul. 1, 2014, which is a Continuation of U.S. patent application Ser. No. 13/621,234, filed Sep. 15, 2012, which is a Continuation of U.S. patent application Ser. No. 13/012,219, filed Jan. 24, 2011, and issued as U.S. Pat. No. 8,340,981 on Dec. 25, 2012, which is a Continuation-in-part (CIP) of abandoned U.S. patent application Ser. No. 12/769,090, filed Apr. 28, 2010, which is a Continuation of U.S. patent application Ser. No. 10/794,216, filed Mar. 5, 2004, and issued as U.S. Pat. No. 7,739,126 on Jun. 15, 2010, which claims the benefit of U.S. Provisional Patent Application Ser. No. 60/549,601, filed Mar. 2, 2004, all of which are hereby incorporated by reference in their entirety as if set forth herein.

BACKGROUND OF THE INVENTION

1. Field of the Invention

The present invention relates broadly to management of medical information. More specifically, the present invention relates to management of medical information to perform and report measurements of physician efficiency.

2. The Prior Art

Recent evidence has suggested that about 10-20% of physicians, across specialty types, practice inefficiently. Efficient means using the appropriate amount of medical resources to treat a medical condition and achieve a desired health outcome. Thus, efficiency is a function of unit price, volume of service, intensity of service, and quality of service. This group of inefficient physicians is responsible for driving 10% to 20% of the unnecessary, excess medical expenditures incurred by employers and other healthcare purchasers, equating to billions of dollars nationally.

To improve market efficiency, it is useful to apply a system that accurately measures individual physician efficiency. Recent evidence has demonstrated that leading physician efficiency measurement systems have only about 15-30% agreement across measurement systems. This means that when one system ranks a physician as inefficient, only about 15-30% of the other systems ranked the same physician as inefficient. The remaining 70% (or more) of systems ranked the same physician as efficient.

These findings show that existing systems have significant error in attempting to accurately identify inefficient physicians. The error needs to be eliminated, or significantly reduced, if healthcare purchasers are to accurately identify inefficient physicians and take action (e.g., attempt to change physician behavior, provide incentives for employees to use more efficient physicians). Every physician falsely measured as efficient (or inefficient) leads to continued inefficiency in the healthcare marketplace.

There are ten common physician (or physician group) efficiency measurement errors present in most existing physician efficiency measurement systems, which are in order of importance: (1) examine all episodes of care for a physician; (2) use a physician's actual episode composition; (3) no severity-of-illness measure by medical condition; (4) no identification of different episode treatment stages; (5) no age category assignment by medical condition; (6) no tracking mechanism for related complication episodes; (7) improper episode outlier criteria; (8) under-report charges attributed to partial episodes; (8) over-report charges attributed to episode endpoints; and (10) no minimum number of episodes of care. These errors are discussed next.

Many physician efficiency methodologies continue to examine "services per 1,000 members" or "all episodes of care" tracked to a physician. These approaches probably add the most to efficiency measurement error. The methodologies attempt to adjust services per 1,000 members and to adjust all episodes of care by age and gender—and then compare one physician's utilization pattern to a peer group average. However, age and gender explain less than 5% of the variance in a patient's medical expenditures. This means that over 95% of the variance is unexplained, and may be attributed to differences in patient health status.

Some methodologies adjust services per 1,000 members and adjust all episodes of care based on specific International Clinical Modification of Diseases ninth edition (ICD.9) code algorithms that measure expected resource intensity. The idea is that a patient's diagnosis codes will provide more predictive power than age and gender alone. The most predictive of the published and marketed models explain only 20% to 30% of the variance in a patient's medical expenditures. This means that 70% or more of the variance continues to be unexplained, and may be attributed to differences in patient health status.

Physicians often criticize the services per 1,000 members and the all episodes of care methodologies that use a predictive case-mix adjustment factor. Physicians state that the methodologies do not appropriately adjust for differences in patient health status—rightly stating that their patients may be "sicker."

If all claim line items (CLIs) or episodes of care tracked to a physician are used in the efficiency analysis, then up to 70% of the observed utilization difference between physicians may be attributed to patient health status differences. Therefore, patient health status differences are measured rather than individual physician efficiency differences. This weakness in current case-mix adjustment tools means that not all CLIs or patient episodes of care treated by a physician can be examined. Instead, an isolated set of more prevalent medical conditions by severity-of-illness level needs to be examined across physicians of a similar specialty type.

The second measurement error, which occurs in most if not all current efficiency measurement systems, occurs when the physician's actual episode composition is used. The reason is as follows. The differences in physicians' patient case-mix composition results in differences in variability (i.e., the standard deviation) around a physician's average episode treatment charges. This variability is not due to the efficiency or inefficiency of a physician, but instead results because longer and more resource-intensive medical conditions generally require more services and, therefore, have more potential variability around average (or mean) episode treatment charges.

For example, easier-to-treat upper respiratory infection (URI) episodes may have the following mean and standard deviation (with outlier episodes removed): $185±$65. Here, the standard deviation around the mean is not large—and is 0.35 the size of the mean (i.e., 65/185=0.35). However, easier-to-treat pediatric asthma episodes may have the following mean and standard deviation (with outlier episodes removed): $1,650±$850. Here, the standard deviation around the mean is larger than for URI episodes—and is 0.52 the size of the mean (i.e., 850/1,650=0.52).

The variation difference between the two conditions is 49% greater for asthma than URIs [(0.52−0.35)/0.35]. This variation difference occurs for two reasons: (1) more resource-intensive conditions require more services to treat; and (2) there generally are a small number of episodes available to examine in a given physician efficiency study as compared to the universe of episodes that could actually be studied—and a smaller number of episodes results in a higher chance for variability around the mean. This variation is not the result of physician treatment pattern differences.

If the statistically based variability around the mean is not corrected, then substantial error may enter into the physician efficiency measurement equation. Consequently, the final physician efficiency score differences may be attributed to the statistical condition-specific variability around the mean episode charge (due to the case-mix of episodes treated).

The above example showed that the variation difference may be 50% or more (around a condition-specific mean episode value). Logically, then, if all episodes treated by physicians are examined and efficiency scores are calculated, there has to be some statistical bias present.

A significant statistical bias may be present. Using a more traditional episode-based efficiency measurement methodology, lower-episode-volume physicians treating patients with a higher case-mix index score are more likely to receive an inefficient ranking as compared to lower-episode-volume physicians treating patients with a lower case-mix index score. This finding results because a physician with higher case-mix patients treats episodes having more variability (i.e., a greater standard deviation) around average episode treatment charges. With a low volume of episodes (most often the norm, and not the exception), this physician needs only a few higher-cost episodes then the peer group average to make his/her treatment pattern appear significantly higher than the peer group comparator.

However, a physician with lower case-mix patients treats episodes having less variability around average episode treatment charges. With a low volume of episodes, this physician's treatment pattern will not be as influenced by one or two higher-cost episodes as compared to the peer group average. Consequently, his/her treatment pattern does not appear (as often) significantly higher than the peer group comparator.

Thus, by examining all medical condition episodes, a substantial component of any observed physician efficiency difference may be attributed to statistical condition-specific variability around the mean episode charge—and not to physician treatment patterns efficiency. This effect may be present even when we examine the easier-to-treat episodes (SOI-1 level episodes) for the medical conditions.

The third error takes place in those efficiency measurement systems that do not employ an appropriate episode severity-of-illness measure. Severity-of-illness may be defined as the probability of loss of function due to a specific medical condition. Most, if not all, current claims-based episode groupers and methods do not have an appropriate severity-of-illness index by medical condition. Consequently, significant clinical heterogeneity remains in many episodes for a given medical condition. The end result may be physician efficiency differences that are attributed to inaccurate episode severity-of-illness adjustment, and not to physician treatment patterns variation.

Moreover, some claims-based episode groupers stratify formulated episodes for a medical condition by the presence or absence of a specific surgery or service (e.g., knee derangement with and without surgery; ischemic heart disease with and without heart catheterization). The reason for performing this stratification is to reduce episode heterogeneity for a medical condition. In effect, the stratification serves as a sort of severity-of-illness adjustment.

However, stratification based on the presence of surgery or a high-cost service results in at least two physician efficiency measurement errors: (1) performing surgery versus not performing surgery is the treatment patterns variation we need to examine in determining physician efficiency, and this variation is not captured in more traditional methodologies; and (2) the episodes of care are unnecessarily separated into smaller groups whereby physicians may not have enough episodes to examine in any one smaller group. Consequently, the stratified episodes of care need to be recombined for accurate physician efficiency measurement.

The fourth physician efficiency measurement error occurs in claims-based episode groupers do not have a method for identifying different episode treatment stages including initial, active, and follow-up treatment stages. Identifying different treatment stages is important in medical conditions, such as breast cancer, prostate cancer, colorectal cancer, acute myocardial infarction, and lymphoma. For example, breast cancer should be stratified into initial, active, and follow-up treatment stages.

An initial breast cancer episode is one where the patient has a surgery for the cancer (e.g., lumpectomy, modified radial mastectomy). An active breast cancer episode is one where no surgery is present, but chemotherapy or radiation treatment is observed within the episode. Here, the patient underwent surgery in a previous study period, so no surgical event is found in the patient's current ongoing breast cancer episode. Instead, during the study period, the claims data shows that the patient is being treated with chemotherapy and/or radiation. The presence of these treatments defines an active breast cancer episode. The utilization pattern and charges are different for an active breast cancer patient as compared to an initial breast cancer patient. A follow-up breast cancer episode is one where no surgery, chemotherapy, or radiation treatment is present in the patient's episode of care. After initial and active treatments, physicians will continue to code for breast cancer over the future years of patient follow-up care.

In a given study period, physicians do not treat an equal distribution of each episode type (initial, active, and follow-up). Moreover, the episode types have different average charges. About 20% of episodes may be classified as initial breast cancer episodes. Overall care for initial breast cancer episodes ranges between $15,000 and $25,000 per episode. About 15% of episodes may be classified as active breast cancer episodes. Overall care for active breast cancer episodes ranges between $12,000 and $18,000 per episode. About 65% of episodes may be classified as follow-up breast cancer episodes. Overall care for follow-up breast cancer episodes ranges between $350 and $600 per episode.

Consequently, the blending of the three treatment stage episodes results in average treatment charges of about $5,500 to $6,500 per episode. In fact, this is the average breast cancer charge that would be observed for most claims-based episode groupers.

The blending of initial, active, and follow-up episodes may lead to substantial physician efficiency measurement error. For example, assume during a study period that Oncologist A treats mostly active breast cancer patients, while some other oncologists have a good mixture of active and follow-up patients. Then, Oncologist A's treatment pattern for breast cancer will appear inefficient (as compared to his peer group of oncologists) because active episodes are about 30 times more expensive to treat than follow-up episodes. In fact, Oncologist A's treatment pattern difference is attributed to a different treatment stage episode case-mix.

Therefore, treatment stage episode types need to be correctly identified and separately examined. Otherwise, the final physician efficiency score differences may be attributed to nothing more than the initial, active, and follow-up episode case-mix.

The fifth error happens in those physician efficiency measurement systems that do not examine condition-specific episodes by age category. Studies have illustrated that broad-based age bands are important to separately examine—even after episodes have been assigned a severity-of-illness index. The reason is that physicians tend to treat children and adults differently for most conditions. For example, children are less likely than adults to receive a chest x-ray and potent antibiotics for many medical conditions. If episodes are not examined by broad-based age category, the end result may be physician efficiency differences that are attributed to patient age differences—and not to treatment patterns variation.

The sixth error occurs in those physician efficiency measurement systems that do not link and include the charges and utilization from a patient's complication episodes to his underlying medical condition. Complications are those episodes that are clinically related to the underlying medical condition. Consequently, many condition-specific episodes have under-reported charges. In fact, actual outputs from some claims-based episode groupers may show under-reported charges for patients with diabetes and other chronic conditions (e.g., asthma, congestive heart failure).

For example, the reason for the under-reported episode charges is that physicians code up to 70% of an average diabetic's charges under related complications to the diabetes (e.g., eye, neuropathies, circulatory, renal) and not diabetes care. Therefore, without considering and including related complication episodes with the actual diabetes episode, physician efficiency differences may be attributed to incomplete episode charges and utilization—and not to treatment pattern variations.

Furthermore, for patients with specific medical conditions, any model that attempts to stratify patients by health risk may produce unstable or erroneous results. The reason is that a patient is missing key claims information needed to accurately classify a patient into an appropriate severity-of-illness and other classes. For example, without tracking related complications to a diabetic patient, many diabetic patients will appear to have no complications when in fact they have eye or circulatory complications.

The seventh physician efficiency measurement error happens when the condition-specific outlier episode analysis is not performed in an appropriate manner. Many current methodologies perform the high-end outlier analysis by eliminating a percent of condition-specific episodes at the peer group (or aggregate episode) level. That is, the methodologies eliminate the high-end outliers before assigning episodes to physicians.

However, this method results in physician efficiency measurement error because a higher proportion of episodes assigned to the most inefficient physicians will be eliminated (as compared to the proportion of episodes eliminated for efficient physicians). Consequently, the inefficient physicians' condition-specific treatment patterns now more closely resemble the treatment patterns of the efficient physicians.

An example demonstrates this error. Assume Physician A has seven episodes of acute bronchitis with the following per episode charges: $235, $245, $325 $400, $525, $550, and $600. Also, the outlier cut-off threshold for high-end outlier episodes is set at $399 at the peer group level. Physician A now has only three episodes remaining at $235, $245, $325. The mean charge is $268 per episode. Assume Physician B also has 7 episodes of acute bronchitis with the following per episode charges: $210, $225, $235, $255, $285, $320, and $390. The peer-group level outlier threshold remains at $399. Therefore, Physician B has all seven episodes remaining, and the mean charge is $274.

The end result shows no statistical difference between Physicians A and B. The mean episode charge of Physician A is slightly lower than Physician B (i.e., $268 versus $274 per episode). However, using an outlier rule where we eliminate 5% of episodes (or at least 1 high-end outlier) are eliminated at the physician level, the results are significantly different. Physician A now has six remaining episodes (i.e., here we eliminate only 1 high-end outlier), and the mean charge of the six non-outlier episodes is now $380 per episode. For Physician B, the mean charge for the six non-outlier episodes is now $255 per episode. Physician A is statistically higher in average (or mean) episode charges than Physician B by $125 per episode.

The eighth error occurs in those systems that under-report charges attributed to partial (or incomplete) episodes of care. Some methodologies do not separate partial from complete episodes of care when measuring physician efficiency. Partial episodes result because a patient enrolled in a health plan during the study period or disenrolled during the study period. However, including partial episodes leads to inaccurate efficiency measurement because of under-reported episode charges—especially when some physicians have more partial episodes than other physicians.

A reason partial episodes often slip through the cracks and into an efficiency analysis is because the methodologies do not use a membership eligibility file to ensure the member is present for the entire study period. Instead, the methods assume that a condition-specific episode of care is complete if the episode exceeds some minimum duration time period. For example, if a patient's episode of diabetes is 40 days or more in duration, then the episode is marked as complete—and not partial. If a patient's diabetes episode is 39 days or less, then the episode is marked as partial.

Applying an indiscriminate time period duration to condition-specific episodes produces a high percentage of episodes marked as complete, which are actually partial (or incomplete) episodes. That is, many health plan's have membership turnover rates of 20% or higher. Consequently, a diabetes episode of 40 days duration—marked as complete—has at least a 20% chance of being a partial episode of care because of membership turnover. The end result may be physician efficiency differences that are attributed to the inclusion of partial episodes—and not to treatment patterns variation.

The ninth error happens in physician efficiency measurement systems that over-report charges attributed to episode endpoints. Some methodologies do not appropriately end a patient's episode of care before measuring a physician's efficiency. For example, chronic conditions may continue indefinitely and, therefore, patient episodes of care may be of various durations (e.g., 60 days or 600 days)—depending on the amount of available patient claims data. The end result may be physician efficiency differences that are attributed to excessively long or variable chronic condition episode durations—and not to treatment patterns variation.

The tenth error takes place in those systems that impose few requirements for having a minimum number of episodes in a certain number of medical conditions. Many methodologies do not require a minimum number of condition-specific episodes when comparing a physician's efficiency to a peer group. Instead, only a small handful (e.g., less than 10 episodes) are enough. However, there may be significant episode of care heterogeneity in one or two condition-specific episodes—even after applying a sophisticated severity-of-illness index. Consequently, examining an episode here-and-there for a physician may introduce significant error into a physician's efficiency measurement. The end result may be physician efficiency differences that are attributed to the heterogeneity in the low number of episodes examined—and not to treatment patterns variation.

Various systems have been patented in the episode of care field. Such systems are shown, for example, in U.S. Pat. Nos. 5,557,514, 5,835,897 and 5,970,463. However, none of these systems adequately overcome the aforementioned problems with respect to appropriately building and analyzing episodes of care. As importantly, existing systems fail to discuss an episode-of-care-based system for measuring individual or physician group efficiency measurement.

BRIEF SUMMARY OF THE INVENTION

In one aspect, the present invention provides a method of determining physician efficiency. The method comprises: obtaining medical claims data; performing patient analysis using the obtained medical claims data to form episodes of care; performing output process based on performed patient analysis, the output process comprising at least one act selected from the group consisting of: eliminating partial episodes of care and episodes of care marked with comorbidities; assigning episodes to physicians; grouping claim line items in episodes to service categories; and applying a maximum duration rule to episodes of care; assigning at least one physician to a report group; determining eligible physicians and episode assignments by performing at least one act selected from the group consisting of: eliminating physicians from the report group, the eliminated physicians having specialties that are not assigned to a grouping of medical conditions that account for some episodes treated by a physician having a specialty type; eliminating physicians that are not in a report group of interest; and eliminating episode assignments not meeting a selected criterion; calculating condition-specific episode statistics; calculating weighted episode statistics across medical conditions; and determining efficiency scores for physicians from the calculated condition-specific episode statistics and the weighted episode statistics calculated across medical conditions.

In an embodiment, the act of calculating condition-specific episode statistics comprises calculating condition-specific episode statistics for physicians in the report group. In an embodiment, the act of calculating condition-specific episode statistics comprises calculating condition-specific episode statistics for peer groups. In an embodiment, the act of calculating weighted episode statistics comprises calculating peer group weighted episode statistics across medical conditions. In an embodiment, the act of calculating weighted episode statistics comprises calculating physician weighted episode statistics across medical conditions.

In another aspect, the present invention provides a computer program product tangibly embodied in computer instructions which, when executed by a computer, determine physician efficiency. The computer instructions, when executed, perform the acts of: obtaining medical claims data; performing patient analysis using the obtained medical claims data to form episodes of care; performing output process based on performed patient analysis, the output process comprising at least one act selected from the group consisting of: eliminating partial episodes of care and episodes of care marked with comorbidities; assigning episodes to physicians; grouping claim line items in episodes to service categories; and applying a maximum duration rule to episodes of care; assigning at least one physician to a report group; determining eligible physicians and episode assignments by performing at least one act selected from the group consisting of: eliminating physicians from the report group, the eliminated physicians having specialties that are not assigned to a grouping of medical conditions that account for some episodes treated by a physician having a specialty type; eliminating physicians that are not in a report group of interest; and eliminating episode assignments not meeting a selected criterion; calculating condition-specific episode statistics; calculating weighted episode statistics across medical conditions; and determining efficiency scores for physicians from the calculated condition-specific episode statistics and the weighted episode statistics calculated across medical conditions.

In an embodiment, the act of calculating condition-specific episode statistics comprises calculating condition-specific episode statistics for physicians in the report group. In an embodiment, the act of calculating condition-specific episode statistics comprises calculating condition-specific episode statistics for peer groups. In an embodiment, the act of calculating weighted episode statistics comprises calculating peer group weighted episode statistics across medical conditions. In an embodiment, the act of calculating weighted episode statistics comprises calculating physician weighted episode statistics across medical conditions.

In yet another aspect, the present invention provides a system for determining physician efficiency. The system comprises means for obtaining medical claims data; means for performing patient analysis using the obtained medical claims data to form episodes of care; means for performing output process based on performed patient analysis, the output process comprising at least one act selected from the group consisting of: eliminating partial episodes of care and episodes of care marked with comorbidities; assigning episodes to physicians; grouping claim line items in episodes to service categories; and applying a maximum duration rule to episodes of care; means for assigning at least one physician to a report group; means for determining eligible physicians and episode assignments by performing at least one act selected from the group consisting of: eliminating physicians from the report group, the eliminated physicians having specialties that are not assigned to a grouping of medical conditions that account for some episodes treated by a physician having a specialty type; eliminating physicians that are not in a report group of interest; and eliminating episode assignments not meeting a selected criterion; means for calculating condition-specific episode statistics; means for calculating weighted episode statistics across medical conditions; and means for determining efficiency scores for physicians from the calculated condition-specific episode statistics and the weighted episode statistics calculated across medical conditions.

In an embodiment, the means for calculating condition-specific episode statistics comprises means for calculating condition-specific episode statistics for physicians in the report group. In an embodiment, the means for calculating condition-specific episode statistics comprises means for calculating condition-specific episode statistics for peer groups. In an embodiment, the means for calculating weighted episode statistics comprises means for calculating peer group weighted episode statistics across medical conditions. In an embodiment, the means for calculating weighted episode statistics comprises means for calculating physician weighted episode statistics across medical conditions.

In yet another aspect, the present invention provides a method of performing patient health risk stratification, the method comprising: obtaining medical claims data; performing patient analysis using the obtained medical claims data to form episodes of care; and performing output process based on performed patient analysis, the output process comprising at least one act selected from the group consisting of: eliminating partial episodes of care and episodes of care marked with comorbidities; assigning episodes to physicians; grouping claim line items in episodes to service categories; and applying a maximum duration rule to episodes of care.

In yet another aspect, the present invention provides a computer program product tangibly embodied in computer instructions which, when executed by a computer, performs patient health risk stratification. The computer instructions, when executed, perform the acts of: obtaining medical claims data; performing patient analysis using the obtained medical claims data to form episodes of care; and performing output process based on performed patient analysis, the output process comprising at least one act selected from the group consisting of: eliminating partial episodes of care and episodes of care marked with comorbidities; assigning episodes to physicians; grouping claim line items in episodes to service categories; and applying a maximum duration rule to episodes of care.

In yet another aspect, the present invention provides a system for performing patient health risk stratification. The system comprises: means for obtaining medical claims data; means for performing patient analysis using the obtained medical claims data to form episodes of care; and means for performing output process based on performed patient analysis, the output process comprising at least one act selected from the group consisting of: eliminating partial episodes of care and episodes of care marked with comorbidities; assigning episodes to physicians; grouping claim line items in episodes to service categories; and applying a maximum duration rule to episodes of care.

Additional features and advantages of the present invention will be realized by one skilled in the art upon reading the following detailed description, when considered in conjunction with the accompanying drawings.

BRIEF DESCRIPTION OF THE DRAWINGS

FIG. 8 illustrates, in tabular form, a Practitioner Efficiency Measurement Report 1, detailing average charges per episode of care.

FIG. 9 illustrates, in tabular form, a Practitioner Efficiency Measurement Report 2, detailing average utilization per episode of care

DETAILED DESCRIPTION

Step A: Utilize Claims Data File

Figure 1:
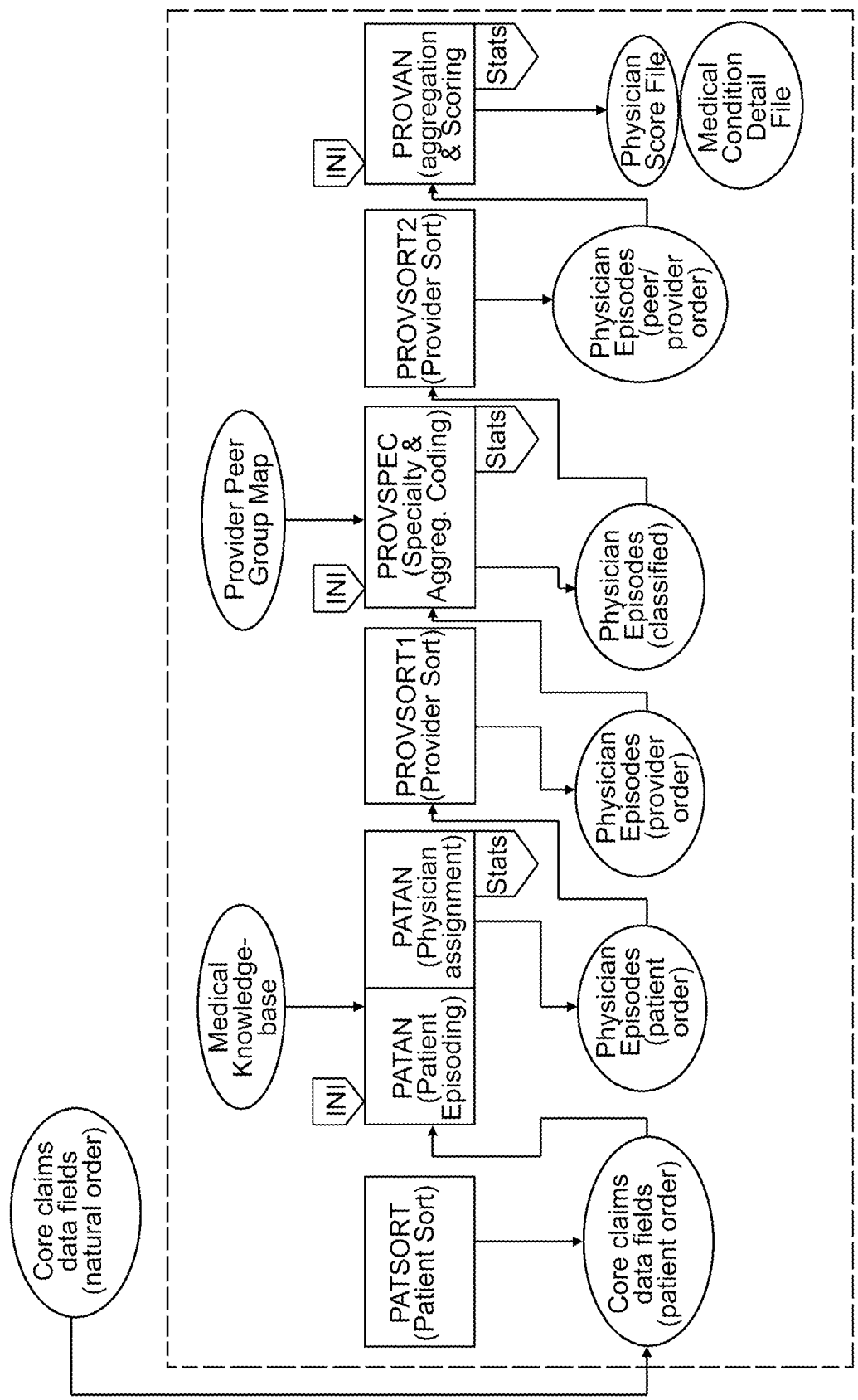
FIG. 1 is a drawing that illustrates, in flow diagram form, functional aspects of the present invention.
Figure 2:
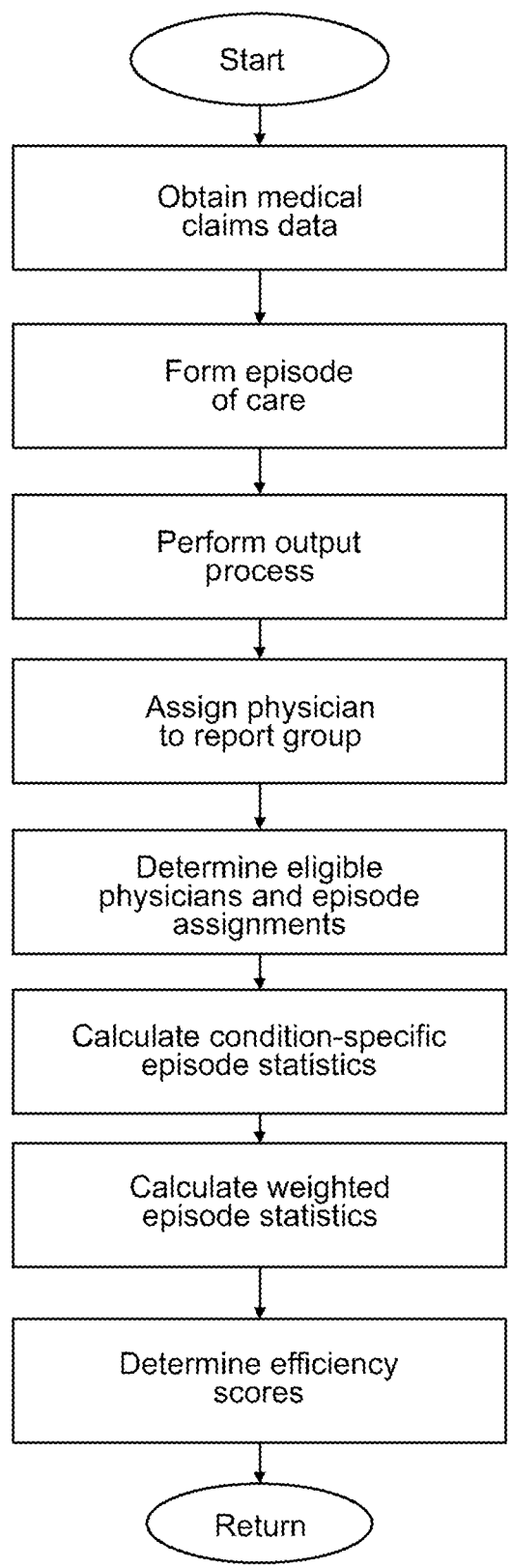
FIG. 2 is a flowchart that illustrates, in flow diagram form, a sequence of acts executed in accordance with embodiments of the present invention.

Medical claims data is utilized in an embodiment of the present invention, and generally consists of a family, member, claim, and claim line item (CLI) structure. A claim generally consists of one or more CLIs. The claims data consists of medical events that are incurred by the patient visiting a healthcare professional or a facility in the ambulatory, outpatient, inpatient, home, and other environments where medical services may be delivered.

Step B: Extract Core Claims Data Fields

In order to form longitudinal episodes of care, assign them to physicians, and analyze individual physician efficiency, medical claims data must be mapped to the system requirements of the present invention. The process maps medical claims by performing field mapping and field value mapping. In field mapping, fields in the source data are identified that correspond to each of the required fields. In field value mapping, for each field where applicable, the user determines the field value that corresponds to each possible value that may occur in the source data.

Five types of data are mapped: client-defined codes, value fields, dates, system-specific codes, and standard codes. The present invention uses client-defined codes for physicians and members. Value fields include dollar amount, counts, and similar numeric data according to specified value formats. Calendar dates are mapped according to the specified standard format. System-specific codes include provider type, place of service, physician specialty, type of service, and similar codes. Standard codes include CPT codes, ICD.9 procedural codes, and similar codes.

A record refers to a CLI. The mapped claims file consists of one output record for each record in the source data, except those that are duplicates resulting from adjudication process. The field byte size is noted in Table 1 below. Each record is terminated by a one byte end-of-line character.

The present invention uses the fields in the following table. Mandatory fields must be filled for all records in the order listed for correct functionality of the present invention. Non-mandatory fields are optional.

TABLE 1

CLI Mapping Code Fields

| Field Number | Type | Name & Description | Format | Mandatory or Non-mandatory |
|---|---|---|---|---|
| 1 | 1 | Primary subscriber identifier. The subscriber number used to identify a family unit. | 15 char | M |
| 2 | 1 | Member identifier. The unique identifier of a person within a family. The field value should uniquely identify an individual when combined with the primary subscriber identifier (field #1). | 15 char | M |
| 3 | 3 | Claim start date. Date of first service on a claim. | 8 date yyyymmdd | NM |
| 4 | 3 | Claim end date. Date of last service on a claim. | 8 date yyyymmdd | NM |
| 5 | — | Not applicable to commercial market. | 15 char | — |
| 6 | 5 | Subscriber's mailing address. The zip code of the subscriber's address. | 15 char | NM |
| 7 | 4 | Gender code. The gender for this CLI. | 1 char, enum | NM |
| 8 | 4 | Race code. The race identifier for this CLI. | 1 char, map | NM |
| 9 | 3 | Member's date of birth. The date of birth for the member on this CLI. The entry in this field is used to calculate the member's age. | 8 date yyyymmdd | M |
| 10 | 4 | Member status code. The entry in this field is used to identify members who will be analyzed. Once a study population is identified, each member should be assigned a value of 10 in this field. Otherwise, the ember will not be processed. | 2 char Field must = 10 for member to be processed | M |
| 11 | 1 | Referring provider identifier. Defines the provider that referred a member to another provider that generated the specific claim of interest. | 15 char | NM |
| 12 | 5 | Procedure code year. The year that a specific CPT-4, HCPCS, UB-92, or ICD.9 procedure code was used on a claim. | 1 char | NM |
| 13 | — | Not applicable to commercial market. | 3 char | — |
| 14 | — | Not applicable to commercial market. | 20 char | — |
| 15 | 1 | Performing provider identifier. This field refers to the provider that billed for the specific CLI. | 15 char | M |
| 16 | 4 | Provider type code. The type of billing entity that delivered the service for this CLI. | 1 char, map | M |
| 17 | 4 | Physician specialty code. The specialty under which the physician or other health care professional delivered the service for this CLI when delivered for payment. | 2 char, map | M |
| 18 | — | Not applicable to commercial market. | 1 char | — |
| 19 | — | Not applicable to commercial market. | 1 char | — |
| 20 | 2 | Line item service count. The number of services performed on a specific CLI. | 4 char | M |
| 21 | — | Not applicable to commercial market. | 1 char | — |
| 22 | 4 | Place of service code. The place where the unique service of this line item was rendered to the patient. | 2 char, map | M |
| 23 | 3 | Claim line item (CLI) start date. This field refers to the date of the first service on a CLI | 8 date yyyymmdd | M |
| 24 | 3 | CLI end date. Date of last service on a CLI. | 8 date yyyymmdd | M |
| 25 | 5 | Procedure code. The specific CPT-4, HCPCS, ICD.9 procedure, UB-92, and other procedure codes used to identify a specific service. | 5 char | M |
| 26 | 5 | Initial procedure code modifier. Used to add an initial modifier to a procedure code. | 2 char | NM |
| 27 | 5 | Second procedure code modifier. This field is used to add a second modifier to a procedure code. | 2 char | NM |
| 28 | 4 | BETOS Code. Every CLI processed by the system expect those submitted on UB-92 forms must have a BETOS code. | 3 char | M |
| 29 | 5 | National drug code. The national drug code (NDC) that identifies a specific prescription drug by product name, formulation, and quantity. | 11 char | NM |
| 30 | — | Not applicable to commercial market. | 7 char | — |
| 31 | 2 | Allowed charge amount. The allowed charge amount, often referred to the covered charge amount. Allowed charges typically equal submitted charges minus ineligible charges and discounts. They include (are the sum of) paid, copay/deductible/coinsurance, and COB. | 10 char | M |
| 32 | — | Not applicable to commercial market. | 2 char | — |
| 33 | — | Not applicable to commercial market. | 1 char | — |
| 34 | 5 | CLI diagnosis code. The primary ICD.9 diagnosis code on a CLI. | 5 char | M |
| 35 | 4 | Detailed grouping code. A detailed grouping code is a client-specified identifier that is the base data element | 15 char | NM |

TABLE 1-continued

CLI Mapping Code Fields

| Field Number | Type | Name & Description | Format | Mandatory or Non-mandatory |
|---|---|---|---|---|
| | | aggregated together to form a report group. For example, zip codes or tax identification numbers could be detailed grouping codes. | | |
| 36 | 5 | Secondary CLI diagnosis code. The secondary ICD.9 diagnosis code on a CLI. | 5 char | NM |
| 37 | 5 | Tertiary CLI diagnosis code. The tertiary ICD.9 diagnosis code on a CLI. | 5 char | NM |

Provider type codes (Field 16) identify the type of billing entity that delivered a service to a patient. The defined provider types are: none, physician, facility, pharmacy, independent service provider, and other. For none, no provider type is identified. Physicians are professionals delivering medical care services, not just physicians. This provider type includes physicians, chiropractors, acupuncturists, podiatrists, nurse practitioners, physical therapists, and other professionals delivering medical care services. Facility includes hospital inpatient, hospital outpatient, long term nursing homes, intermediate nursing homes, skilled nursing homes, rehabilitation facilities, end-stage renal disease facilities, and similar facilities. Pharmacy includes walk-in or mail-order pharmacies. This provider type is used by the present invention to identify the use of a prescription drug. Independent service providers include providers that are not associated with a facility or a physician's office, such as independent laboratories and imaging centers. Typically, an independent service provider delivers services that, depending on physician office capabilities, could be provided in a physician's office directly. Other is healthcare services such as durable medical equipment providers, medical supply providers, ambulance, home meal delivery, and other similar providers. Table 2 shows the provider type codes.

TABLE 2

Provider Type Codes

| Provider Type | Code |
|---|---|
| None | 0 |
| Physician | 1 |
| (This value is not applicable to commercial populations.) | 2 |
| Facility | 3 |
| Pharmacy | 4 |
| Independent service provider | 5 |
| Other | 6 |

Table 3 shows physician specialty codes (Field 17).

TABLE 3

Physician Specialty Codes

| Specialty | Code |
|---|---|
| None (Use this code when physician is not the provider type) | 0 |
| Allergist | 1 |
| Allied Practitioner | 2 |
| Anesthesiology | 3 |
| Anesthesiology Assistant | 4 |
| Cardiology | 5 |
| Cardiothoracic surgery | 6 |
| Chiropractor | 7 |

TABLE 3-continued

Physician Specialty Codes

| Specialty | Code |
|---|---|
| Dermatology | 8 |
| Emergency Medicine | 9 |
| Endocrinology | 10 |
| Family/General Practice | 11 |
| Gastroenterology | 12 |
| General Internist | 13 |
| General surgery | 14 |
| Genetic | 15 |
| Infectious Disease | 16 |
| Neonatal Care | 17 |
| Nephrology | 18 |
| Neurology | 19 |
| Neurosurgery | 20 |
| Obstetrician/Gynecologist | 21 |
| Oncology/Hematology | 22 |
| Ophthalmology | 23 |
| Optometry | 24 |
| Oral-maxillofacial Surgeon | 25 |
| Orthopedist | 26 |
| Otolaryngology (ENT) | 27 |
| Pain management | 28 |
| Pathology | 29 |
| Pediatrics | 30 |
| Plastic surgery | 31 |
| Podiatry | 32 |
| Psychiatry | 33 |
| Psychologist | 34 |
| Psychology Professional (e.g., social worker) | 35 |
| Pulmonology | 36 |
| Radiology | 37 |
| Rheumatology | 38 |
| Sports and physical medicine | 39 |
| Urology | 40 |
| Vascular surgeon | 41 |
| Critical care | 42 |
| Other | 99 |

The place of service code identifies where a unique service was provided to a patient (e.g., office, outpatient facility of a hospital, inpatient facility of a hospital). Table 4 shows the place of service codes (Field 22)

TABLE 4

Place of Service Codes

| Place of Service | Code | Description |
| --- | --- | --- |
| None | 0 | No place of service code or unknown place of service. |
| Office | 1 | Service delivered in a physician's office. |
| Home | 2 | Service delivered in a patient's home environment. |
| Emergency room | 3 | Service delivered in the emergency room department of a hospital. |
| Urgent care facility | 4 | Service delivered in an urgent care facility. |
| Inpatient hospital | 5 | Inpatient service delivered in a hospital. |
| Outpatient hospital | 6 | Outpatient service delivered in a hospital. |
| Ambulance | 7 | Service delivered in a land, air or water ambulance. |
| Ambulatory surgical center | 8 | Service delivered in a walk-in surgical center. |
| Birthing center | 9 | Service delivered in a birthing center. |
| Military treatment facility | 10 | Service delivered in a military treatment facility. |
| Inpatient psychiatric facility | 11 | Service delivered on an inpatient basis at a psychiatric facility for mental health or chemical dependency. |
| Public health clinic | 12 | Service delivered in a state or local public health clinic or a rural health clinic. |
| Independent laboratory | 13 | Service delivered at an independent laboratory. |
| Alternative care facility | 14 | Service delivered in an alternate care facility such as a skilled nursing facility, nursing facility, custodial care facility, hospice, adult living care facility (ACLF), psychiatric facility partial hospitalization, community mental health center, intermediate care facility/mentally retarded, residential substance abuse treatment facility, psychiatric residential treatment center, comprehensive inpatient rehabilitation facility comprehensive outpatient rehabilitation facility, end stage renal disease treatment facility, or similar facilities. |
| Other ambulatory facility | 15 | Service delivered in a walk-in environment such as a school, homeless shelter, health center, immunizations center, or similar facility. |
| Mobile unit | 16 | Service delivered in a unit that brings specific services to communities. |
| Other | 17 | Other places of service not included in the types listed in this table. |
| Pharmacy | 18 | Indicates that the prescription drug was dispensed by a walk-in or mail-order pharmacy. This includes hospital-run pharmacies that may dispense prescription drugs on an outpatient basis. |

Type of Service (BETOS) Codes (Field 28)

In an embodiment, the present invention uses BETOS (Berenson-Eggers type of service) Codes as the type of service code (Field 28). The BETOS Code system is a procedure code system that organizes procedures and services into groupings that have been generally accepted as clinically meaningful. The BETOS Code system categories allow objective assignment of procedures and services. A BETOS Code must be assigned for each service on a CLI (e.g., CPT-4, HCPCS), except those submitted on UB-92 forms. Any homegrown codes or other special service codes that do not have BETOS Code must be mapped to a specific BETOS Codes.

In an embodiment, the present invention groups all health services with a BETOS Code into one of 11 service categories. Moreover, an embodiment of the present invention also groups all health services with a BETOS Code into one of 21 sub-service categories. Services without a BETOS Code will be assigned to our other medical services category. In an embodiment, alternative CLI health services grouping system may be applied other than BETOS codes.

The services provided during an episode of care are separated into the following 11 service categories and 21 sub-service categories presented below.

Category 0 is the overall results in the output files. The overall results are normally presented in the 0 row or the 0 section of the output file. This category captures the overall information for a physician. In an embodiment, the present invention calculates overall charges, but does not calculate overall utilization. As a result, the overall utilization entry 0 row is used to present the average duration (in days).

The professional visits (prof visits) service category presents charges and utilization for professional visits incurred in the physician's office, clinic or outpatient department of a hospital. For utilization, the numerator unit is visits. The sub-service category also is professional visits. This sub-service category presents charges and utilization for professional visits incurred in the physician's office, clinic, or outpatient department of a hospital.

The diagnostic tests (diag tests) service category presents charges and utilization for diagnostic tests incurred in the physician's office, clinic, outpatient department of a hospital, or surgicenter. Diagnostic tests represent imaging tests (X-rays, CAT scans, MRIs, etc.), functional tests (EKGs, echocardiograms, etc.), and invasive tests. There are three sub-service categories for diagnostic testing. The first sub-service category is imaging tests. This sub-service category presents charges and utilization for imaging tests, which include x-rays, CAT scans, MRI, and other related imaging tests. For utilization the numerator unit is services or tests. The second sub-service category is invasive testing. This sub-service category presents charges and utilization for angiography, cardiac catheterization, myocardial imaging, myelography, and other related invasive testing. For utilization, the numerator unit is services or tests. The third sub-service category is functional testing. This sub-service category presents charges and utilization for electrocardiograms, cardiovascular stress tests, echography, and other related functional testing. For utilization, the numerator unit is services or tests.

The laboratory and pathology (lab/path) service category presents charges and utilization for laboratory and pathology services incurred in the physician's office, clinic, outpatient department of a hospital, or surgicenter. For utilization, the numerator unit is services. There are two sub-service categories. The first sub-service category is laboratory (lab). This sub-service category presents charges and utilization for laboratory services incurred in the physician's office, clinic, outpatient department of a hospital, or surgicenter. For utilization, the numerator unit is services. The second sub-service category is pathology (path). This sub-service category presents charges and utilization for pathology services incurred in the physician's office, clinic, outpatient department of a hospital, or surgicenter. For utilization, the numerator unit is services.

The medical and surgical procedures (med/surg) service category presents charges and utilization for medical and surgical procedures incurred in the physician office, clinic, outpatient department of a hospital, and surgicenter. For utilization, the numerator unit is services or procedures. There are two sub-service categories. The first sub-service category is medical (med). This sub-service category presents charges and utilization for ophthalmological services (including eye exams), electro-oculography, otolaryngologic exam, evaluation of speech/voice, cardiac rehabilitation, muscle testing, neurobehavioral exams, and related medical procedures. For utilization, the numerator unit is services or procedures. The second sub-service category is surgical (surg). This sub-service category presents charges and utilization for surgical procedures incurred in the physician office, clinic, outpatient department of a hospital, or surgicenter. For utilization, the numerator unit is services or procedures.

The prescription drugs (Rx) service category presents charges and utilization for outpatient and ambulatory prescription drugs. For utilization, the numerator unit is prescription drug fills. The sub-service category also is prescription drugs. This sub-service category presents charges and utilization for outpatient and ambulatory prescription drugs.

The professional inpatient services (prof inpt) service category presents charges and utilization for all inpatient professional services. For utilization, the numerator unit is services. The sub-service category also is inpatient professional.

The facility outpatient visits (outpt facility) service category presents charges and utilization for services incurred in an outpatient department of a hospital or surgicenter. For utilization, the numerator unit is visits. There are two sub-service categories. The first sub-service category is emergency room facility. This sub-service category presents charges and utilization for emergency room facility services. For utilization, the numerator unit is visits. The second sub-service category is other outpatient facility. This sub-service category presents charges and utilization for other outpatient facility services, including medical/surgical, rehabilitation, and other services incurred in an outpatient department of a hospital or surgicenter. For utilization, the numerator unit is visits.

The facility inpatient days (hosp inpt days) service category presents charges and utilization for inpatient days for all hospital inpatient facility services. For utilization, the numerator unit is hospital inpatient days. The sub-service category also is inpatient facility days.

The facility inpatient admissions (hosp inpt admits) service category presents utilization for admissions for all hospital inpatient facility services. For utilization, the numerator unit is admissions. Charges are not presented for this service category. For charges, this service category is entered as "0," because the episode charge component is assigned to the Facility Inpatient Days service category. The sub-service category also is inpatient facility admissions.

The alternative sites (altern sites) service category presents charges and utilization for skilled nursing facility and half-way home services. For utilization, the numerator unit is services. The sub-service category also is alternative sites.

The other medical services (other med) service category presents charges and utilization for other professional medical services incurred in the physician's office, clinic, outpatient department of a hospital, and dialysis center. Other medical services include physical therapy, chiropractic services (other than professional visits), chemotherapy and radiation, dental, durable medical equipment, and ambulance services. For utilization, the numerator unit is services. There are six sub-service categories. The first sub-service category is physical therapy. This sub-service category presents charges and utilization for manual therapy, electric simulation and other modalities, orthotics training, prosthetic training, and related physical therapy services. For utilization, the numerator unit is services.

The second sub-service category is dialysis. This sub-service category presents charges and utilization for end-stage renal disease (ESRD), hemodialysis, hemoperfusion, and related dialysis services. For utilization, the numerator unit is services. The third sub-service category is chemo/radiology. This sub-service category presents charges and utilization for chemotherapy administration, provision of chemotherapy agents, radiation dosimetry, brachytherapy isodose plans, radiation treatment delivery, and other related chemo/radiation services. For utilization, the numerator unit is services. The fourth sub-service category is anesthesia. This sub-service category presents charges and utilization for anesthesia. For utilization, the numerator unit is services. The fifth sub-service category is durable medical equipment (DME). This sub-service category presents charges and utilization for crutches, walkers, commode chairs, pressure pads, beds, portable oxygen, breast pumps, infusion supplies, wheelchairs, and related DME services. For utilization, the numerator unit is services. The sixth sub-service category is other medical care. This sub-service category presents charges and utilization for other medical care not easily classified elsewhere (e.g., ambulance, influenza immunization, dental not classified elsewhere). For utilization, the numerator unit is services.

Step 1. Build Flattened CLI Structure Input File

The traditional structure of CLI input files is hierarchical. In a hierarchical structure, there is a family (or subscriber) unit, and the individual members within the family are associated with the family unit. Then, the claim submissions for a member are associated to the member. This claim record generally contains information such as provider ID, provider specialty type, name of provider, and place of service. Finally, the CLIs within a claim are associated with the particular claim. The CLIs generally contain the detailed record information of each individual service rendered by the healthcare provider (e.g., CPT-4 code, ICD.9 (diagnosis) codes, number of services provided, service start and end dates).

Therefore, in a hierarchical structure, there are at least four different record types: family, member, claim, and CLI.

An advantage of the hierarchical structure is that it gives the user one data file, which generally is easy to manage. Furthermore, this structure is intuitive, as the structure is generally how claims processors at health plans think about organizing the submitted claims data.

The disadvantage of the hierarchical structure is that reading the records from the claim input file into the software takes significantly more CPU requirements as compared to the flattened CLI structure employed in embodiments of the present invention. Therefore, the hierarchical structure requires significantly higher software system processing time.

For the flattened CLI structure, there is only one record type produced for each CLI. Moreover, all records in the file are the exact same type and format. Therefore, each record forms a block that consists of a given number of the exact same bytes.

The flattened CLI structure contains all record field information that is present in the hierarchical CLI structure. Therefore, CLI records from members in the same family need to contain repeating family, member, and some unique claim information. On the surface, one may think that the repetition of family, member, and claim field variables on each CLI record will form a larger data file as compared to the hierarchical CLI structure.

However, this is not the case because the hierarchical CLI structure requires a 'marker' after each record to signify the start of another record. For example, in an embodiment, a marker is needed to signify that the family record information has ended and the member information begins; a marker is needed to signify that the member information has ended and the claim information begins; and a marker is needed to signify that the claim information has ended and the first CLI information for the claim begins.

Another issue with the hierarchical CLI structure is that the number of subordinate blocks of data is variable and, therefore, separate markers must be used to encode this information. For example, a family may have from one to N number of family members. Likewise, a single member may have from one to N number of claims, and a claim may have from one to N number of CLIs. In each of these cases, some type of encoding marker must be used to include this information into the data file. Additional CPU time is used in the software to read and handle these additional markers.

The volume of required markers within the hierarchical CLI structure makes the data file size similar to that of the flattened CLI structure.

The advantage of the flattened CLI structure is that the data file is easily read into a medical claims-based software, requiring significantly less CPU requirements as compared to a hierarchical CLI structure. The reason for less CPU intensive record reading is that computers like to read fixed length records of the same type and format (i.e., blocks of data). The overall read step processing time, then, is significantly reduced.

Step 2: Read in RUN.INI File

The operation of the system of the present invention is influenced by parameters. Parameters are named controls found within the system of the present invention run initialization file (or RUN.INI File). Controls influence the results generated by the system of the present invention. Table 6 presents the parameters in the RUN.INI file.

TABLE 6

Parameters in the RUN.INI File

| Parameter Name | Notes | Values |
|---|---|---|
| Module Control Programs | | |
| RUN_PATAN | Controls whether the PATAN module is executed during the current run. | 0 = No<br>1 = Yes<br>Initial System setting = 1 |
| RUN_PROVSPEC | Controls where the PROVSPEC module is executed during the current run. | 0 = No<br>1 = Yes<br>Initial System setting = 1 |
| RUN_PROVAN | Controls whether the PROVAN module is executed during the current run. | 0 = No<br>1 = Yes<br>Initial System setting = 1 |
| General Directory Parameters | | |
| DIR_BIN | Defines the location of program files. | Directory path |
| DIR_SYSTABLE | Defines the location of system methodology tables (see the 'Control Tables" section of this manual). | Directory path |
| DIR_DATA | Defines the root directory for all data files, both input and output. | Directory path |
| DIR_RUNTABLE | Defines the location of both data-specific tables and pre-specified tables (see the "Control Tables" section of this manual). | Directory path |
| FILE_PROVIDER | Defines the location of the physician specialty file (see the "Data-Specific Tables" section of this manual). | File Name |
| FILE_GROUPCODEMAP | Defines the detail grouping code to the aggregate grouping code. | File Name |
| Module Runtime Parameters<br>Grouper function | | |
| SWITCH_AGGREGATESTART | Defines the start number for the Aggregate Grouping Codes to be processed. For more information on Aggregate Grouping Codes see the chapter, "Report Group Structures". NOTE: Leave the value of this switch at 0 unless you want to limit the groups to be processed. | 0 = Do not eliminate any Aggregate Grouping Codes from the beginning of the list<br>N (any whole number) = Specifies the first Aggregate Grouping Code to be processed. All codes |

TABLE 6-continued

Parameters in the RUN.INI File

| Parameter Name | Notes | Values |
| --- | --- | --- |
| | | that are smaller than this value will not be processed<br>Initial System setting = 0 |
| SWITCH_AGGREGATEEND | Defines the end number of the Aggregate Grouping Codes to be processed. For more information on Aggregate Grouping Codes see the chapter, "Report Group Structures." | 0 = Do not eliminate any Aggregate Grouping Codes from the end of the list<br>N (any whole number) = Specifies the last Aggregate Grouping Code to be processed. All codes that are larger than this value will not be processed.<br>Initial System setting = 0 |
| FILE_SPECAGE | Identifies the file containing the age control table for each specialty. | File Name with respect to DIR_RUNTABLE<br>Initial System setting = specage.tab |
| FILE_MBCONDITIONS | Identifies the file that relates medical conditions to classifications in accordance with the present inventions. | File Names with respect to DIR_RUNTABLE<br>Initial System setting = mbconditions.tab |
| | PATAN | |
| SWITCH_DROPPARTIAL | Controls whether partial episodes are included in analysis. | 0 = Include<br>1 = Exclude<br>Initial System setting = 1 |
| SWITCH_DROPCOMORB | Controls whether comorbid episodes are included in analysis. | 0 = Include<br>1 = Exclude<br>Initial System setting = 1 |
| SWITCH_ASSIGNTHRESHOLD | Defines a percent whereby when a physician has this percent or more of total professional charges associated with an episode, that episode is assigned to the physician. The professional charges considered for this threshold may occur in an office visit, clinic, hospital outpatient, hospital inpatient, or other professional setting (e.g., nursing home, halfway home, home visit professional charges). All facility charges and prescription drug charges are excluded. | Any whole number representing a percent<br>Initial System setting = 20 |
| | PROVSPEC | |
| | NONE | |
| | PROVAN | |
| SWITCH_LOWOUTPERCENT | Defines what percentage of a physician's least expensive episodes will be removed from analysis. PROVAN removes episodes from each medical condition in the physician's marketbasket separately. PROVAN starts with the least expensive episode and continues removing episodes in order of expense until the specified percentage of episodes is reached. | 0 = 0.0%<br>1 = 1.0%<br>2 = 2.5%<br>3 = 5.0%<br>4 = 10.0%<br>Initial System setting = 2 |
| SWITCH_LOWOUTDOLLAR | Sets a threshold for episode charges. All episodes below the value of this switch will be dropped from analysis. | A whole number representing a dollar value.<br>Initial System setting = 20 |
| SWITCH_HIGHOUTPERCENT | Defines what percentage of a physician's most expensive episodes will be removed from analysis. PROVAN removes episodes from each medical condition in the physician's marketbasket. PROVAN starts with the most expensive episode and continues removing episodes in order of expense until the specified percentage of episodes is reached. | 0 = 0.0%<br>1 = 1.0%<br>2 = 2.5%<br>3 = 5.0%<br>4 = 10.0%<br>Initial System setting = 3 |
| SWITCH_HIGHOUTDIFF | The parameter SWITCH_HIGHOUTDIFF determines whether a signal episode should be removed as a high-outlier. This high-end outlier parameter is applied when one high-end outlier cannot be removed under the SWITCH_HIGHOUTPERCENT parameter. The value of this parameter is a whole number representing a percent. If the charges for the most expensive episode are | A whole number that represents a percent.<br>NOTE: Should always be ≥100. If ≤100, then an episode will ALWAYS be removed.<br>Initial System setting = 250 |

TABLE 6-continued

Parameters in the RUN.INI File

| Parameter Name | Notes | Values |
| --- | --- | --- |
| | at least the defined percent greater than the charges for the next most expensive episode, the most expensive episode is removed as a high outlier. A maximum of one episode for each medical condition in each physician's marketbasket may be removed using this rule. | |
| SWITCH_MINEPCOUNT | Sets the requirement for the number of episodes a physician must treat to be included in the analysis. This parameter implements part of the N × 3 rule, which specifies that a physician must treat N episodes in three medical conditions to be included. For example, if the N value is equal to four, the rule would require four episodes in each of three conditions, and the rule would become, in effect a "4 × 3" rule. In the N × 3 rule: N = The number of episodes of a specific medical condition a physician must treat during the study period. This number can be changed by the user. 3 = the minimum number of medical conditions in which the physician must treat episodes. The medical conditions must be in the physician's marketbasket. This number cannot be changed. | Any whole number Initial System setting = 2 |
| SWITCH_CONFLEVEL | Sets the p value for statistical confidence. | 1 = 0.75 ($p < 0.25$) 2 = 0.90 ($p < 0.10$) Initial System setting = 1 |

PATAN Date Parameters

| Parameter Name | Notes | Values |
| --- | --- | --- |
| STUDYSTARTDATE | Defines the start date of the study period. | A date in the format yyyymmdd |
| STUDYENDDATE | Defines the end date of the study period. | A date in the format yyyymmdd |
| STUDYMIDDATE | Sets the midpoint date of the study period. A chronic episode of care must start on or before this date. | A date in the format yyyymmdd |
| STUDYQ4DATE | Defines the date that is the end of the third quarter of the study period (the last day before the fourth quarter starts). An acute episode of care from a medical condition with a window period ≥120 days must start on or before this date. | A date in the format yyyymmdd |

Slider Parameters

| Parameter Name | Notes | Values |
| --- | --- | --- |
| STUDYSLIDER1_START | Sets the start date of the slider period for Slider 1. | A date in the format yyyymmdd |
| STUDYSLIDER1_END | Sets the end date of the slider period for Slider 1. | A date in the format yyyymmdd |
| STUDYSLIDER2_START | Sets the start date of the slider period for Slider 2. | A date in the format yyyymmdd |
| STUDYSLIDER2_END | Sets the end date of the slider period for Slider 2. | A date in the format yyyymmdd |

Module Runtime Output Directory Parameters - Within DIR_DATA

| Parameter Name | Notes | Values |
| --- | --- | --- |
| DIR_PATSORT | Identifies the subdirectory that receives the PATSORT output. This subdirectory is within the DIR_DATA directory path. | Directory name Initial System setting = patsort |
| DIR_PATAN | Identifies the subdirectory that receives the PATAN output. This subdirectory is within the DIR_DATA directory path. | Directory name Initial System setting = patan |
| DIR_PROVSORT1 | Identifies the subdirectory that receives the PROVSORT1 output. This subdirectory is within the DIR_DATA directory path. | Directory name Initial System setting = provsort1 |
| DIR_PROVSPEC | Identifies the subdirectory that receives the PROVSPEC output. This subdirectory is within the DIR_DATA directory path. | Directory names Initial System setting = provspec |
| DIR_PROVSORT2 | Identifies the subdirectory that receives the PROVSORT2 output. This subdirectory is within the DIR_DATA directory path. | Directory name Initial System setting = provsort2 |

TABLE 6-continued

Parameters in the RUN.INI File

| Parameter Name | Notes | Values |
|---|---|---|
| DIR_PROVAN | Identifies the subdirectory that receives the PROVAN output. This subdirectory is within the DIR_DATA directory path. | Directory name<br>Initial System setting = provan |
| | Data file Parameters - within DIR_DATA | |
| COREFILE | Defines the subdirectory and filename that contains the input claims file. The subdirectory is within the DIR_DATA directory path. | Directory name/File name<br>Initial System setting = extract/corefields |
| CORESORTED | Defines the subdirectory and filename that contains the sorted claims file. The subdirectory is within the DIR_DATA directory path. | Directory name/File name<br>Initial System setting = patsort/sampledata.sort |
| ASNFILE | Defines the subdirectory and filename that contains the output file from PATAN. The subdirectory is within the DIR_DATA directory path. | Directory name/File name<br>Initial System setting = patan/assign.tab |
| ASNSORTED | Defines the subdirectory and filename that contains the sorted output file from PATAN. The subdirectory is within the DIR_DATA directory path. | Directory name/File name<br>Initial System setting = provsort1/assign.tab.sort |
| ASNSPECFILE | Defines the subdirectory and filename that contains the output file from PROVSPEC. The subdirectory is within the DIR_DATA directory path. | Directory name/File name<br>Initial System setting = provspec/assignspec.tab |
| ASNSPECSORTED | Defines the subdirectory and filename that contains the sorted output file from PROVSPEC. The subdirectory is within the DIR_DATA directory path. | Directory name/File name<br>Initial System setting = provsort2/assignspec.tab.sort |
| SCOREFILE | Defines the subdirectory and filename that contains one of the two final output files. The subdirectory is within the DIR_DATA directory path. | Directory name/File name<br>Initial System setting = provan/score.tab |
| DETAILFILE | Defines the subdirectory and filename that contains one of the two final output files. The subdirectory is within the DIR_DATA directory path. | Directory name/File name<br>Initial System setting = provan/detail.tab |

Step 3: Read in CLIs from Flattened CLI Structure

The CLIs in the Flattened CLI Structure are now read into the patient sort (PATSORT). PATSORT sorts CLIs by the primary sort key of member (or patient) and the secondary sort key of date of service on each CLI. During PATSORT, all CLIs with zero dollars in charges ($0) are removed from further analysis.

Step 4: Apply Sliders

An embodiment of the present invention uses sliders to establish that a member was present during an ongoing condition-specific episode of care. The purpose of sliders is to establish the presence of members during ongoing condition-specific episodes of care without using an eligibility file. Often, membership eligibility files are not readily accessible to the user.

An embodiment of the present invention employs two sliders, each of which can be set with a start date and an end date. These dates can be set by the user. The period that includes the start and end dates and the time in between is the slider period. The use of sliders allows the user to establish that a member was present at least for some period of time near the beginning and near the end of the study period. If so, then the user concludes that the member was present during the ongoing condition-specific episode of care.

An embodiment of the present invention checks to see that the member was represented by a CLI that began and ended during each slider period. If not, then the member and all CLIs related to that member are removed from the analysis.

The two sliders are referred to herein as Slider 1 and Slider 2. Slider period settings for a calendar year study period are as follows: Slider 1 is set for the time period of January 1 through June 30. (If not using a calendar year, then use the first six months of the study period.) Slider 2 is set for the time period of July 1 through December 31. (If not using a calendar year, then use the second six months of the study period.) With these settings, a member must have a claim in both the first and second halves of the year to be included in the analysis.

Table 7 illustrates examples of suggested slider settings for a study period that starts on January 1 and ends on December 31.

TABLE 7

Recommended Slider Settings

| Example # | Slider Settings | Notes |
|---|---|---|
| 1 | Slider period 1: January 1 through June 30 | With these settings, a member must have one final adjudicated claim in each slider period to be included in the |

TABLE 7-continued

Recommended Slider Settings

| Example # | Slider Settings | Notes |
|---|---|---|
| | Slider period 2: July 1 through December 31 | analysis. These settings increase the likelihood that a member included in the analysis was in fact present during an ongoing episode of care. |
| 2 | Slider period 1: March 1 through December 31 Slider period 2: March 1 through December 31 | A member who has one final adjudicated claim during slider period 1 is assumed to be present during the entire year. Slider 2 is ignored because its slider period is identical to Slider 1's period. This setting keeps many members in the analysis. |

Step 5: Perform PATAN Analysis to Form Episodes of Care

The Patient Analysis (PATAN) forms episodes of care using a Grouper function explained herein. The Grouper function is based on the International Classification of Diseases, 9$^{th}$ revision (ICD.9) and the Current Procedural Terminology, 4$^{th}$ edition (CPT-4). The Grouper function groups together over 14,000 unique ICD.9 diagnosis codes into 526 meaningful medical conditions. Each ICD.9 code is assigned to a single medical condition.

The resulting 526 medical conditions are formed based on clinical homogeneity with respect to generating a similar clinical response from physicians treating a patient. Table M shows selected ICD.9 codes mapped to several medical conditions.

TABLE M

Selected Diagnosis (ICD.9) Codes Mapped to Medical Conditions

| Medical Condition Number | Medical Condition Long Description | ICD.9 Codes | Brief Description |
|---|---|---|---|
| 5.2 | Conjunctivitis | 077.0 | Conjunctivitis, inclusion |
| | | 077.8 | Conjunctivitis, viral |
| | | 372.0 | Conjunctivitis, acute |
| | | 372.01 | Conjunctivitis, serous |
| | | 372.1 | Conjunctivitis, chronic |
| | | 372.14 | Conjunctivitis chronic allergic |
| | | 372.22 | Contact blepharonconjunctivitist |
| 6.5 | Otitis media | 381 | Eustachian tube disorder |
| | | 381.02 | Acute mucoid otitis media |
| | | 381.06 | Acute allergic sanguinous otitis media |
| | | 381.20 | Chronic mucoid otitis media |
| | | 382 | Suppurative otitis media |
| | | 382.00 | Acute suppurative otitis media |
| | | 382.4 | Suppurative otitis media |
| | | 382.01 | Acute suppurative, with drum rupture |
| | | 382.1 | Chronic tubotympanic suppurative |
| 7.2 | Sinusitis | 461.0 | Acute maxillary sinusitis |
| | | 461.2 | Acute ethomoidal sinusitis |
| | | 461.3 | Acute sphenoidal sinusitis |
| | | 473 | Chronic sinusitis |
| | | 473.2 | Chronic ethmoidal sinusitis |
| | | 473.3 | Chronic sphenoidal sinusitis |
| 9.11 | Asthma | 493.0 | Extrinsic asthma |
| | | 493.02 | Extrinsic asthma, acute exacerbation |
| | | 493.1 | Intrinsic asthma |
| | | 493.01 | Extrinsic asthma, status asthmaticus |
| | | 493.2 | Chronic obstructive asthma |
| | | 493.21 | Chronic obstructive, status asthmaticus |
| 10.2 | Hypertension | 401.1 | Benign essential hypertension |
| | | 405.1 | Secondary benign hypertension |
| | | 402 | Hypertensive heart disease |
| | | 402.0 | Hypertensive heart disease, malignant |
| | | 403.00 | Hypertension renal, malignant |
| | | 403.1 | Hypertension renal, benign disease |
| | | 405.0 | Secondary malignant hypertension |
| | | 402.11 | Hypertensive heart, malignant, heart failure |
| | | 404.01 | Hypertensive heart/renal, malignant health failure |
| | | 404.11 | Hypertensive heart/renal, benign, heart failure |

The 526 medical conditions are placed into one of 37 Principle Medical Condition Groups (PMC Groups). The PMC Groups generally represent organ, body, or medical condition types (e.g., PMC Group 5-Eye Conditions; PMC Group 9-Respiratory Conditions; PMC Group 24-Mental Disorders). Table 8 presents the list of PMC Groups.

TABLE 8

Principle Medical Condition (PMC) Groups

| Principle Medical Condition Groups | PMC Group Long Description | PMC Group Abbreviated Description |
|---|---|---|
| 1 | Preventive Care | Preventive Care |
| 2 | Infectious and Parasitic Diseases | Infectious & Parasitic Dz |
| 3 | Human Immunodeficiency Infections | HIV Infections |
| 4 | Nervous System Conditions | Nervous System Conditions |
| 5 | Eye Conditions | Eye Conditions |
| 6 | Ear Conditions | Ear Conditions |
| 7 | Nose Conditions | Nose Conditions |
| 8 | Mouth Conditions | Mount Conditions |
| 9 | Respiratory Conditions | Respiratory Conditions |
| 10 | Heart and Pulmonary Conditions | Heart and Pulmonary Cond |
| 11 | Cerebrovascular and Artery Conditions | Cerebrovasc & Artery Cond |
| 12 | Vein and Lymphatic Conditions | Vein & Lymphatic Cond |
| 13 | Digestive System Conditions | Digestive System Cond |
| 14 | Hernias | Hernias |
| 15 | Hepatobiliary System and Pancreas | Hepatobiliary Sys & Pancreas |
| 16 | Thyroid Disorders | Thyroid Disorders |
| 17 | Diabetes Mellitus | Diabetes Mellitus |
| 18 | Other Endocrine Disorders | Other Endocrine Disorders |
| 19 | Metabolic Disorders | Metabolic Disorders |
| 20 | Immunity and Blood Disorders | Immunity & Blood Disorders |
| 21 | Lymphatic and Hematopoietic Tissue | Lymph & Hematopoietic Tiss |
| 22 | Urinary Tract and Kidney Conditions | Urinary Tract & Kidney Cond |
| 23 | Female Reproductive Conditions | Female Reproductive Cond |
| 24 | Male Reproductive Conditions | Male Reproductive Cond |
| 25 | Infertility Treatment | Infertility Treatment |
| 26 | Maternity-Related Conditions | Maternity-Related Cond |
| 27 | Neonatal Conditions | Neonatal Conditions |
| 28 | Congenital Anomalies | Congenital Anomalies |
| 29 | Skin and Subcutaneous Tissue Conditions | Skin & Subcutaneous Tissue |
| 30 | Breast Conditions | Breast Conditions |
| 31 | Musculoskeletal Conditions | Musculoskeletal Conditions |
| 32 | Upper Limb Conditions | Upper Limb Conditions |
| 33 | Lower Limb Conditions | Lower Limb Conditions |
| 34 | Mental Disorders | Mental Disorders |
| 35 | Burns | Burns |
| 36 | Other Medical Conditions | Other Medical Conditions |
| 37 | Replaced Diagnosis Codes | Replaced Diagnosis Codes |

Within each PMC Group, medical conditions are listed in ascending order of expected resource intensity level and physiologic progression of the condition or disease (from least resource intensive and physiologic progression to the most resource intensive and physiologic progression). Table 9 shows an example for PMC Group 6, Ear Conditions.

TABLE 9

PMC Group 6-Ear Conditions

| Medical Condition Number | Medical Condition Long Description |
|---|---|
| 6 | Ear Conditions |
| 6.1 | Otitis externa |
| 6.2 | Wax in ear |
| 6.3 | Open wound of ear |
| 6.4 | Other disorders of ear |
| 6.5 | Otitis media |
| 6.6 | Disorders of tympanic membrane |
| 6.7 | Disorders of middle ear |
| 6.8 | Vertiginous syndromes |
| 6.9 | Mastoiditis |
| 6.10 | Hearing loss |
| 6.11 | Malignant neoplasm of middle ear |

The 526 medical conditions in the Grouper function account for 100% of all medical conditions and expenditures as identified by ICD.9 medical condition diagnostic codes. Each condition receives a Medical Condition Number (e.g., Medical Condition 4.1-neuritis upper and lower limbs; Medical Condition 5.16-glaucoma; Medical Condition 7.2-sinusitis; Medical Condition 9.11-asthma; Medical Condition 10.13-ischemic heart disease). Table 10 presents the list of medical conditions in the Grouper function.

TABLE 10

List of Medical Conditions in Grouper Function

| Medical Condition Number | Medical Condition Long Description | Medical Condition Abbrev Description | Number of Severity Classes |
|---|---|---|---|
| 1 | Preventive Care | Preventive Care | — |
| 1.1 | General medical exam | General medical exam | 1 |
| 1.2 | Gynecological exam | Gynecological exam | 1 |
| 1.3 | Screenings for medical conditions | Screening of med conditions | 1 |
| 1.4 | Vaccinations | Vaccinations | 1 |
| 1.5 | Prophylactic therapy | Prophylactic therapy | 1 |
| 1.6 | History of medical conditions | Hx of medical conditions | 1 |
| 1.7 | Postpartum exam | Postpartum exam | 1 |
| 1.8 | Surgical aftercare | Surgical aftercare | 1 |
| 2 | Infectious and Parasitic Diseases | Infectious & Parasitic Dz | — |
| 2.1 | Intestinal infections | Intestinal infections | 1 |
| 2.2 | Other bacteria disease | Other bacteria diseases | 3 |
| 2.3 | Drug-resistant microorganism | Drug-resistant microorganism | 1 |
| 2.4 | Septicemia | Septicemia | 2 |
| 2.5 | Tuberculosis | Tuberculosis | 3 |
| 2.6 | Other viral diseases | Other viral diseases | 3 |
| 2.7 | Chickenpox | Chickenpox | 3 |
| 2.8 | Herpes simplex | Herpes simplex | 3 |
| 2.9 | Viral warts | Viral warts | 1 |
| 2.10 | Infectious mononucleosis | Infectious mononucleosis | 1 |
| 2.11 | Cytomegalic inclusion disease | Cytomegalic inclusion dz | 1 |
| 2.12 | Non-arthropod-borne viral diseases | Non-arth-borne viral dz | 3 |
| 2.13 | Arthropod-borne diseases | Arthropod-borne dz | 3 |
| 2.14 | Venereal diseases | Venereal diseases | 3 |
| 2.15 | Other mycoses | Other mycoses | 1 |
| 2.16 | Cryptococcosis | Cryptococcosis | 1 |
| 2.17 | Candidiasis | Candidiasis | 3 |
| 2.18 | Coccidioidomycosis | Coccidioidomycosis | 3 |
| 2.19 | Histoplasmosis | Histoplasmosis | 3 |
| 2.20 | Blastomycotic infection | Blastomycotic infection | 2 |
| 2.21 | Helminthiases | Helminthiases | 3 |
| 2.22 | Scabies | Scabies | 1 |
| 2.23 | Toxoplasmosis | Toxoplasmosis | 3 |
| 2.24 | Pneumocystosis | Pneumocystosis | 1 |
| 2.25 | Other infectious diseases | Other infectious diseases | 3 |
| 3 | Human Immunodeficiency Infections | HIV Infections | — |
| 3.1 | HIV infection with no complications | HIV n/no complications | 1 |
| 3.2 | HIV infection with infectious complication | HIV with infectious comp | 3 |
| 3.3 | HIV infection with CNS involvement | HIV with CNS involvement | 3 |
| 3.4 | HIV infection with malignancy | HIV with malignancy | 3 |
| 3.5 | HIV infection with multiple complications | HIV with multiple comp | 3 |
| 4 | Nervous System Conditions | Nervous System Conditions | — |
| 4.1 | Neuritis upper and lower limbs | Neuritis upper, lower limbs | 2 |
| 4.2 | Peripheral neuropathy | Peripheral neuropathy | 3 |
| 4.3 | Headaches | Headaches | 2 |
| 4.4 | Disorders of cranial nerves | Disorders of cranial nerves | 2 |
| 4.5 | Carpal tunnel syndrome | Carpal tunnel syndrome | 1 |
| 4.6 | Benign neoplasm of non-CNS nerves | Benign neop non-CNS nerves | 1 |
| 4.7 | Nerve root and plexus disorder | Nerve root and plexus dsdr | 3 |
| 4.8 | Tremor disorders | Tremor disorders | 2 |
| 4.9 | Injury to peripheral nerves and nerve roots | Inj peripheral nerv & nerv roots | 3 |
| 4.10 | Neurofibromatosis | Neurofibromatosis | 1 |
| 4.11 | Inflammatory diseases of CNS | Inflammatory dz of CNS | 1 |
| 4.12 | Paralytic syndromes | Paralytic syndromes | 3 |
| 4.13 | Myoneural disorders | Myoneural disordes | 2 |
| 4.14 | Benign neoplasm of CNS | Benign neoplasm of CNS | 1 |
| 4.15 | Injury of spinal cord | Injury of spinal cord | 3 |
| 4.16 | Congenital anomalies of nervous system | Cong anomalies nerv sys | 3 |
| 4.17 | Parkinson's disease | Parkinson's disease | 1 |
| 4.18 | Seizure disorders | Seizure disorders | 3 |
| 4.19 | Multiple sclerosis | Multiple sclerosis | 1 |
| 4.20 | Other CNS diseases | Other CNS diseases | 3 |
| 4.21 | Muscular dystrophies | Muscular dystrophies | 2 |
| 4.22 | Malignant neoplasm of non-CNS nerves | Malig neop non-CNS nerves | 1 |
| 4.23 | Malignant neoplasm of spinal cord | Malig neop spinal cord | 1 |
| 4.24 | Malignant neoplasm of brain, initial care | Malig neop brain, initial | 1 |
| 4.25 | Malignant neoplasm of brain, active care | Malig neop brain, active | 1 |
| 4.26 | Malignant neoplasm of brain, inactive care | Malig neop brian, inactive | 1 |
| 5 | Eye Conditions | Eye Conditions | — |
| 5.1 | Refractive errors | Refractive errors | 1 |
| 5.2 | Conjunctivits | Conjunctivitis | 2 |
| 5.3 | Other disorders of conjunctiva | Other dsdr of conjunctiva | 2 |
| 5.4 | Infections of the eyelids | Infections of the eyelids | 2 |
| 5.5 | Disorders of eyelids | Disorders of eyelids | 2 |

TABLE 10-continued

List of Medical Conditions in Grouper Function

| Medical Condition Number | Medical Condition Long Description | Medical Condition Abbrev Description | Number of Severity Classes |
|---|---|---|---|
| 5.6 | Disorders of lacrimal system | Dsdr of lacrimal system | 2 |
| 5.7 | Keratitis | Keratitis | 3 |
| 5.8 | Other disorders of cornea | Other disorders of cornea | 3 |
| 5.9 | Disorders of iris and ciliary body | Dsdr iris and ciliary body | 3 |
| 5.10 | Strabismus | Strabismus | 3 |
| 5.11 | External eye injury | External eye injury | 2 |
| 5.12 | Disorders of globe | Disorders of globe | 3 |
| 5.13 | Internal eye injury | Internal eye injury | 2 |
| 5.14 | Disorders of vitreous body | Disorders of vitreous body | 2 |
| 5.15 | Other eye disorders | Other eye disorders | 3 |
| 5.16 | Glaucoma | Glaucoma | 3 |
| 5.17 | Cataract | Cataract | 3 |
| 5.18 | Other retinal disorders | Other retinal disorders | 3 |
| 5.19 | Macular degeneration | Macular degeneration | 2 |
| 5.20 | Retinal detachments and defects | Retinal detach & defects | 3 |
| 5.21 | Blindness and visual disturbances | Blindness & visual disturb | 3 |
| 5.22 | Malignant neoplasm of eye | Malignant neoplasm of eye | 1 |
| 6 | Ear conditions | Ear Conditions | — |
| 6.1 | Otitis externa | Otitis externa | 3 |
| 6.2 | Wax in ear | Wax in ear | 1 |
| 6.3 | Open wound of ear | Open wound of ear | 3 |
| 6.4 | Other disorders of ear | Other disorders of ear | 3 |
| 6.5 | Otitis media | Otitis media | 3 |
| 6.6 | Disorders of tympanic membrane | Dsdr of tympanic membrane | 3 |
| 6.7 | Disorders of middle ear | Disorders of middle ear | 3 |
| 6.8 | Vertiginous syndromes | Vertiginous syndromes | 3 |
| 6.9 | Mastoiditis | Mastoiditis | 3 |
| 6.10 | Hearing loss | Hearing loss | 3 |
| 6.11 | Malignant neoplasm of middle ear | Malig neop of middle ear | 1 |
| 7 | Nose Conditions | Nose conditions | — |
| 7.1 | Rhinitis | Rhinitis | 2 |
| 7.2 | Sinusitis | Sinusitis | 2 |
| 7.3 | Other nasal disorders | Other nasal disorders | 3 |
| 7.4 | Deviated nasal septum | Deviated nasal septum | 1 |
| 7.5 | Nasal bone fracture | Nasal bone fracture | 2 |
| 7.6 | Malignant neoplasm of nasal cavities | Malig neop of nasal cavities | 3 |
| 8 | Mouth Conditions | Mouth Conditions | — |
| 8.1 | Cleft palate and lip | Cleft palate and lip | 3 |
| 8.2 | Congenital anomalies of oral cavity | Cong anomalies oral cavity | 2 |
| 8.3 | Congenital anomalies of face, jaw, skull | Cong anom face, jaw, skull | 2 |
| 8.4 | Disorders of teeth | Disorders of teeth | 3 |
| 8.5 | Open wound of face and mount | Open wound face & mouth | 3 |
| 8.6 | Anomalies of jaw size | Anomalies of jaw size | 1 |
| 8.7 | Other dentofacial anomalies | Other dentofacial anom | 1 |
| 8.8 | Gingival and periodontal diseases | Gingival & periodontal dz | 2 |
| 8.9 | Other disease of supporting structure | Other dz supporting struct | 1 |
| 8.10 | Temporomandibular joint disorder | TMJ disorder | 1 |
| 8.11 | Other dentofacial disorders | Other dentofacial disorders | 3 |
| 8.12 | Diseases of jaws | Diseases of jaws | 2 |
| 8.13 | Disease of salivary glands | Diseases of salivary glands | 3 |
| 8.14 | Diseases of oral soft tissue | Diseases of oral soft tissue | 3 |
| 8.15 | Benign neoplasm of oral cavity | Benign neop of oral cavity | 2 |
| 8.16 | Jaw fracture | Jaw fracture | 3 |
| 8.17 | Malignant neoplasm of oral cavity | Malig neop oral cavity | 3 |
| 9 | Respiratory Conditions | Respiratory Conditions | — |
| 9.1 | Upper respiratory infections | Upper respiratory infections | 3 |
| 9.2 | Diseases of upper respiratory tract | Dz upper respiratory tract | 3 |
| 9.3 | Lower respiratory diseases | Lower respiratory disease | 3 |
| 9.4 | Acute bronchitis | Acute bronchitis | 2 |
| 9.5 | Hypertrophy of tonsils and adenoids | Hypertrophy tonsils & aden | 2 |
| 9.6 | Congenital anomaly of respiratory system | Cong anon respire system | 3 |
| 9.7 | Pneumonia | Pneumonia | 3 |
| 9.8 | Disorders of lower respiratory tract | Dsdr of lower respir tract | 1 |
| 9.9 | Pleurisy | Pleurisy | 2 |
| 9.10 | Chronic bronchitis | Chronic bronchitis | 2 |
| 9.11 | Asthma | Asthma | 3 |
| 9.12 | Benign neoplasm of bronchus and lung | Benign neop bronchus & lung | 3 |
| 9.13 | Emphysema | Emphysema | 2 |
| 9.14 | Chronic obstructive pulmonary disease | COPD | 1 |
| 9.15 | Spontaneous pneumothorax | Spon pneumothorax | 1 |
| 9.16 | Lung transplant | Lung transplant | 1 |
| 9.17 | Malignant neoplasm of pharynx and larynx | Malig neop pharyn & laryn | 2 |
| 9.18 | Malignant neoplasm of pleura | Malig neop of pleura | 2 |

TABLE 10-continued

List of Medical Conditions in Grouper Function

| Medical Condition Number | Medical Condition Long Description | Medical Condition Abbrev Description | Number of Severity Classes |
|---|---|---|---|
| 9.19 | Malignant neoplasm of bronchus and lung, active | Malig neop bron/lung, active | 2 |
| 9.20 | Malignant neoplasm of bronchus and lung, inactive | Malig neop bron/ling, inactive | 2 |
| 10 | Heart and Pulmonary Conditions | Heart and Pulmonary Cond | — |
| 10.1 | Abnormal heart beat | Abnormal heart beat | 2 |
| 10.2 | Hypertension | Hypertension | 3 |
| 10.3 | Congenital anomaly of circulatory system | Cong anom circulatory sys | 3 |
| 10.4 | Ventricular arrhythmias | Ventricular arrhythmias | 3 |
| 10.5 | Supraventricular arrhythmias | Supraventricular arrhythmias | 3 |
| 10.6 | Atrial septal defect | Atrial septal defect | 2 |
| 10.7 | Ventricular septal defect | Ventricular septal defect | 2 |
| 10.8 | Angina pectoris | Angina pectoris | 1 |
| 10.9 | Rheumatic fever | Rheumatic fever | 2 |
| 10.10 | Conduction disorders | Conduction disorders | 3 |
| 10.11 | Other heart disease | Other heart disease | 3 |
| 10.12 | Rheumatic heart disease | Rheumatic heart disease | 2 |
| 10.13 | Ischemic heart disease | Ischemic heart disease | 3 |
| 10.14 | Heart value disorders | Heart value disorders | 3 |
| 10.15 | Pulmonary heart disease | Pulmonary heart disease | 3 |
| 10.16 | Congestive heart failure | Congestive heart failure | 2 |
| 10.17 | Cardiomyopathy | Cardiomyopathy | 2 |
| 10.18 | Other aneurysm | Other aneurysm | 3 |
| 10.19 | Aortic aneurysm, initial | Aortic aneurysm, initial | 2 |
| 10.20 | Aortic aneurysm, follow-up | Aortic aneurysm, follow-up | 2 |
| 10.21 | Acute myocardial infarction, active | Acute myocardial infrct, active | 2 |
| 10.22 | Acute myocardial infarction, follow-up | Acute myocardial infct, fup | 2 |
| 10.23 | Heart transplant | Heart transplant | 1 |
| 10.24 | Malignant neoplasm of mediastinum | Malig neop of mediastinum | 2 |
| 10.25 | Malignant neoplasm of heart | Malig neoplasm of heart | 1 |
| 11 | Cerebrovascular and Artery Conditions | Cerebrovasc & Artery Cond | — |
| 11.1 | Pigmented nevus | Pigmented nevus | 1 |
| 11.2 | Superficial injury of head and neck | Superficial injury head & neck | 2 |
| 11.3 | Contusion of head and neck | Contusion of head and neck | 1 |
| 11.4 | Concussion | Concussion | 3 |
| 11.5 | Cerebral laceration | Cerebral laceration | 3 |
| 11.6 | Diseases of capillaries | Diseases of capillaries | 1 |
| 11.7 | Disorders of arteries | Disorders of arteries | 3 |
| 11.8 | Generalized arteriosclerosis | Generalized arteriosclerosis | 3 |
| 11.9 | Fracture of skull | Fracture of skull | 3 |
| 11.10 | Transient cerebral ischemia | Transient cerebral ischemia | 3 |
| 11.11 | Injury to blood vessels of head and neck | Inj to bl vessels head & neck | 1 |
| 11.12 | Occlusion of cerebral arteries | Occlusion of cerebral arteries | 3 |
| 11.13 | Cerebrovascular hemorrhage following injury | Cerebro hemorrhage, injury | 3 |
| 11.14 | Cerebrovascular hemorrhage | Cerebrovascular hemorrhage | 2 |
| 12 | Vein and Lymphatic Conditions | Vein & Lymphatic Cond | — |
| 12.1 | Anal fissure and fistula | Anal fissure and fistula | 2 |
| 12.2 | Hemorrhoids | Hemorrhoids | 3 |
| 12.3 | Other peripheral vascular diseases | Other peripheral vascular dz | 3 |
| 12.4 | Varicose veins of other sites | Varicose veins of other sites | 3 |
| 12.5 | Varicose veins of lower extremities | Varicose veins lower extreme | 3 |
| 12.6 | Thrombophlebitis | Thrombophlebitis | 3 |
| 13 | Digestive System Conditions | Digestive System Cond | — |
| 13.1 | Helicobacter pylori infection | Helicobacter pylori infection | 1 |
| 13.2 | Congenital anomaly of digestive system | Cong anom digestive system | 1 |
| 13.3 | Infectious diarrhea and gastroenteritis | Infect diarrhea/gastroenteritis | 2 |
| 13.4 | Other disorders of esophagus | Other disorders of esophagus | 3 |
| 13.5 | Gastritis and duodenitis | Gastritis and duodenitis | 3 |
| 13.6 | Gastroesophageal reflux | Gastroesophageal relux | 1 |
| 13.7 | Functional digestive disease | Functional digestive disease | 2 |
| 13.8 | Disorders of stomach and duodenum | Dsdr stomach & duodenum | 3 |
| 13.9 | Irritable colon | Irritable colon | 1 |
| 13.10 | Peptic ulcer | Peptic ulcer | 3 |
| 13.11 | Diverticula of intestine | Diverticula of intestine | 3 |
| 13.12 | Other diseases of intestine | Other diseases of intestine | 3 |
| 13.13 | Noninfectious gastroenteritis and colitis | Noninfect gastroent & colitis | 3 |
| 13.14 | Appendicitis | Appendicitis | 3 |
| 13.15 | Benign neoplasm of stomach | Benign neoplasm of stomach | 2 |
| 13.16 | Benign neoplasm of small intestine | Benign neoplasm small intestine | 2 |
| 13.17 | Benign neoplasm of colon and rectum | Benign neop colon/rectum | 2 |
| 13.18 | Intestinal obstruction | Intestinal obstruction | 2 |
| 13.19 | Vascular insufficiency of intestine | Vascular insufficiency intest | 2 |
| 13.20 | Crohn's disease | Crohn's disease | 3 |

TABLE 10-continued

List of Medical Conditions in Grouper Function

| Medical Condition Number | Medical Condition Long Description | Medical Condition Abbrev Description | Number of Severity Classes |
|---|---|---|---|
| 13.21 | Gastrointestinal hemorrhage | Gastrointestinal hemorrhage | 2 |
| 13.22 | Intestine and pancreas transplant | Intest/pancreas transplant | 1 |
| 13.23 | Malignant neoplasm of anus and rectum, initial | Malig neop anus/rectum, initial | 1 |
| 13.24 | Malignant neoplasm of anus and rectum, active | Malig neop anus/rectum, active | 1 |
| 13.25 | Malignant neoplasm of anus and rectum, fup | Malig neop anus/rectum, fup | 1 |
| 13.26 | Malignant neoplasm of esophagus | Malig neop of esophagus | 3 |
| 13.27 | Malignant neoplasm of stomach | Malign neoplasm of stomach | 1 |
| 13.28 | Malignant neoplasm of small intestine | Malig neop of small intestines | 2 |
| 13.29 | Malignant neoplasm of peritoneum | malign neop of peritoneum | 1 |
| 13.30 | Malig neop of colon, initial | Malig neop of colon, initial | 2 |
| 13.31 | Malignant neoplasm of colon, active | Malig neop of colon, active | 2 |
| 13.32 | Malignant neoplasm of colon, follow up | Malig neop of colon, fup | 2 |
| 14 | Hernias | Hernias | — |
| 14.1 | Other hernia site | Other hernia site | 3 |
| 14.2 | Diaphragmatic hernia | Diaphragmatic hernia | 3 |
| 14.3 | External abdominal hernias | External abdominal hernias | 3 |
| 15 | Hepatobiliary System and Pancreas | Hepatobiliary Sys & Pancreas | — |
| 15.1 | Congenital anomaly of hepatobiliary system | Cong anom hepatobiliary sys | 1 |
| 15.2 | Other disorders of biliary tract | Other disorders of biliary tract | 3 |
| 15.3 | Cholecystitis | Cholecystitis | 2 |
| 15.4 | Cholelithiasis | Cholelithiasis | 3 |
| 15.5 | Benign neoplasm of liver and biliary passages | Benign neop liver/biliary pass | 1 |
| 15.6 | Other disorders of liver | Other disorders of liver | 3 |
| 15.7 | Hepatitis | Hepatitis | 3 |
| 15.8 | Benign neoplasm of pancreas | Benign neoplasm of pancreas | 1 |
| 15.9 | Diseases of pancreas | Diseases of pancreas | 2 |
| 15.10 | Chronic liver disease | Chronic liver disease | 3 |
| 15.11 | Liver transplant | Liver transplant | 1 |
| 15.12 | Malignant neoplasm of gallbladder | Malign neop of gallbladder | 2 |
| 15.13 | Malignant neoplasm of liver | Malignant neoplasm of liver | 2 |
| 15.14 | Malignant neoplasm of pancreas | Malig neop of pancreas | 2 |
| 16 | Thyroid Disorders | Thyroid Disorders | — |
| 16.1 | Other disorders of thyroid | Other disorders of thyroid | 3 |
| 16.2 | Goiter | Goiter | 1 |
| 16.3 | Hypothyroidism | Hypothyroidism | 1 |
| 16.4 | Hyperthyroidism | Hyperthyroidism | 3 |
| 16.5 | Malignant neoplasm of thyroid | Malignant neoplasm of thyroid | 1 |
| 17 | Diabetes Mellitus | Diabetes Mellitus | — |
| 17.1 | Diabetes mellitus with no complications | Diabetes w/no complications | 1 |
| 17.2 | Diabetes mellitus with ophthalmic manifestation | Diabetes with ophthalmic | 3 |
| 17.3 | Diabetes mellitus with neurologic manifestation | Diabetes with neurologic | 3 |
| 17.4 | Diabetes mellitus with circulatory manifestation | Diabetes with circulatory | 3 |
| 17.5 | Diabetes mellitus with renal manifestation | Diabetes with renal | 3 |
| 17.6 | Diabetes mellitus with multiple complications | Diabetes with multiple comp | 3 |
| 18 | Other Endocrine Disorders | Other Endocrine Disorders | — |
| 18.1 | Other endocrine disorders | Other Endocrine Disorders | 3 |
| 18.2 | Disorders of adrenal gland | Disorders of adrenal gland | 2 |
| 18.3 | Disorders of pituitary gland | Disorders of pituitary gland | 3 |
| 18.4 | Benign neoplasm of pituitary gland | Benign neop of pituitary gland | 1 |
| 18.5 | Malignant neoplasm of other endocrine glands | Malig neop other endo glands | 2 |
| 18.6 | Malignant neoplasm of thymus gland | Malig neop of thymus gland | 1 |
| 18.7 | Malignant neoplasm of pituitary gland | Malig neop of pituitary gland | 1 |
| 18.8 | Malignant neoplasm of adrenal gland | Malig neop of adrenal gland | 1 |
| 19 | Metabolic Disorders | Metabolic Disorders | — |
| 19.1 | Ill-defined metabolic symptoms | Ill-defined metabolic symptoms | 1 |
| 19.2 | Disorders of fluids and electrolytes | Dsdr of fluids and electrolytes | 3 |
| 19.3 | Nutritional deficiencies | Nutritional deficiencies | 1 |
| 19.4 | Disorders of lipid metabolism | Disorders of lipid metabolism | 2 |
| 19.5 | Gout | Gout | 3 |
| 19.6 | Other disorders of metabolism | Other disorders of metabolism | 3 |
| 19.7 | Cystic fibrosis | Cystic fibrosis | 2 |
| 20 | Immunity and Blood Disorders | Immunity & Blood disorders | — |
| 20.1 | Congenital anomaly of spleen | Congenital anomaly of spleen | 1 |
| 20.2 | Disease of blood forming organs | Dz of blood forming organs | 1 |
| 20.3 | Disease of white blood cells | Diseases of white blood cells | 1 |
| 20.4 | Anemia disorders | Anemia disorders | 2 |
| 20.5 | Aplastic anemias | Aplastic anemias | 1 |
| 20.6 | Thrombocytopenia | Thrombocytopenia | 1 |
| 20.7 | Other disorders of blood | Other disorders of blood | 1 |
| 20.8 | Disorders of immune mechanism | Dsdr of immune mechanism | 3 |
| 20.9 | Malignant neoplasm of spleen | Malignant neoplasm of spleen | 1 |
| 21 | Lymphatic and Hematopoietic Tissue | Lymph & Hematopoietic Tiss | — |

TABLE 10-continued

List of Medical Conditions in Grouper Function

| Medical Condition Number | Medical Condition Long Description | Medical Condition Abbrev Description | Number of Severity Classes |
|---|---|---|---|
| 21.1 | Lymphadenitis | Lymphadenitis | 1 |
| 21.2 | Hemangioma | Hemangioma | 2 |
| 21.3 | Other malignant neoplasms of lymphoid tissue | Other malig neop lymph tissue | 3 |
| 21.4 | Burkitt's tumor | Burkitt's tumor | 2 |
| 21.5 | Lymphoma, active | Lymphoma, active | 2 |
| 21.6 | Lymphoma, inactive | Lymphoma, inactive | 2 |
| 21.7 | Hodgkin's disease, active | Hodgkin's disease, active | 2 |
| 21.8 | Hodgkin's disease, inactive | Hodgkin's disease, inactive | 2 |
| 21.9 | Sarcomas | Sarcomas | 2 |
| 21.10 | Leukemia, active | Leukemia, active | 2 |
| 21.11 | Leukemia, inactive | Leukemia, inactive | 2 |
| 21.12 | Multiple myeloma | Multiple myeloma | 2 |
| 22 | Urinary Tract and Kidney Conditions | Urinary Tract & Kidney Cond | — |
| 22.1 | Other disorders of urethra | Other disorders of urethra | 2 |
| 22.2 | Congenital anomalies of bladder and urethra | Cong anom bladder and urethra | 2 |
| 22.3 | Urinary tract infections | Urinary tract infections | 2 |
| 22.4 | Urethritis | Urethritis | 2 |
| 22.5 | Urethral stricture | Urethral stricture | 2 |
| 22.6 | Other disorders of bladder | Other disorders of bladder | 3 |
| 22.7 | Kidney infection | Kidney infection | 3 |
| 22.8 | Hydronephrosis | Hydronephrosis | 1 |
| 22.9 | Congenital anomalies of kidney and ureter | Cong anom kidney and ureter | 3 |
| 22.10 | Disorders of kidney and ureter | Disorders of kidney and ureter | 3 |
| 22.11 | Calculus of kidney and ureter | Calculus of kidney and ureter | 2 |
| 22.12 | Glomerulonephritis | Glomerulonephritis | 3 |
| 22.13 | Bladder transplant | Bladder transplant | 1 |
| 22.14 | Renal dialysis | Renal dialysis | 1 |
| 22.15 | Renal failure | Renal failure | 2 |
| 22.16 | Kidney transplant, initial | Kidney transplant, initial | 1 |
| 22.17 | Kidney transplant, follow-up | Kidney transplant, follow-up | 1 |
| 22.18 | Malignant neoplasm of bladder and urethra | Malig neop bladder and urethra | 1 |
| 22.19 | Malignant neoplasm of kidney and ureter | Malig neop kidney and ureter | 1 |
| 23 | Female Reproductive Conditions | Female Reproduction Cond | — |
| 23.1 | Disorders of cervix and vagina | Disorders of cervix and vagina | 3 |
| 23.2 | Cervicitis and vaginitis | Cervicitis and vaginitis | 2 |
| 23.3 | Uterovaginal prolapse | Uterovaginal prolapse | 3 |
| 23.4 | Other disorders of uterus | Other disorders of uterus | 3 |
| 23.5 | Other disorders of female genital organs | Other dsdr female genital org | 3 |
| 23.6 | Ovarian dysfunction | Ovarian dysfunction | 3 |
| 23.7 | Menstrual disorders | Menstrual disorders | 2 |
| 23.8 | Menopausal symptoms | Menstrual disorders | 1 |
| 23.9 | Benign neoplasm of uterus | Benign neoplasm of uterus | 2 |
| 23.10 | Endometriosis | Endometriosis | 2 |
| 23.11 | Ovarian cyst | Ovarian cyst | 1 |
| 23.12 | Carcinoma in situ of cervix | Carcinoma in situ of cervix | 1 |
| 23.13 | Malignant neoplasm of placenta | Malig neop of placenta | 1 |
| 23.14 | Malignant neoplasm of cervix and vagina | Malig neop of cervix & vagina | 2 |
| 23.15 | Malignant neoplasm of ovary and fallopian tube | Malig neop ovary & fallop tube | 1 |
| 23.16 | Malignant neoplasm of uterus | Malignant neoplasm of uterus | 1 |
| 24 | Male Reproductive Conditions | Male Reproductive Cond | — |
| 24.1 | Hydrocele | Hydrocele | 2 |
| 24.2 | Orchitis and epididymitis | Orchitis and epididymitis | 2 |
| 24.3 | Disorders of male genital organs | Dsdr of male genital organs | 3 |
| 24.4 | Disorders of penis | Disorders of penis | 2 |
| 24.5 | Other disorders of prostate | Other disorders of prostate | 3 |
| 24.6 | Prostatic hypertrophy and prostatitis | Prostatic hyertro & prostatitis | 2 |
| 24.7 | Malignant neoplasm of other male genital organs | Malig neop other male gen org | 3 |
| 24.8 | Malignant neoplasm of testis | Malignant neoplasm of testis | 1 |
| 24.9 | Malignant neoplasm of prostate, active | Malig neop of prostate, active | 1 |
| 24.10 | Malignant neoplasm of prostate, inactive | Malig neop of prostate, inactive | 1 |
| 25 | Infertility Treatment | Infertility Treatment | — |
| 25.1 | Contraceptive management | Contraceptive management | 1 |
| 25.2 | Infertility female | Infertility female | 2 |
| 25.3 | Procreative management | Procreative management | 1 |
| 25.4 | Infertility male | Infertility male | 1 |
| 26 | Maternity-Related Conditions | Maternity-Related Cond | — |
| 26.1 | Abnormal product of conception | Abnorm product of conception | 1 |
| 26.2 | Ectopic pregnancy | Ectopic pregnancy | 2 |
| 26.3 | Spontaneous and induced abortions | Spont and induced abortions | 1 |
| 26.4 | Single newborn, normal pregnancy | Single newborn, normal | 1 |

TABLE 10-continued

List of Medical Conditions in Grouper Function

| Medical Condition Number | Medical Condition Long Description | Medical Condition Abbrev Description | Number of Severity Classes |
|---|---|---|---|
| 26.5 | Single newborn, complicated pregnancy | Single newborn, complicated | 3 |
| 26.6 | Multiple newborns, normal pregnancy | Multiple newborns, normal | 1 |
| 26.7 | Multiple newborns, complicated pregnancy | Multiple newborns, complic | 3 |
| 26.8 | Other obstetrical care | Other obstetrical care | 1 |
| 26.9 | Completely normal delivery | Completely normal delivery | 1 |
| 26.10 | Multiple gestation | Multiple gestation | 1 |
| 26.11 | Complications before birth | Complications before birth | 3 |
| 26.12 | Complications of delivery | Complications of delivery | 3 |
| 27 | Neonatal Conditions | Neonatal Conditions | — |
| 27.1 | Other minor neonatal conditions | Minor neonatal conditions | 3 |
| 27.2 | Perinatal jaundice | Perinatal jaundice | 3 |
| 27.3 | Other major neonatal conditions | Major neonatal conditions | 3 |
| 27.4 | Respiratory distress syndrome | Respiratory distress syndrome | 1 |
| 27.5 | Disorders due to short gestation | Disorders to short gestation | 3 |
| 28 | Congenital Anomalies | Congenital Anomalies | — |
| 28.1 | Congenital anomalies of sense organs | Cong anom of sense organs | 3 |
| 28.2 | Congenital endocrine and metabolic anomaly | Cong endo/metabolic anom | 1 |
| 28.3 | Congenital reproductive system anomaly | Cong reproductive sys anom | 1 |
| 28.4 | Other chromosomal anomaly | Other chromosomal anomaly | 1 |
| 28.5 | Down's syndrome | Down's syndrome | 1 |
| 29 | Skin and Subcutaneous Tissue Conditions | Skin & Subcutaneous Tissue | — |
| 29.1 | Ill-defined integument symptoms | Ill-defined integument sym | 1 |
| 29.2 | Congenital anomalies of skin | Congenital anomalies of skin | 1 |
| 29.3 | Congenital integument anomaly | Cong integument anom | 1 |
| 29.4 | Other infections of skin and subcutaneous tissue | Other inf skin/subcutan tissue | 2 |
| 29.5 | Other disorders of skin and subcutaneous tissue | Other dsdr skin/subcutan tiss | 3 |
| 29.6 | Skin keratoses | Skin keratoses | 2 |
| 29.7 | Impetigo | Impetigo | 1 |
| 29.8 | Urticaria | Urticaria | 1 |
| 29.9 | Dermatitis and eczema | Dermatitis and eczema | 2 |
| 29.10 | Cellulites and abscess, finger and toe | Cellul & abscess, finger/toe | 2 |
| 29.11 | Cellulites and abscess, leg and buttock | Cellul & abscess, leg/buttock | 1 |
| 29.12 | Cellulites and abscess, other site | Cellul & abscess, other site | 1 |
| 29.13 | Rosacea | Rosacea | 1 |
| 29.14 | Dermatophytoses | Dermatophytoses | 2 |
| 29.15 | Sebaceous cyst | Sebaceous cyst | 1 |
| 29.16 | Pilonidal cyst | Pilonidal cyst | 2 |
| 29.17 | Acne | Acne | 1 |
| 29.18 | Lipoma | Lipoma | 2 |
| 29.19 | Benign neoplasm of skin | Benign neoplasm of skin | 1 |
| 29.20 | Diseases of nail, excluding infections | Dz of nail, excluding infections | 1 |
| 29.21 | Diseases of hair and hair follicles | Dz of hair and hair follicles | 2 |
| 29.22 | Erythematous condition | Erythematous condition | 2 |
| 29.23 | Psoriasis and pityriasis | Psoriasis and pityriasis | 2 |
| 29.24 | Carcinoma in situ of skin | Carcinoma in situ of skin | 1 |
| 29.25 | Chronic skin ulcer | Chronic skin ulcer | 2 |
| 29.26 | Other malignancy of skin | Other malignancy of skin | 2 |
| 29.27 | Kaposi's sarcoma | Kaposi's sarcoma | 3 |
| 29.28 | Malignant melanoma of skin, initial | Malig melanoma of skin, initial | 2 |
| 29.29 | Malignant melanoma of skin, active | Malig melanoma of skin, active | 2 |
| 29.30 | Malignant melanoma of skin, follow up | Malig melanoma of skin, fup | 2 |
| 30 | Breast Conditions | Breast Conditions | — |
| 30.1 | Inflammatory disease of breast | Inflammatory disease of breast | 2 |
| 30.2 | Cystic breast disease | Cystic breast disease | 2 |
| 30.3 | Benign neoplasm of breast | Benign neoplasm of breast | 1 |
| 30.4 | Carcinoma in situ of breast, initial | Carc in situ of breast, initial | 1 |
| 30.5 | Carcinoma in situ of breast, active | Carc in situ of breast, active | 1 |
| 30.6 | Carcinoma in situ of breast, follow-up | Carc in situ of breast, fup | 1 |
| 30.7 | Malignant neoplasm of breast skin | Malig neop of breast skin | 1 |
| 30.8 | Malignant neoplasms of breast, initial | Malig neop of breast, initial | 2 |
| 30.9 | Malignant neoplasm of breast, active | Malig neop of breast, active | 2 |
| 30.10 | Malignant neoplasm of breast, follow-up | Malig neop of breast, fup | 2 |
| 31 | Musculoskeletal Conditions | Musculoskeletal Conditions | — |
| 31.1 | Congenital musculoskeletal anomaly | Cong musculoskel anomaly | 1 |
| 31.2 | Congenital anomalies of spine | Congenital anomalies of spine | 3 |
| 31.3 | Other arthropathy disorders | Other arthropathy disorders | 3 |
| 31.4 | Bursitis | Bursitis | 3 |
| 31.5 | Other disorders of bone and cartilage | Other dsdr bone & cartilage | 3 |
| 31.6 | Nonallopathic lesions | Nonallopathic lesions | 2 |
| 31.7 | Bone transplant | Bone transplant | 1 |
| 31.8 | Cervical spine pain | Cervical spine pain | 3 |
| 31.9 | Low back pain | Low back pain | 3 |

TABLE 10-continued

List of Medical Conditions in Grouper Function

| Medical Condition Number | Medical Condition Long Description | Medical Condition Abbrev Description | Number of Severity Classes |
|---|---|---|---|
| 31.10 | Other acquired deformity | Other acquired deformity | 2 |
| 31.11 | Other curvature of spine | Other curvature of spine | 2 |
| 31.12 | Scoliosis | Scoliosis | 1 |
| 31.13 | Minor injury of trunk | Minor injury of trunk | 1 |
| 31.14 | Osteoporosis | Osteoporosis | 1 |
| 31.15 | Benign neoplasm of skull and trunk bones | Benign neop skull/trunk bones | 1 |
| 31.16 | Other osteochondropathies | Other osteochondropathies | 1 |
| 31.17 | Osteomyelitis | Osteomyelitis | 3 |
| 31.18 | Diffuse connective tissue disorders | Diffuse connective tiss dsdr | 1 |
| 31.19 | Rheumatoid arthritis | Rheumatoid arthritis | 3 |
| 31.20 | Dislocation of vertebra | Dislocation of vertebra | 3 |
| 31.21 | Fracture of vertebra | Fracture of vertebra | 3 |
| 31.22 | Major injury of trunk | Major injury of trunk | 1 |
| 31.23 | Traumatic pneumothorax | Traumatic pneumothorax | 3 |
| 31.24 | Crushing injury of trunk | Crushing injury of trunk | 2 |
| 31.25 | Malignant neoplasm of skull and trunk bones | Malig neop skull/trunk bones | 1 |
| 32 | Upper Limb Conditions | Upper Limb Conditions | — |
| 32.1 | Contusion of upper limb | Contusion of upper limb | 2 |
| 32.2 | Sprain/strain of wrist and finger | Sprain/strain of wrist & finger | 2 |
| 32.3 | Sprain/strain of upper arm | Sprain/strain of upper arm | 2 |
| 32.4 | Sprain/strain of lower arm | Sprain/strain of lower arm | 2 |
| 32.5 | Open wound of hand and fingers | Open wound hand & fingers | 3 |
| 32.6 | Open wound of arm | Open wound of arm | 3 |
| 32.7 | Dislocation of finger and wrist | Dislocation of finger and wrist | 3 |
| 32.8 | Dislocation of upper arm | Dislocation of upper arm | 3 |
| 32.9 | Congenital deformities of upper limb | Cong deformities upper limb | 3 |
| 32.10 | Benign neoplasm of upper limb | Benign neop of upper limb | 1 |
| 32.11 | Fracture of hand bones | Fracture of hand bones | 3 |
| 32.12 | Amputation of finger | Amputation of finger | 2 |
| 32.13 | Fracture of radius and ulna | Fracture of radius and ulna | 3 |
| 32.14 | Fracture of humerus | Fracture of humerus | 3 |
| 32.15 | Fracture of clavicle and scapula | Fracture of clavicle/scapula | 3 |
| 32.16 | Amputation of hand and arm | Amputation of hand and arm | 3 |
| 32.17 | Crushing injury of upper limb | Crushing injury of upper limb | 3 |
| 32.18 | Malignant neoplasm of upper limb | Malig neop of upper limb | 1 |
| 33 | Lower Limb Conditions | Lower Limb Conditions | — |
| 33.1 | Contusion of lower limb | Contusion of lower limb | 2 |
| 33.2 | Sprain/strain of foot and ankle | Sprain/strain of foot and ankle | 2 |
| 33.3 | Sprain/strain of leg | Sprain/strain of leg | 3 |
| 33.4 | Sprain/strain of hip and thigh | Sprain/strain of hip and thigh | 1 |
| 33.5 | Open wound of foot and toes | Open wound of foot and toes | 3 |
| 33.6 | Open wound of leg | Open wound of leg | 3 |
| 33.7 | Open wound of hip and thigh | Open wound of hip and thigh | 3 |
| 33.8 | Dislocation of foot and ankle | Dislocation of foot and ankle | 3 |
| 33.9 | Dislocation of knee | dislocation of knee | 2 |
| 33.10 | Dislocation of hip | Dislocation of hip | 3 |
| 33.11 | Congenital deformities of lower limb | Cong deformities lower limb | 3 |
| 33.12 | Joint replacement | Joint replacement | 1 |
| 33.13 | Benign neoplasm of lower limb | Benign neop of lower limb | 1 |
| 33.14 | Hammer toe | Hammer toe | 3 |
| 33.15 | Degenerative joint disease | Degenerative joint disease | 2 |
| 33.16 | Fracture of foot bones | Fracture of foot bones | 3 |
| 33.17 | Fracture of ankle | Fracture of ankle | 3 |
| 33.18 | Fracture of patella | Fracture of patella | 2 |
| 33.19 | Fracture of tibia and fibula | Fracture of tibia and fibula | 3 |
| 33.20 | Amputation of toes | Amputation of toes | 2 |
| 33.21 | Other joint derangement | Other joint derangement | 3 |
| 33.22 | Derangement of knee | Derangement of knee | 3 |
| 33.23 | Fracture of femur | Fracture of femur | 3 |
| 33.24 | Amputation of foot and leg | Amputation of foot and leg | 3 |
| 33.25 | Crushing injury of lower limb | Crushing injury of lower limb | 3 |
| 33.26 | Malignant neoplasm of lower limb | Malig neoplasm of lower limb | 1 |
| 34 | Mental Disorders | Mental Disorders | — |
| 34.1 | Other nonpsychotic disorders | Other nonpsychotic disorders | 3 |
| 34.2 | Psychogenic conditions | Psychogenic conditions | 3 |
| 34.3 | Sleep walking | Sleep walking | 1 |
| 34.4 | Hypersomnia | Hypersomnia | 1 |
| 34.5 | Insomnia | Insomnia | 2 |
| 34.6 | Other neurotic disorders | Other neurotic disorders | 1 |
| 34.7 | Maltreatment syndrome | Maltreatment syndrome | 1 |
| 34.8 | Sexual deviations | Sexual deviations | 1 |
| 34.9 | Tics and repetitive movements | Tics and repetitive movements | 3 |
| 34.10 | Hysteria | Hysteria | 3 |
| 34.11 | Delays in metal development | Delays in mental development | 2 |

TABLE 10-continued

List of Medical Conditions in Grouper Function

| Medical Condition Number | Medical Condition Long Description | Medical Condition Abbrev Description | Number of Severity Classes |
|---|---|---|---|
| 34.12 | Phobic disorders | Phobic disorders | 2 |
| 34.13 | Anxiety disorders | Anxiety discords | 2 |
| 34.14 | Personality and disturbance disorder | Personality & disturb dsdr | 3 |
| 34.15 | Other nonorganic psychoses | Other nonorganic psychoses | 1 |
| 34.16 | Other eating disorders | Other eating disorders | 1 |
| 34.17 | Nonpsychotic depression | Nonpsychotic depression | 2 |
| 34.18 | Obsessive-compulsive disorders | Obsessive-compulsive dsdr | 1 |
| 34.19 | Paranoid states | Paranoid states | 2 |
| 34.20 | Sleep apnea | Sleep apnea | 1 |
| 34.21 | Major depression | Major depression | 3 |
| 34.22 | Mental retardation | Mental retardation | 2 |
| 34.23 | Manic depression | Manic depression | 3 |
| 34.24 | Bipolar depression | Bipolar depression | 3 |
| 34.25 | Bulimia | Bulimia | 1 |
| 34.26 | Anorexia nervosa | Anorexia nervosa | 1 |
| 34.27 | Autism | Autism | 1 |
| 34.28 | Narcolepsy | Narcolepsy | 1 |
| 34.29 | Alcohol dependence | Alcohol dependence | 3 |
| 34.30 | Drug dependence | Drug dependence | 3 |
| 34.31 | Organic dementias | Organic dementias | 3 |
| 34.32 | Schizophrenia | Schizophrenia | 3 |
| 34.33 | Alzheimer's disease | Alzheimer's disease | 1 |
| 35 | Burns | Burns | — |
| 35.1 | Burn of upper limb | Burn of upper limb | 3 |
| 35.2 | Burn of lower limb | Burn of lower limb | 3 |
| 35.3 | Burns of head and neck | Burns of head and neck | 3 |
| 35.4 | Burn of trunk | Burn of trunk | 3 |
| 35.5 | Burn of multiple sites | Burn of multiple sites | 3 |
| 36 | Other Medical Conditions | Other Medical Conditions | — |
| 36.1 | Complication of surgery | Complication of surgery | 1 |
| 36.2 | Complication of genitourinary procedure | Complic genitourin procedure | 1 |
| 36.3 | Complication of orthopedic procedure | Complic orthopedic procedure | 1 |
| 36.4 | Complication of gastrointestinal procedure | Complic gastrointestinal proc | 1 |
| 36.5 | Complication of respiratory procedure | Complic respiratory procedure | 1 |
| 36.6 | Complications of trauma | Complications of trauma | 1 |
| 36.7 | Complication of nervous system procedure | Complic nervous sys proc | 1 |
| 36.8 | Complication of vascular procedure | Complic vascular procedure | 1 |
| 36.9 | Complication of transplant | Complication of transplant | 1 |
| 36.10 | Effects of external causes | Effects of external causes | 1 |
| 36.11 | Poisoning by medicines | Poisoning by medicines | 1 |
| 36.12 | Toxic effects of substances | Toxic effects of substances | 1 |
| 36.13 | Personal assaults | Personal assaults | 1 |
| 36.14 | Motor vehicle accident | Motor vehicle accident | 1 |
| 36.15 | General presenting symptoms | General presenting symptoms | 1 |
| 36.16 | Non-specific exanthem | Non-specific exanthem | 1 |
| 36.17 | Abdominal pain | Abdominal pain | 1 |
| 36.18 | Dyspnea | Dyspnea | 2 |
| 36.19 | Chest pain | Chest pain | 1 |
| 36.20 | Non-newborn jaundice | Non-newborn jaundice | 1 |
| 36.21 | Non-newborn cyanosis | Non-newborn cyanosis | 1 |
| 36.22 | Shock | Shock | 1 |
| 36.23 | Spleenomegaly | Spleenomegaly | 1 |
| 36.24 | Hepatomegaly | Hepatomegaly | 1 |
| 36.25 | Coma and stupor | Coma stupor | 1 |
| 36.26 | Gangrene | Gangrene | 1 |
| 37 | Replaced Diagnosis Codes | Replaced Diagnosis Codes | — |
| 37.1 | Replaced non-specific diagnosis codes | Replaced non-specific dx code | 1 |

An embodiment of the present invention forms longitudinal episodes of care for a patient using medical claims data. A longitudinal episode of care is defined as all services linked together that are used to treat a patient's medical condition within a specified period of time, including all ambulatory, outpatient, inpatient, and prescription drug experience. This linkage allows examination of a physician's (or a physician group's) global patterns of treatment for a patient with a specific condition, such as diabetes and arthritis. The longitudinal episode of care may also be used in patient disease management, patient health promotion and wellness, and many other healthcare programs.

Acute Episodes of Care

An acute episode of care has a finite duration and is defined by a specified time period, or window period. An embodiment of the present invention has three types of window periods for acute episodes of care.

Dynamic Window Period:

The specified time period, or window period, is based on the maximum number of days between contact with a provider for which follow-up care is still reasonable. Each of the medical conditions has its unique dynamic window period. If the date of service for a patient's episode is separated by a longer period than the dynamic window period, the latest date of service considered the start date for a new condition-specific episode of care.

Figure 3:
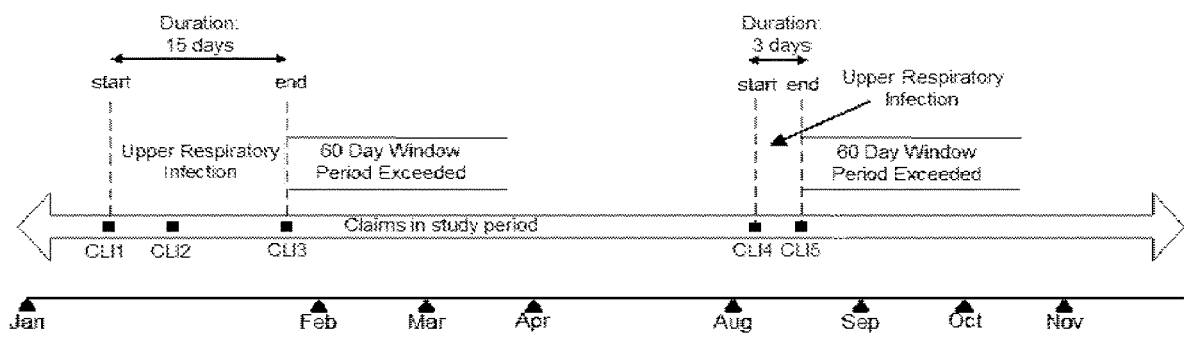
FIG. 3 is a drawing that illustrates a dynamic window period utilized in defining the duration of an acute episode of care in accordance with embodiments of the present invention.

For example, as shown in FIG. 3, the dynamic window period for Medical Condition 9.1-upper respiratory infections is 60 days. Assume that a patient had three services in January and two services in August of the same calendar year. Because the services in the series were separated by more than 60 days, these would be two episodes of care. Table 11A gives the dynamic window periods for medical conditions in PMC Group 9-Respiratory Conditions.

TABLE 11A

Medical Condition Dynamic Window Periods for PMC Group 9-Respiratory Conditions

| Medical Condition Number | Medical Condition Long Description | Window Periods |
|---|---|---|
| 6 | Ear conditions | — |
| 6.1 | Otitis externa | 90 |
| 6.2 | Wax in ear | 60 |
| 6.3 | Open wound of ear | 90 |
| 6.4 | Other disorders of ear | 90 |
| 6.5 | Otitis media | 90 |
| 6.6 | Disorders of tympanic membrane | 120 |
| 6.7 | Disorders of middle ear | 120 |
| 6.8 | Vertiginous syndromes | 180 |
| 6.9 | Mastoiditis | 180 |
| 6.10 | Hearing loss | 365 |
| 6.11 | Malignant neoplasm of middle ear | 365 |

Static Window Period:

The specified time period, or window period, is based on the maximum number of days after contact with a provider for which follow-up care is still reasonable. Each of the medical conditions has its unique static window period. From the initial date of service for a patient's episode, the static window period defines the fixed number of days to count from the initial date of service to define all services to include in the episode of care. Then, if another medical condition-specific service is observed for the same patient after the fixed number of window period days, this service is considered the start date for a new second condition-specific episode of care. For the second episode of care, the static window period defined fixed number of days is again applied.

Figure 4:
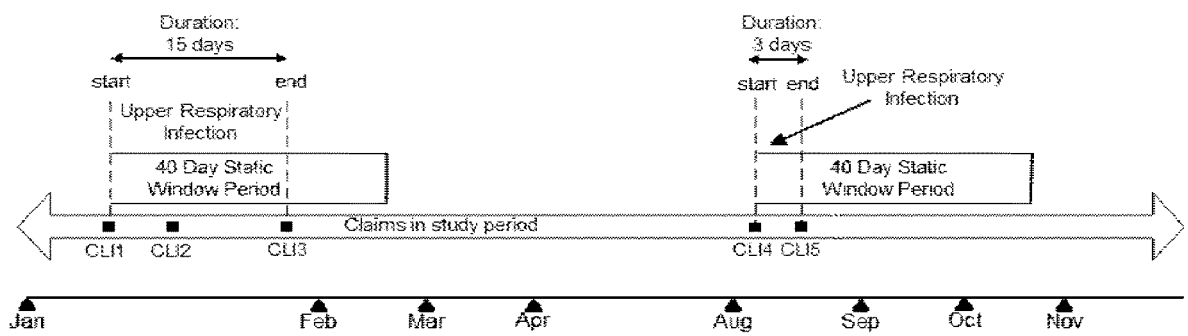
FIG. 4 is a drawing that illustrates a static window period utilized in defining the duration of an acute episode of care in accordance with embodiments of the present invention.

For example, as shown in FIG. 4, the static window period for Medical Condition 9.1 upper respiratory infections is 40 days. Assume that a patient had three services in January, the first on January fifth (5th), and two services in August in the same calendar year, the initial service on August tenth (10th). The three services in January were within the static 40 day window period from the initial service on January fifth (5th); this is because 40 days to count out from January fifth (5th) is about February fourteenth (14th). Therefore, these three services are in the first episode of care. Then, the second episode of care begins on August tenth (10th), and 40 days are counted out from August tenth (10th). Therefore, the two services in August are in the second episode of care. Table 11B gives the static widow periods for medical conditions in PMC Group 9-Respiratory Conditions.

TABLE 11B

Medical Condition Static Window Periods for PMC Group 9-Respiratory Conditions

| Medical Condition Number | Medical Condition Long Description | Static Window Periods |
|---|---|---|
| 6 | Ear conditions | — |
| 6.1 | Otitis externa | 60 |
| 6.2 | Wax in ear | 40 |
| 6.3 | Open wound of ear | 60 |
| 6.4 | Other disorders of ear | 60 |
| 6.5 | Otitis media | 60 |
| 6.6 | Disorders of tympanic membrane | 80 |
| 6.7 | Disorders of middle ear | 80 |
| 6.8 | Vertiginous syndromes | 120 |
| 6.9 | Mastoiditis | 120 |
| 6.10 | Hearing loss | — |
| 6.11 | Malignant neoplasm of middle ear | — |

Variable Window Period:

The specified time period, or window period, is based on the maximum number of days after contact with a provider for which follow-up care is still reasonable. Each of the medical conditions has its unique variable window period. From the initial date of service for a patient's episode, the window period defines the fixed number of days to count from the initial date of service to define all services to include in the episode of care. Then, if another medical condition-specific service is observed for the same patient after the fixed number of window period days, this service is considered the start date for a new second condition-specific episode of care. The fixed number of window period days is extended by a set number of days for each reoccurrence of a medical condition-specific episode of care.

Figure 5:
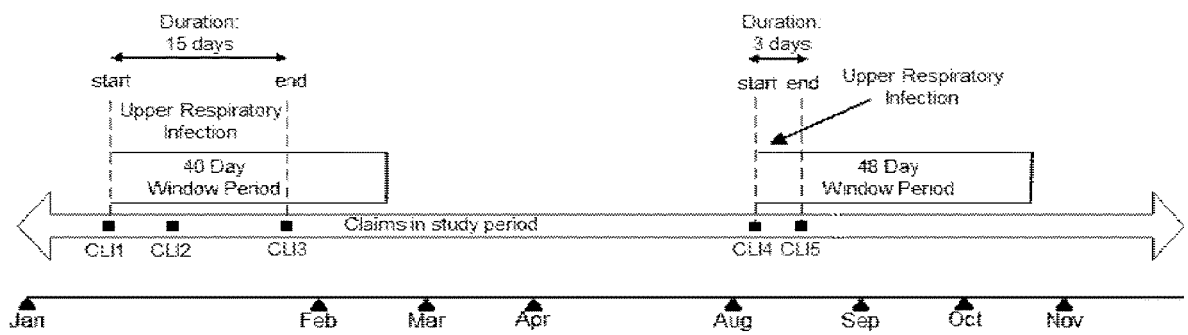
FIG. 5 is a drawing that illustrates a variable window period utilized in defining the duration of an acute episode of care in accordance with embodiments of the present invention.

For example, as shown in FIG. 5, the window period for the initial episode of Medical Condition 9.1 upper respiratory infections is 40 days. Assume that a patient had three services in January, the first on January fifth (5th), and two services in August in the same calendar year, the initial service on August tenth (10th). The three services in January were within the 40 day window period from the initial service on January fifth (5th); this is because 40 days to count out from January fifth (5th) is about February fourteenth (14th). Therefore, these three services are in the first episode of care. Then, the second episode of care begins on August tenth (10th), and the window period is extended by 8 days and therefore, 48 days are counted out from August tenth (10th). Therefore, the two services in August are in the second episode of care.

Chronic Episodes of Care

A chronic episode of care by definition is ongoing and once started will go on indefinitely. Therefore, chronic episodes of care have no window period associated with them and the user may define a desired fixed duration for Chronic Episodes of Care. For example, Medical condition 10.2 Hypertension or Medical Condition 9.11 Asthma have no window period and once an episode of Hypertension or Asthma starts, it will continue on indefinitely. In an embodiment, to calculate physician efficiency, chronic episodes may have a finite duration and end after 180 days or 365 days.

Step 100: Form Inpatient Encounters and Assign Diagnosis

The Grouper function first checks professional service CLIs for inpatient facility place of service to identify potential inpatient encounters. A professional service includes the Types of Service of visits, lab/path services, medical and surgical procedures, and diagnostic tests. All facility charges and prescription drugs are excluded from professional services. The professional services occur in a Place of Service of hospital inpatient.

The identification of a professional service that starts a potential inpatient encounter is called a trigger event.

The rule associates with the potential inpatient encounter all services that occurred on the dates following the trigger event. Services continue to be counted until an end date is reached. The end date is identified when there is a two-day gap in professional charges. At this point the potential encounter ends. For example, if one CLI ends on a Monday and the next CLI begins on Wednesday, then the two CLIs could be part of a single inpatient encounter because only one day (Tuesday) separates them. If the second CLI begins on Thursday, then it would be part of a separate inpatient encounter because two days (Tuesday and Wednesday) separate it from the first CLI.

The rule then looks at all professional service charges associated with the potential inpatient encounter to determine whether they total $350 or more. If the professional service charges total $350 or more, the rule concludes that we have identified an eligible inpatient encounter. Experience shows that charges should almost always be over this minimum threshold level. The minimum threshold level is subject to change over time.

For inpatient encounters with professional service charges of $350 or more, the rule assigns a diagnosis code to all CLIs associated with the encounter. To assign the appropriate diagnosis code, all professional service CLIs associated with the encounter are identified. The rule then temporarily assigns these professional service CLIs to one of 526 medical conditions. Using these temporary assignments, the rule adds up all charges by medical condition. The medical condition with the highest charge amount is then assigned as the medical condition for the entire encounter, and all CLIs associated with the encounter receive diagnosis codes appropriate for that medical condition.

The rule uses professional charges to identify the start and end dates of a hospital inpatient encounter. Facility services (i.e., room and board service and ancillary services) are assigned to the ongoing encounter using these start and end dates.

Step 120: Drop Inpatient Encounters without Minimal Professional Charges

If the overall professional service charges associated with the potential encounter do not reach $350, then an eligible inpatient encounter has not been identified. For example, consider a cardiac stress test that includes physician charges of $250 marked with inpatient facility as the place of service and a facility-related component of $300. Broken down in this way, we can see that the medical charges (non-facility and drug charges) do not meet the $350 threshold, and the potential encounter would not be regarded as an eligible inpatient encounter. When the potential encounter does not meet the $350 threshold, all CLIs associated with the potential inpatient encounter are released and will be examined as described in the next step.

Step 130: Form Outpatient Encounters and Assign Diagnosis

To identify outpatient facility encounters, the Grouper function examines all professional service CLIs except those already assigned to an inpatient facility encounter. The rule looks for professional service CLIs that have a Place of Service of inpatient hospital, emergency room, urgent care, outpatient facility, surgicenter, or birthing center as the place of service. At this point in the process, the professional service CLIs with a Place of Service of inpatient hospital did not meet the minimum hospital inpatient encounter criteria. These CLIs are now examined for a possible outpatient facility encounter.

The identification of a professional service that starts a potential outpatient encounter is called a trigger event. CLIs with Provider Type services that include only laboratory and durable medical equipment do not trigger a potential outpatient encounter.

Once a potential outpatient encounter has been identified, the rule inspects all CLIs that occurred on the date of the potential encounter to determine whether total charges equal or exceed $100. If so, then the rule concludes that an eligible outpatient encounter has been identified. Experience shows that charges should almost always be over this minimum threshold level. The minimum threshold level is subject to change over time.

For outpatient encounters with total charges of $100 or more, the rule assigns a diagnosis code to all CLIs associated with the encounter. To assign the appropriate diagnosis code, all professional service CLIs associated with the encounter are identified. The rule then temporarily assigns these professional service CLIs to one of 526 medical conditions. Using these temporary assignments, the rule adds up all charges by medical condition. The medical condition with the highest charge amount is then assigned as the medical condition for the entire encounter, and all CLIs associated with the encounter receive diagnosis codes appropriate for that medical condition.

Step 140: Drop Outpatient Encounters without Minimal Total Charges

If the total charges are less than $100, the rule concludes that that we have not identified an actual outpatient encounter. For example, many labs are performed in outpatient hospital facilities. This analysis helps ensure that lab-only events are not included as outpatient encounter.

CLIs associated with potential outpatient encounters that do not meet the $100 threshold may still be associated with medical condition episodes. They are released and through subsequent analysis may be assigned to the following service categories: Professional Visits, Diagnostic Tests, Laboratory and Pathology, Medical and Surgical Procedures, Prescription Drugs, Alternative Sites, or Other Medical Services.

Facility CLIs not associated with actual inpatient or outpatient encounters are assigned to other medical care service categories based primarily on the procedure code that may be present on the CLI. For example, if the procedure code indicates chemotherapy, it would be assigned to the service category Other Medical Services as part of the sub-service category Chemo/Radiology. If no explanatory procedure code is present, the facility CLI will be categorized under the service category Other Medical Services as part of the sub-service category Other Medical Care.

Step 150: Ill-Defined Diagnosis Code Rule

A patient's medical service will appear in an episode of care if the claim line item (CLI) has a valid and "defined" assigned ICD.9 code. For example, defined codes include ICD.9 codes such as 250.0 (diabetes without mention of complication), 244.3 (iatrogenic hypothyroidism), and 370.20 (superficial keratitis).

However, up to 40% of all CLIs may have "µl-defined" assigned ICD.9 codes. Ill-defined means that either the ICD.9 codes are either missing or nonspecific ICD.9 codes. Nonspecific codes include ICD.9 codes such as 780.9 (other general symptoms), 796.4 (other abnormal clinical findings), and 799 (other ill-defined causes of morbidity). Non-specific codes are treated as if the ICD.9 code on the CLI is missing. The CLI remains, but the ill-defined value on the CLI is ignored. Ill-defined ICD.9 coding falls into medical condition 37.1.

To prevent under-reporting of utilization within an episode of care, a defined ICD.9 code is assigned to CLIs with ill-defined ICD.9 codes. Consequently, the Ill-Defined Diagnosis Code Rule assigns a diagnosis code to each CLI with an ill-defined code as follows.

The Grouper function first looks for an appropriate diagnosis during the two days before and after the non-specific diagnosis code date. For example, assume a CLI has a non-specific diagnosis code on March 17. The rule looks backwards two days until March 15 for a valid and accurate diagnosis code. If no defined diagnosis code is found, then the rule looks two days forward until March 19 for a valid accurate diagnosis code. If no appropriate diagnosis is found, the rule then examines the five days before and after. If no appropriate diagnosis is found, the rule then examines the nine days before. In an embodiment, nine days forward in time can be examined and day period durations and number can be changed.

Moreover, the expected resource intensity level of each of 526 medical conditions is considered. If there are two separate CLIs on a given day that have a defined ICD.9 code, the rule assigns the diagnosis code of the more resource-intensive medical condition to the CLI with an ill-defined code. For example, if there is a diagnosis code for diabetes on February 15 and also a diagnosis code for upper respiratory tract infection on February 15, then diabetes will be assigned because it is more resource intensive. So, if there are two CLIs on the same day with different ICD.9 codes in the primary position field, then the most resource intensive diagnosis code is assigned during the two day look-back assignment process, during the two day look-forward assignment process, and so forth.

Table N shows the resource intensity rank order assigned to different medical conditions. The lower the resource intensity rank number for a medical condition, the higher the expected need for medical care services as compared to medical conditions with higher resource intensity rank numbers.

TABLE N

Resource Intensity Rank Order for Medical Conditions

| Medical Condition Number | Medical Condition Long Description | Resource Intensity Rank |
|---|---|---|
| 6 | Ear Conditions | — |
| 6.1 | Otitis externa | 464 |
| 6.2 | Wax in ear | 459 |
| 6.3 | Open wound of ear | 457 |
| 6.4 | Other disorders of ear | 455 |
| 6.5 | Otitis media | 454 |
| 6.6 | Disorders of tympanic membrane | 450 |
| 6.7 | Disorders of middle ear | 449 |
| 6.8 | Vertiginous syndromes | 440 |
| 6.9 | Mastoiditis | 436 |
| 6.10 | Hearing loss | 192 |
| 6.11 | Malignant neoplasm of middle ear | 84 |
| 22 | Urinary Tract and Kidney Conditions | — |
| 22.1 | Other disorders of urethra | 428 |
| 22.2 | Congenital anomalies of bladder and urethra | 413 |
| 22.3 | Urinary tract infections | 412 |
| 22.4 | Urethritis | 411 |
| 22.5 | Urethral stricture | 410 |
| 22.6 | Other disorders of bladder | 397 |

TABLE N-continued

Resource Intensity Rank Order for Medical Conditions

| Medical Condition Number | Medical Condition Long Description | Resource Intensity Rank |
|---|---|---|
| 22.7 | Kidney infection | 396 |
| 22.8 | Hydronephrosis | 335 |
| 22.9 | Congenital anomalies of kidney and ureter | 334 |
| 22.10 | Disorders of kidney and ureter | 140 |
| 22.11 | Calculus of kidney and ureter | 132 |
| 22.12 | Glomerulonephritis | 130 |
| 22.13 | Bladder transplant | 57 |
| 22.14 | Renal dialysis | 49 |
| 22.15 | Renal failure | 50 |
| 22.16 | Kidney transplant, initial | 46 |
| 22.17 | Kidney transplant, follow-up | Not applicable |
| 22.18 | Malignant neoplasm of bladder and urethra | 25 |
| 22.19 | Malignant neoplasm of kidney and ureter | 20 |

If a CLI has not been assigned to a valid ICD.9 code at this point, then the CLI will not be assigned to an episode of care at this point in time.

Prescription drug CLIs generally do not have an ICD.9 diagnosis code assigned. An embodiment of the present invention assigns a defined ICD.9 diagnosis code to each prescription drug CLI by applying the same Ill-Defined Diagnosis Code Rule as for any other service category that has an ill-defined ICD.9 code.

Step 160: Trigger Episode of Care Building

A Grouper function treats the start and end points for chronic and acute episodes differently. For chronic conditions (e.g., diabetes, asthma, ischemic heart disease), an episode of care begins when a CLI is initially found during the study period that has a defined ICD.9 code that has been assigned to that medical condition. Then, chronic conditions may continue on indefinitely as recognized by the window period of 365 days (refer to Table 11 for chronic disease window periods of 365 days).

However, for the purposes of physician efficiency analysis, chronic conditions are considered to be 180-day duration. Therefore, a chronic condition ends 180 days after identifying the first CLI with a diagnosis (defined ICD.9 code) for the specific chronic condition. The rule determines that the patient is present for 180 days during the study period after the first CLI with a diagnosis for the specific chronic condition. Moreover, in the physician efficiency analysis, all chronic conditions included in the analysis must start before the last day of the first half of the study period and must have a 180-day duration. The embodiment recognizes that this maximum allowable duration may be varied.

For acute conditions (e.g., upper respiratory infections, otitis media, conjunctivitis), an episode of care begins when a CLI is initially found during the study period that has a defined ICD.9 code that has been assigned to that medical condition.

For acute conditions, the patient's episode duration directly relates to the process of care. The process of care is identified using window periods for each medical condition. A medical condition's window period is based on the maximum number of days between contact with a provider for which follow-up care is still reasonable. Each medical condition has its own unique window period as presented for select medical conditions in Table 11. If the date of service for a patient's episode is separated from the previous date of service by a period longer than the window period for that condition, the latest date of service is considered the start date for a new condition-specific episode of care.

For example, upper respiratory infections generally last up to 30 days. The window period is made about 1.5-to-2.5 times as long as the expected average longer duration episodes for a medical condition to ensure episode completion. Therefore, the window period for upper respiratory infections is about 60 days. Acute condition episodes are considered complete (or end) if an amount of time (equal to the window period) elapses in which no ICD.9 codes for that condition are present.

Continuing our upper respiratory infection example, assume that a patient had three treatments for upper respiratory infection in January and two in the following August. The window period for upper respiratory infections is 60 days. Because the two groups of treatments were separated by more than 60 days, they would be considered two separate episodes of care. In the physician efficiency analysis, the maximum allowable duration for any acute condition is 180 days. The embodiment recognizes that this maximum allowable duration may be varied.

Step 170: Apply Rank Order Rule

After the triggering episode of care building rule, the rank order rule assigns claims that continue to have ill-defined diagnosis codes (e.g., missing or non-specific ICD.9 codes) to the highest resource-intensity ranked ongoing episode for a patient. Table N presents the resource intensity rank order for select medical conditions.

After the rank order rule, generally more than 98% of CLIs receive a defined ICD.9 code, and are assigned to one of the patient's ongoing condition-specific episodes of care. However, the percent ranges generally from 85% to 99% of CLIs that receive a defined ICD.9 code, depending on the accuracy of original ICD.9 coding in the particular medical claims data file of being examined.

Step 180: Apply CLI Day Rule

The Grouper function next examines the more resource-intensive medical condition episodes to ensure an appropriate number of CLIs are present within the episode of care. This is to ensure that no episodes are built because of a single CLI ICD.9 miscoding by a physician.

Most episodes, after being built, are eligible using the requirement that only one CLI is present with a condition-specific ICD.9 diagnosis code. For example, Table 12 shows that only one CLI with an ICD.9 code is required for conditions such as neuritis, headaches, conjunctivitis, otitis media, sinusitis, and upper respiratory infections.

However, some episodes, after being built, are eligible using the requirement that a CLI with a condition-specific ICD.9 code must be present on two different days. These are episodes of medical conditions that can be expected to last more than one day. For instance, the one CLI on two different days rule is required for conditions such as myoneural disorder, multiple sclerosis, pneumothorax, pneumocystosis, fracture of skull, intestinal obstruction, hepatitis, fracture of vertebra, and deep burns.

Other episodes, after being built, are eligible using the requirement that a CLI with a condition-specific ICD.9 code must be present on three different days. These episodes are more chronic by nature and require more resource intensive treatment. For example, the one CLI on three different days rule used for conditions such as injury of the spinal column, malignant neoplasm of nasal cavities, malignant neoplasm of lung, cerebrovascular hemorrhage, malignant neoplasm of pancreas, and renal failure.

If the built episode does not meet the required eligibility criteria, then the CLIs in the episode are released and through subsequent analysis, may be assigned to another of the patient's ongoing episodes of care. The diagnosis coding on the released CLIs is treated the same way as if the ICD.9 code were "μl-defined."

TABLE 12

Claim Line Item (CLI) Day Rule Table

| Medical Condition Number | Medical Condition Long Description | CLI Day Rule |
|---|---|---|
| 6 | Ear Conditions | — |
| 6.1 | Otitis externa | 1 |
| 6.2 | Wax in ear | 1 |
| 6.3 | Open wound of ear | 1 |
| 6.4 | Other disorders of ear | 1 |
| 6.5 | Otitis media | 1 |
| 6.6 | Disorders of tympanic membrane | 1 |
| 6.7 | Disorders of middle ear | 1 |
| 6.8 | Vertiginous syndromes | 1 |
| 6.9 | Mastoiditis | 1 |
| 6.10 | Hearing loss | 1 |
| 6.11 | Malignant neoplasm of middle ear | 3 |
| 16 | Thyroid Disorders | — |
| 16.1 | Other disorders of thyroid | 1 |
| 16.2 | Goiter | 1 |
| 16.3 | Hypothyroidism | 1 |
| 16.4 | Hyperthyroidism | 2 |
| 16.5 | Malignant neoplasm of thyroid | 3 |
| 22 | Urinary Tract and Kidney Conditions | — |
| 22.5 | Urethral stricture | 1 |
| 22.6 | Other disorders of bladder | 1 |
| 22.7 | Kidney infection | 1 |
| 22.8 | Hydronephrosis | 1 |
| 22.9 | Congenital anomalies of kidney and ureter | 1 |
| 22.10 | Disorders of kidney and ureter | 1 |
| 22.11 | Calculus of kidney and ureter | 1 |
| 22.12 | Glomerulonephritis | 1 |
| 22.13 | Bladder transplant | 3 |
| 22.14 | Renal dialysis | 3 |
| 22.15 | Renal failure | 3 |
| 22.16 | Kidney transplant, initial | 3 |
| 22.17 | Kidney transplant, follow-up | 3 |
| 22.18 | Malignant neoplasm of bladder and urethra | 3 |
| 22.19 | Malignant neoplasm of kidney and ureter | 3 |

Step 190: Apply Rank Order Rule

After the CLI day rule, the rank order rule is reapplied in an attempt to assign CLIs, which were released during the CLI day rule, a defined diagnosis code as defined under Step 170. The ill-defined CLIs are assigned to the highest resource-intensity ranked ongoing episode for a patient that has passed the CLI day rule.

Step 200: Severity-of-Illness Assignment Rule

Each patient's condition-specific episode is labeled with a severity-of-illness marker to reduce the heterogeneity of episodes within a medical condition. Severity-of-illness is defined as the probability of loss of function due to the physiologic progression or impact of the medical condition. Under this definition, the Grouper function uses only ICD.9 diagnosis codes to assign a patient's episode with a severity-of-illness marker. The Grouper function does not define severity-of-illness by resource utilization within the patient's condition-specific episode (such as whether a surgery or a resource-intensive diagnostic test was present in the patient's episode of care).

There are up to three (3) severity-of-illness (SOI) classes for each of the 526 medical conditions, with SOI-1 being the least severe (routine, noncomplicated) and SOI-3 being the most severe. However, the embodiment recognizes that there may be a differing number of SOI classes. Some medical conditions have only one or two severity-of-illness levels. Refer to the fourth column in Table 10, List of Medical Conditions in the Grouper function.

The severity-of-illness assignment rule operates to increase the SOI class on a patient's medical condition episode on the basis of two main criteria: (1) the ICD.9 codes that are present on the CLIs in each episode with respect to SOI class; and (2) the number of CLIs with ICD.9 codes in the more severe SOI classes.

With respect to the first criterion, Table 13 shows the selected diagnosis (ICD.9) codes listed in Table M stratified by SOI class. The ICD.9 codes within each SOI class are stratified based on the probability of loss of function due to the physiologic progression of the medical condition. A patient's episode may receive a more severe SOI ranking only if CLIs within the episode have ICD.9 coding present in the more severe SOI classes. For each medical condition episode of care, the severity-of-illness assignment rule accesses this table and determines whether the appropriate ICD.9 coding is present for a potential increase in SOI ranking.

TABLE 13

Selected Diagnosis (ICD.9) Codes by Medical Condition and Severity-of-Illness Level

| Medical Condition Number | Medical Condition Long Description | Number of Severity Classes | SOI-1 Class | SOI-2 Class | SOI-3 Class |
|---|---|---|---|---|---|
| 5.2 | Conjunctivitis | 2 | 077.0 | 372.1 | — |
|  |  |  | 077.8 | 372.14 |  |
|  |  |  | 372.0 | 372.22 |  |
|  |  |  | 372.01 |  |  |
| 6.5 | Otitis media | 3 | 381 | 381.20 | 382.01 |
|  |  |  | 381.02 | 382 | 382.1 |
|  |  |  | 381.06 | 382.00 |  |
|  |  |  |  | 382.4 |  |
| 7.2 | Sinusitis | 2 | 461.0 | 473 | — |
|  |  |  | 461.2 | 473.2 |  |
|  |  |  | 461.3 | 473.3 |  |
| 9.11 | Asthma | 3 | 493.0 | 493.01 | 493.21 |
|  |  |  | 493.02 | 493.2 |  |
|  |  |  | 493.1 |  |  |
| 10.2 | Hypertension | 3 | 401.1 | 402 | 402.11 |
|  |  |  | 405.1 | 402.0 | 404.01 |
|  |  |  |  | 403.00 | 404.11 |
|  |  |  |  | 403.1 |  |
|  |  |  |  | 405.0 |  |

With respect to the second criterion, Table 14 shows the minimum number of CLIs with required ICD.9 codes in the more severe SOI classes. For each medical condition episode of care, the severity-of-illness assignment rule accesses this table and determines the number of CLIs with required ICD.9 codes. If the number of CLIs with required ICD.9 codes is not achieved, then the patient's condition-specific episode will remain in the less severe SOI class (e.g., SOI-1 class). For example, a patient's sinusitis episode will receive an SOI-2 rank only if the episode contains 6 or more CLIs (refer to Table 14) with the ICD.9 codes listed in the sinusitis SOI-2 column of Table 13. Otherwise, the sinusitis episode will receive an SOI-1 rank.

TABLE 14

Number of CLIs with Required ICD.9 Codes in the More Severe SOI Classes

| Medical Condition Number | Medical Condition Long Description | Number of Severity Classes | SOI-1 Class | SOI-2 Class | SOI-3 Class |
|---|---|---|---|---|---|
| 5.2 | Conjunctivitis | 2 | 1 | 6 | — |
| 6.5 | Otitis media | 3 | 1 | 6 | 10 |
| 7.2 | Sinusitis | 2 | 1 | 6 | — |
| 9.11 | Asthma | 3 | 1 | 6 | 10 |
| 10.2 | Hypertension | 3 | 1 | 6 | 10 |

Step 210: Vertical Episode Merge Rule

Often the physiology of some medical conditions results in the manifestation of different symptoms. Depending on a patient's presenting symptoms, a physician may code a patient's diagnosis under different, but somewhat correlated medical conditions. Considering physician coding alone can result in episodes that are fragmented and don't give a full picture of care received for a medical condition. The Grouper function addresses this situation using a technique called the vertical episode merge rule.

For example, a physician may assign a patient to one of several cardiovascular disease-related medical conditions: ischemic heart disease, congestive heart failure, cardiac arrhythmia, hypertension, and other cardiovascular conditions. Likewise, presenting symptoms could result in a physician assigning a patient to one of several respiratory-related medical conditions: emphysema, chronic bronchitis, chronic obstructive pulmonary disease, asthma, and lower respiratory infections.

However, there usually is one underlying physiologic condition for a patient having several related medical conditions. To address this issue, physician panels were formulated to determine which of a patient's condition-specific episodes should be combined and when. The panels developed algorithms for combining related condition-specific episodes and assigning a patient to an overall medical condition episode based on the underlying most resource-intensive physiologic condition. Within each PMC Group, the panels listed medical conditions in ascending order of expected resource intensity level and physiologic progression of the condition or disease (from least resource intensive and physiologic progression to the most resource intensive and physiologic progression (refer to Table 10).

The vertical episode merge rule accesses Table 10 and merges a patient's condition-specific episodes in the same PMC Group. The episodes merge down the PMC Group medical condition list, always merging the patient's lesser resource intensity episodes into the most resource intensive medical condition episode. For example, assume a patient has episodes of ischemic heart disease, hypertension, and angina pectoris. Table 10 shows that ischemic heart disease is the more resource-intensive medical condition in PMC Group 10. Consequently, hypertension and angina pectoris are folded into the patient's ischemic heart disease episode. This indicates that remaining hypertension and angina pectoris episodes are derived from patients without ischemic heart disease.

Failure to consider a patient's underlying medical condition will distort the accuracy of a physician's efficiency measurement. For example, in the above patient, episodes would be generated for ischemic heart disease, hypertension, and angina pectoris even though the patient's angina and hypertension can be attributed to the underlying condition of ischemic heart disease. Consequently, utilization experience within the patient's ischemic heart disease episode would be understated. If the vertical episode merge rule did not exist for combining related condition-specific episodes, then a patient's medical condition utilization would be understated and a physician's practice pattern efficiency measure would be inaccurate.

The vertical episode merge rule considers how much time separates episodes in the same PMC Group. For Episode #2 to be considered for merge to a previously occurring Episode #1, a CLI from Episode #2 must either overlap Episode #1's duration time period or occur during the window period of Episode #1. In the vertical episode merge rule, any window period greater than 60 days is considered to be equal to 60 days. However, the embodiment recognizes that complete window period durations may exist.

Figure 6:
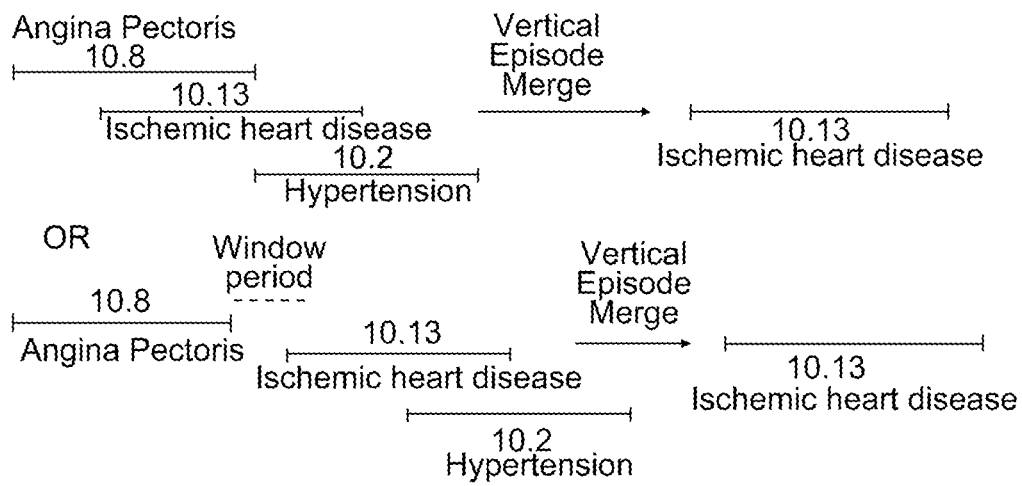
FIG. 6 illustrates, in flow diagram form, a sequence of acts executed to perform a vertical merge rule function in accordance with embodiments of the present invention.

FIG. 6 shows the vertical merge process for a patient's episodes of ischemic heart disease (10.13), angina pectoris (10.8), and hypertension (10.2). The episodes are merged together to form one episode of ischemic heart disease (10.13).

Step 220: Horizontal Episode Merge Rule

A patient may present with non-specific signs and symptoms before a more specific medical condition is diagnosed and treated. Non-specific medical conditions do not necessarily reflect a bodily system or organ system. Instead, they can reflect signs and symptoms such as abdominal pain, chest pain, dyspnea, spleenomegaly, non-specific exanthem, and jaundice. Table 15 presents sample non-specific medical conditions.

A patient's non-specific medical condition episodes need to be merged with the patient's more specific, resource-intensive medical condition episodes. Otherwise, a patient's specific medical condition utilization would be understated and a physician's practice pattern efficiency measure would be inaccurate. The Grouper function addresses this situation using a technique called the horizontal episode merge rule.

Figure 7:
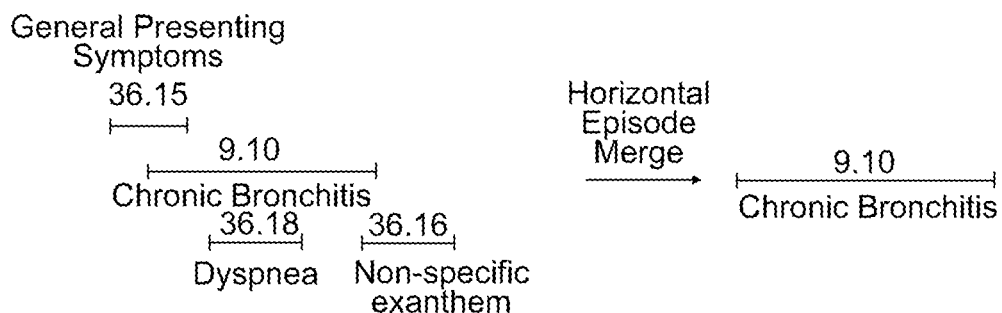
FIG. 7 illustrates, in flow diagram form, a sequence of acts executed to perform a horizontal merge rule function in accordance with embodiments of the present invention.

The Grouper function performs a horizontal episode merge when a non-specific medical condition episode overlaps a more specific medical condition episode. In order to be considered for horizontal episode merge, episodes must overlap so that they have service days in common. As illustrated in FIG. 7, the episode overlap may occur towards the beginning, middle, or end of the ongoing specific medical condition. Window periods between episodes are not considered for horizontal episode merges. However, the embodiment recognizes that window periods between episodes may exist.

The horizontal episode merge rule accesses Table 15 for each non-specific medical condition and merges the non-specific episodes into the more specific medical conditions in the PMC Group order defined in the table. The rule operates as follows. When a non-specific episode is identified, examine the Horizontal Episode Merge Order by PMC Group columns and attempt to merge the non-specific episode. The rule loops over each PMC Group in the defined precedence order, starting with the medical condition number stated in Table 15. The embodiment recognizes that the PMC Groups may change in order and number.

For example, for general presenting symptoms (36.15), the horizontal episode merge rule attempts to merge the patient's non-specific episode (36.15) with medical conditions in PMC Group 9 (Respiratory Conditions), beginning with lower respiratory diseases (Medical Condition 9.3) and moving down the list from 9.3 through 9.20. If no specific medical condition for the patient is found in PMC Group 9, then the rule loops over to find a medical condition in PMC Group 10 (Heart and Pulmonary Conditions), beginning with ventricular arrhythmias (Medical Condition 10.4). The rule moves down the medical condition list from 10.4 through 10.25. If no specific medical condition for the patient is found in PMC Group 10, then the rule loops over to find a medical condition in PMC Group 13 (Digestive System Conditions).

The process continues on until either the non-specific episode (36.15) is merged with a more specific episode, or the precedence ordered PMC Groups are exhausted, and no horizontal episode merge occurs. If no merge occurs, then the patient's non-specific episode (36.15) remains as general presenting symptoms.

TABLE 15

Selected Non-Specific Medical Conditions

| Medical Condition Number | Medical Condition Abbrev Description | Horizontal Episode Merge Order by PMC Group (Condition Listed Indicates Start Point for Merge) | | | | | | | | | |
|---|---|---|---|---|---|---|---|---|---|---|---|
| | | 1 | 2 | 3 | 4 | 5 | 6 | 7 | 8 | 9 | 10 |
| 2.1 | Intestinal infections | 3.1 | 20.5 | — | — | — | — | — | — | — | — |
| 2.2 | Other bacteria diseases | 3.1 | 9.10 | 21.3 | 20.1 | 22.12 | 13.19 | 35.1 | 23.3 | 24.5 | 10.14 |
| 36.1 | Complication of surgery | 21.3 | 31.17 | 33.5 | 32.5 | 10.4 | 11.8 | 14.1 | 35.1 | 12.1 | 24.5 |
| 36.15 | General presenting symptoms | 9.3 | 10.4 | 13.10 | 3.1 | 17.1 | 15.1 | 16.3 | 18.1 | 19.5 | 4.8 |
| 36.16 | Non-specific exanthem | 29.4 | 3.1 | 9.1 | 31.1 | 7.1 | 20.1 | 15.7 | 10.4 | 11.2 | 17.4 |
| 36.17 | Abdominal pain | 13.4 | 15.3 | 26.1 | 14.1 | 22.5 | 12.1 | 23.3 | 25.2 | 17.1 | 34.4 |
| 36.18 | Dyspnea | 9.1 | 10.14 | 3.1 | 7.2 | 8.1 | 4.8 | 21.3 | 31.17 | 34.4 | — |
| 36.19 | Chest pain | 10.4 | 9.10 | 3.1 | 21.3 | 34.4 | 30.8 | 31.17 | 30.2 | — | — |
| 36.20 | Non-newborn jaundice | 15.1 | 13.10 | 3.1 | 31.17 | 21.3 | 20.1 | 19.5 | — | — | — |
| 36.23 | Spleenomegaly | 20.1 | 21.3 | 3.1 | 31.17 | 19.5 | — | — | — | — | — |
| 36.24 | Hepatomegaly | 15.1 | 13.10 | 3.1 | 31.17 | 21.3 | 19.5 | — | — | — | — |

Step 230: Episode Treatment Stage Rule

Identifying different treatment stages, including initial, active, and follow-up treatment, is important in medical conditions such as the following: breast cancer, prostate cancer, colorectal cancer, acute myocardial infarction, and lymphoma.

The Grouper function is designed to separate initial, active, and follow-up treatment episodes using key episode identification markers, or triggers, for each applicable medical condition. Then, these episode types are separately examined to perform physician efficiency measurement.

Initial, active, and follow-up treatment stages are defined using breast cancer as an example. An initial breast cancer episode is one where the patient has a surgery for the cancer (e.g., lumpectomy, modified radial mastectomy). An active breast cancer episode is one where no surgery is present, but chemotherapy or radiation treatment is observed within the episode. Here, the patient underwent surgery in a previous study period, so no surgical event is found in the patient's current ongoing breast cancer episode. Instead, during the study period, the claims data shows that the patient is being treated with chemotherapy and/or radiation. The presence of these treatments defines an active breast cancer episode. The utilization pattern and charges are different for an active breast cancer patient as compared to an initial breast cancer patient. A follow-up breast cancer episode is one where no surgery, chemotherapy, or radiation treatment is present in the patient's episode of care. After initial and active treatments, physicians will continue to code for breast cancer over the future years of patient follow-up care.

In a given study period, physicians do not treat an equal distribution of each episode type (initial, active, and follow-up). Moreover, the episode types have different average charges. The group function correctly identifies treatment stages and examines them separately to ensure that physician efficiency scores accurately reflect the physician's practice.

Table 16 presents selected triggers descriptions and the applicable procedural codes (CPT-4, HCPCS, and UB92) for trigger formation. For instance, the mastectomy trigger consists of CPT-4 codes 19120-19272, whereby a trigger event of mastectomy may be formed if one or more CLIs in a patient's episode have CPT codes 19120-19272. Table 17 lists the selected triggers as they apply to several medical conditions that require treatment staging. The episode treatment stage rule accesses Table 16 and Table 17 and determines if the appropriate triggers exist to classify a patient's episode as initial, active, inactive, or follow-up.

TABLE 16

Selected Triggers for Differentiating Initial/Active/Inactive, Active/Inactive, Initial/Follow-Up, Active/Follow-up, and Initial/Active/Follow-up

| Trigger Number | Trigger Description | CPT-4 Codes | HCPCS Codes | UB92 Codes |
|---|---|---|---|---|
| 5 | Breast tissue expander | 11960-11971 | | |
| 9 | Mastectomy | 19120-19272 | | |
| 10 | Breast repair | 19316-19499 | | |
| 16 | Bone marrow transplant | 38230-38241, 85120 | | |
| 17 | Repair constricted aorta | 33840-33855, 33619 | | |
| 20 | Lymphadenectomy | 38562-38564 | | |
| 21 | Lymph node excision | 38300-38559 | | |
| 26 | Liver surgeries | 47001-47136, 47380-47399 | | |
| 28 | Exploratory laparotomy | 49000 | | |
| 39 | Sterotactic brain procedure | 61720-61770 | | |
| 46 | Emergency room visit | 99281-99285, 90500-90560 | | 981 |
| 47 | Inpatient visit | 99221-99239, 99251-99263, 99291-99298, 99431-99440, 90200-90292, 99160-99172 | | 987 |
| 48 | Chemotherapy drugs | | J0640, J1020-J1040, J1100, J1710-J1720, J1830, J2320-J2322, J2920-J2930, J7505, J8530-J8610, Q0083 | J1094, J1440 |
| 49 | Chemotherapy administration | 96400-96549 | | 280, 289, 335 |
| 50 | Radiation therapy | 77261-77499 | | 330-333, 342 |

TABLE 17

Selected Trigger Applications for Medical Conditions: Initial/Active/Inactive, Active/Inactive, Initial/Follow-Up, Active/Follow-up, and Initial/Active/Follow-up

| | | Aortic Aneurysm | | Lymphoma | | Malignant neoplasm, breast | | |
|---|---|---|---|---|---|---|---|---|
| Trigger Number | Trigger Description | Active 10.21 | Follow-Up 10.22 | Active 21.5 | Inactive 21.6 | Initial 30.8 | Active 30.9 | Follow-up 30.10 |
| 5 | Breast tissue expander | | | | | | | Yes |
| 9 | Mastectomy | | | | | | Yes | |
| 10 | Breast repair | | | | | | | Yes |
| 16 | Bone marrow transplant | | | Yes | | Yes | | |
| 20 | Lymphadenectomy | | | Yes | | Yes | | |
| 21 | Lymph node excision | | | Yes | | Yes | | |
| 26 | Liver surgeries | | | Yes | | | | |
| 28 | Exploratory laparotomy | | | Yes | | | | |
| 39 | Sterotactic brain procedure | | | Yes | | | | |
| 46 | Emergency room visit | Yes | | | | | | |
| 47 | Inpatient visit | Yes | | | | | | |
| 48 | Chemotherapy drugs | | | Yes | | | Yes | |
| 49 | Chemotherapy administration | | | Yes | | | Yes | |
| 50 | Radiation therapy | | | Yes | | | Yes | |

For example, a patient's malignant neoplasm of the breast episode may be classified as initial if the following trigger events are present: breast repair, bone marrow transplant, lymphadenectomy, or lymph node excision. A patient's malignant neoplasm of the breast may be classified as active if the following trigger events are present: breast tissue expander, breast repair, chemotherapy drugs, chemotherapy administration, or radiation therapy.

However, the rule also examines Table 18 to determine whether the triggers meet specific qualifying event criteria. If a trigger event does not meet one of the specified criteria in Table 18 for a medical condition, then the trigger event does not count. For instance, in order for a patient's malignant neoplasm of the breast to be classified as initial, the table shows that: (1) one of the trigger events identifying the episode as initial needs to be $150 or more; or (2) two or more trigger events need to be present in the episode.

If these criteria are not met for the episode to be assigned to the initial treatment stage, then the rule accesses the Table 18 to determine if the patient's episode of malignant neoplasm of the breast may be assigned to the active treatment stage. The active treatment stage is assigned if a specific trigger event has a claim line item (CLI) on three different days. If no specific trigger event has a CLI on three different days, then the patient's episode is classified as follow-up.

table to form diabetes with multiple complications (17.6). This medical condition does not exist before the complex condition merge rule. Table 19 shows that a patient is placed into diabetes with multiple complications (17.6) if the patient has any combination of 17.2, 17.3, 17.4, and 17.5.

The final list of diabetes medical conditions is as follows: 17.1 diabetes mellitus with no complications; 17.2 diabetes mellitus with ophthalmic manifestation; 17.3 diabetes mellitus with neurologic manifestation; 17.4 diabetes mellitus with circulatory manifestation; 17.5 diabetes mellitus with renal manifestation; and 17.6 diabetes mellitus with multiple complications.

TABLE 19

Complex Condition Merge for Diabetes Mellitus

| Medical Condition Number 1 | Medical Condition Number 2 | Patients Episodes are Merged And Placed into Highest Resource Intensity Episode |
|---|---|---|
| 17.1 | 17.2 | 17.2 |
| 17.1 | 17.3 | 17.3 |
| 17.1 | 17.4 | 17.4 |
| 17.1 | 17.5 | 17.5 |
| — | Any combination of 17.2, 17.3, 17.4 and 17.5 | 17.6 |

TABLE 18

Qualifying Event Criteria for Triggers to Apply to Medical Conditions: Initial/Active/Inactive, Active/Inactive, Initial/Follow-Up, Active/Follow-up, and Initial/Active/Follow-up

| Medical Condition Number | Medical Condition Long Description | Criteria Examined | Qualifying Event |
|---|---|---|---|
| 10.19 | Aortic aneurysm, initial | Criterion 1, or | 1 trigger procedure > $150 |
|  |  | Criterion 2, or | Need >2 different trigger proc |
|  |  | Criterion 3 | Any 1 trigger CLI on 3 different days |
| 10.20 | Aortic aneurysm, follow-up | Episode defaults to 10.20 if Criteria 1-3 above not achieved. | |
| 21.5 | Lymphoma, active | Criterion 1, or | 1 trigger procedure > $150 |
|  |  | Criterion 2, or | Need >2 different trigger proc |
|  |  | Criterion 3 | Any 1 trigger CLI on 3 different days |
| 21.6 | Lymphoma, inactive | Episode defaults to 21.6 if Criteria 1-3 above not achieved. | |
| 30.8 | Malignant neoplam of breast, initial | Critierion 1, or | 1 trigger procedure > $150 |
|  |  | Criterion 2, or | Need >2 different trigger proc |
|  |  | Criterion 3 | Not applicable |
|  |  | Episode defaults to 30.9 if Criteria 1-3 not achieved. | |
| 30.9 | Malignant neoplasm of breast, active | Rule now examines if episode meets following criteria: | |
|  |  | Critierion 1, or | Any 1 trigger CLI on 3 different days |
|  |  | Criterion 2, or | Not applicable |
|  |  | Criterion 3 | Not applicable |
| 30.10 | Malignant neoplasm of breast, follow-up | Episode defaults to 30.10 if Criteria 1-3 above not achieved. | |

Stage 240: Complex Condition Merge Rule

Certain medical conditions represent the combination of two or more medical conditions in the same PMC Group. For example, diabetes mellitus with multiple complications (17.6) is one such medical condition. The Grouper function initially formulates one or more of the following episodes of diabetes for a patient: 17.1 diabetes mellitus with no complications; 17.2 diabetes mellitus with ophthalmic manifestation; 17.3 diabetes mellitus with neurologic manifestation; 17.4 diabetes mellitus with circulatory manifestation; and 17.5 diabetes mellitus with renal manifestation.

The complex condition merge rule then examines all initially formed episodes of diabetes for a patient and determines whether the patient has any of the combinations listed in Table 19. For instance, if a patient has an episode of diabetes with no complications (17.1) and an episode of diabetes with ophthalmic manifestations (17.2), then both episodes will be merges into 17.2. The rule also accesses the Step 250: Complication Episode Merge Rule The Grouper function uses the complication episode merge rule to identify medical conditions as complicating factors to a patient's underlying medical condition being examined. Complicating factors are patient-specific episodes that are clinically determined to be related to the underlying disease.

For example, physicians' code up to 70% of an average diabetic's charges under the related complications to diabetes (e.g., neuropathies, circulatory, eye, renal) and not diabetes care. This is because physicians frequently code only for the specific condition that they are treating at the time, which is often not diabetes. Therefore, without considering and including complication episodes with the actual diabetes episode, patient severity-of-illness and physician efficiency differences may be attributed to incomplete episode charges and utilization.

Another example is human immunodeficiency virus (HIV) conditions where tracking related complications is important or up to 80% of an average HIV patient's charges and utilization may be under-reported. These complicating conditions include pneumonia, opportunistic infections (e.g., cryptococcosis, candidiasis), nerve conditions, eye conditions, blood disorders, and malignancies. The Grouper function includes related complications and links them to the underlying condition being examined.

A third example is maternity conditions where complications before birth and complications of delivery are important to track to single and multiple newborn deliveries. Otherwise, up to 50% of an average maternity patient's charges and utilization may be under-reported.

Using HIV conditions as an example for applying the complication episode merge rule, the Grouper function initially formulates the following underlying medical condition episode for a patient: 3.1 Asymptomatic HIV infection.

One or more medical conditions then are linked as complications to the underlying medical condition of asymptomatic HIV infection. This linkage may result in the underlying medical condition episode being upcoded to a more resource intensive medical condition to reflect the physiologic progression of the disease and/or the underlying medical condition episode being moved to a higher severity-of-illness (SOI) class.

Table 20 shows the medical conditions linked to asymptomatic HIV infection (3.1) that will upcode the patient's episode to HIV with infectious complication (3.2). The rule accesses Table 20 to determine if any of the complication medical conditions are present for the patient. If yes, then the patient is upcoded to HIV with infectious complication (3.2). For all complication episodes, the charges and utilization are merged into the ongoing HIV with infectious complication episode.

TABLE 20

Complication Medical Conditions Linked to the Underlying Medical Condition of HIV Infection

| Medical | | Complication | | HIV with Infect Comp (3.2) | | |
| --- | --- | --- | --- | --- | --- | --- |
| Cond Number | Verbal Description | Condition Number | Complication Condition Verbal Description | SOI Class | SOI Class | SOI Class |
| 3.2 | HIV with infectious comp | 2.5 | Tuberculosis | 1 | | |
| | | 2.5 | Tuberculosis | | 2 | |
| | | 2.5 | Tuberculosis | | | 3 |
| | | 2.11 | Cytomegalic inclusion d | 1 | | |
| | | 2.16 | Cryptococcosis | 1 | | |
| | | 2.17 | Candidiasis | 1 | | |
| | | 2.17 | Candidiasis | | 2 | |
| | | 2.17 | Candidiasis | | | 3 |
| | | 2.18 | Coccidioidomycosis | 1 | | |
| | | 2.18 | Coccidioidomycosis | | 2 | |
| | | 2.18 | Coccidioidomycosis | | | 3 |
| | | 2.19 | Histoplasmosis | 1 | | |
| | | 2.19 | Histoplasmosis | | 2 | |
| | | 2.19 | Histoplasmosis | | | 3 |
| | | 2.20 | Blastomycotic infection | 1 | | |
| | | 2.20 | Blastomycotic infection | | 2 | |
| | | 2.23 | Toxoplasmosis | 1 | | |
| | | 2.23 | Toxoplasmosis | | 2 | |
| | | 2.23 | Toxoplasmosis | | | 3 |
| | | 2.24 | Pneumocystosis | 1 | | |
| | | 9.7 | Pneumonia | 1 | | |
| | | 9.7 | Pneumonia | | 2 | |
| | | 9.7 | Pneumonia | | | 3 |

The rule then examines the SOI class of the linked complication medical condition episode. For instance, Table 20 illustrates that toxoplasmosis episodes with SOI-1 rank will not move the patient's HIV with infectious complication episode to a higher SOI class. However, the table shows that toxoplasmosis episodes with SOI-2 rank will move the patient's HIV with infectious complication episode to the SOI-2 class.

After applying the complication episode merge rule, Table 21 shows that a patient with HIV infection may be placed into one of the following PMC Group 3 medical conditions and SOI classes.

TABLE 21

Human Immunodeficiency Infection Medical Conditions and SOI Classes After Linking of Complication Episodes

| Medical Condition Number | Medical Condition Long Description | Number of Severity Classes |
| --- | --- | --- |
| 3 | Human Immunodeficiency Infections | |
| 3.1 | HIV infection with no complications | 1 |
| 3.2 | HIV infection with infectious complication | 3 |
| 3.3 | HIV infection with CNS involvement | 3 |
| 3.4 | HIV infection with malignancy | 3 |
| 3.5 | HIV infection with multiple complications | 3 |

Step 260: Comorbidity Marker Rule

In an embodiment, the Grouper function also uses a comorbidity marker rule to identify medical conditions as comorbidities to a patient's medical condition being examined. A comorbidity is a concurrent resource-intensive medical condition that is not related to the underlying disease state. For example, breast cancer is considered a comorbid condition to diabetes.

With respect to comorbidities, the individual physician efficiency analysis may eliminate from analysis any patient episode with a linked comorbidity. If such episodes are not eliminated, unnecessary heterogeneity may remain within condition-specific episodes. This heterogeneity adds error to any evaluation of physician efficiency.

Table 22 presents selected comorbid medical conditions. As indicated in Table 22, for a comorbid medical condition to be tracked to a medical condition episode in question, the patient's comorbid medical condition episode needs to be of a certain SOI class and total charge amount. For example, Table 22 shows that a patient's seizure disorder needs to be of SOI-2 class and at least $2,500 to be linked to another medical condition as a comorbidity. It is to be understood that the medical conditions listed in Table 22 do not need to have qualifying events, such as a charge amount or SOI level.

TABLE 22

Selected List of Medical Condition Comorbiditiesto a Patient's Medical Condition Being Examined

| Medical Condition Number | Medical Condition Long Description | Minimum Episode Charges | Minimum SOI Level |
|---|---|---|---|
| 2.4 | Septicemia | $3,500 | 1 |
| 2.5 | Tuberculosis | $2,500 | 1 |
| 2.11 | Cytomegalic inclusion disease | $3,500 | 1 |
| 3.4 | HIV infection with malignancy | $1,500 | 1 |
| 3.5 | HIV infection with multiple complications | $1,500 | 1 |
| 4.11 | Inflammatory diseases of CNS | $3,500 | 1 |
| 4.19 | Multiple sclerosis | $2,500 | 1 |
| 4.24 | Malignant neoplasm of brain, initial care | $2,000 | 1 |
| 4.25 | Malignant neoplasm of brain, active care | $2,000 | 1 |
| 9.13 | Emphysema | $3,000 | 2 |
| 9.14 | Chronic obstructive pulmonary disease | $4,000 | 1 |

TABLE 22-continued

Selected List of Medical Condition Comorbiditiesto a Patient's Medical Condition Being Examined

| Medical Condition Number | Medical Condition Long Description | Minimum Episode Charges | Minimum SOI Level |
|---|---|---|---|
| 9.15 | Spontaneous pneumothorax | $2,500 | 1 |
| 9.19 | Malignant neoplasm of bronchus and lung, active | $3,000 | 1 |
| 10.16 | Congestive heart failure | $3,000 | 2 |
| 10.17 | Cardiomyopathy | $3,000 | 2 |
| 10.21 | Acute myocardial infarction, active | $3,500 | 1 |
| 10.22 | Acute myocardial infarction, follow-up | $3,000 | 1 |
| 11.14 | Cerebrovascular hemorrhage | $2,500 | 1 |
| 13.20 | Crohn's disease | $3,000 | 2 |
| 13.27 | Malignant neoplasm of stomach | $2,000 | 1 |
| 13.30 | Malignant neoplasm of colon, initial | $3,500 | 1 |
| 15.10 | Chronic liver disease | $2,500 | 2 |
| 15.11 | Liver transplant | $2,000 | 1 |
| 15.14 | Malignant neoplasm of pancreas | $2,000 | 1 |
| 17.5 | Diabetes mellitus with renal manifestation | $3,750 | 1 |
| 17.6 | Diabetes mellitus with multiple complications | $3,750 | 1 |
| 20.9 | Malignant neoplasm of spleen | $2,000 | 1 |
| 29.27 | Kaposi's sarcoma | $2,000 | 1 |
| 31.19 | Rheumatoid arthritis | $3,000 | 2 |
| 34.31 | Organic dementias | $3,000 | 2 |
| 34.32 | Schizophrenia | $3,000 | 2 |

Step 270: Partial Episode Marker Rules

The Grouper function determines partial and complete episodes of care for both acute and chronic episodes. The user decides whether to include or exclude partial episodes of care from analysis using the parameter SWITCH_DROP-PARTIAL in the RUN.INI file (refer to Table 6).

In an embodiment, the system of the present invention uses different analytical approaches to identify partial episodes for acute and chronic medical conditions, as described below.

With respect to acute conditions, the partial episode marker rule states that acute episodes must pass the tests defined in Table 23 for both the beginning and the end of the study period, or the episodes will be marked as partial. The maximum allowable duration for any acute condition is 180 days.

TABLE 23

Partial Acute Episodes of Care

| If the medical condition window period is: | Then the episode is marked as partial when it: |
|---|---|
| Study-Start Partial Episodes (Episodes declared partial because they may have begun before the start of the study period.) | |
| Equal to or greater than 90 days | Begins within 30 days of the start of the study period |
| Less than 90 days | Begins closer than 33% of the window period from the start of the study period |
| Study-End Partial Episodes (Episodes declared partial because they may not be complete at the end of the study period.) | |
| Equal to or greater than 120 days | Begins during the last quarter of the study period |
| Less than 120 days | The last CLI associated with the episode is closer than 33% of the window period to the end of the study period, unless the episode has been under way for 180 days |

For acute conditions having a window period equal to or greater than 120 days, the last three months of the study period are used as a run-out interval to allow all incomplete acute episodes as of the beginning of the fourth quarter to end. Allowing for a run-out interval reduces the fragmentation of acute episodes and therefore increases the validity and reliability of treatment pattern results.

For acute conditions having a window period less than 120 days, the episode will be marked as partial if the last CLI associated with the episode is closer than 33% of the window period to the end of the study period. For example, upper respiratory infection (URI) has a window period of 60 days. Assume a patient's ongoing episode of URI has a CLI with a date of service of December 20, and the end of the study period is December 31. Then, this URI episode would be marked as partial because the episode's last CLI is less than 33% of the window period (or 20 days) to the end of the study period.

In an embodiment, all chronic medical condition episodes begin during the first half of the study period to be considered complete episodes of care. Chronic episodes beginning in the second half of the study period are treated as partial. In an embodiment, the duration for a chronic condition is 180 days for the physician efficiency analysis. However, chronic conditions may continue on indefinitely as recognized by the window period of 365 days (refer to Table 11 for chronic disease window periods of 365 days).

Step 6: Perform PATAN Output Process

The PATAN output process involves four main functions.

The first function is to eliminate episodes of care that have been marked for removal during the read in RUN.INI file step. These episodes include: (1) partial episodes of care; and (2) episodes marked with comorbidities. If these two types of episodes have not been marked for deletion, then the episodes will be presented in the PATAN output file.

The second function is to assign episodes to physicians using the episode assignment logic as defined by the parameter SWITCH_ASSIGNTHRESHOLD during the read RUN.INI file step. Generally, the user is interested in examining those episodes of care where the physician recommends treatment and follow-up services. Therefore, an assignment rule is included that allows the physician to be a key treatment provider, but also allows for the physician to refer to another specialist for ongoing treatment. This assignment rule specifies that when a physician incurs a given percent of charges in an episode of care, that episode is assigned to that physician.

For the physician efficiency analysis, an assignment value of 20% usually is employed, but the user can change the assignment rule from 1-100% using the parameter SWITCH_ASSIGNTHRESHOLD in the RUN.INI file (refer to Table 6).

Using this rule, all professional charges are added in each episode of care, including office visits, lab/path services, medical and surgical procedures, and diagnostic tests. These professional charges may occur on an office visit, clinic, hospital outpatient, hospital inpatient, or other professional setting basis (e.g., nursing home, halfway home, home visit professional charges). All facility charges and prescription drugs are excluded. However, in an embodiment, other services may be included from an episode of care for the physician assignment rule.

For example, consider an assignment rule equal to 20%. This means that when a physician has 20% or more of all professional charges, the episode is assigned to that physician. At the 20% level, this rule generally results in episodes being assigned to about 1.20 physicians (or up to 20% of episodes may be assigned to more than one physician). Chronic disease episodes (e.g., asthma) are assigned to more than one physician more often than acute episodes (e.g., acute bronchitis).

When an episode is not assigned to any physician using the 20% assignment rule, another rule is employed which assigns that episode to the physician who has the highest percent of professional charges within the episode. For example, using the 20% assignment rule, if no physician has 20% or more of the professional charges, and the physician who comes closest to meeting this rule has 17% of professional charges in the episode of interest, then the episode is assigned to this physician and no other.

The third function of the PATAN output process is to group CLIs in episodes into 11 major service categories and 21 sub-service categories. During the extract core claims data fields step, a BETOS code is assigned to each service on a CLI (e.g., CPT-4, HCPCS). The BETOS code assignment allows for CLIs to be grouped into one of 11 major service categories and 21 sub-service categories. Table 24 presents the type of service codes that match to each BETOS code. Then, the type of service codes are mapped to the 11 major service and 21 sub-service categories. Service and sub-service categories are formed during the PATAN output process.

TABLE 24

Type of Service Codes and BETOS Codes

| Type Of Service Code Used for Processing | Service Category | Type of Service Code | BETOS Code |
| --- | --- | --- | --- |
| 0 | Other Medical Services | Unknown | — |
| 1 | Professional Visits | Office Visit | M1x |
| 2 | Professional Visits | Hospital Visit | M2x |
| 3 | Professional Visits | ER Visit | M3 |
| 4 | Professional Visits | Other Visit | M4x, M5x, M6 |
| 5 | Other Medical Services | Anesthesia | P0 |
| 6 | Med/Surg Procedures | Procedure | P1x, P2x, P3x, P4x, P5x, P6x |
| 7 | Other Medical Services | Radiation Therapy | P7A |
| 8 | Other Medical Services | Other Oncology | P7B |
| 9 | Med/Surg Procedures | Endoscopy | P8x |
| 10 | Other Medical Services | Dialysis Service | P9x |
| 11 | Diagnostic Tests | Imaging | Ixx |
| 12 | Other Medical Services | Venipuncture | T1A |
| 13 | Lab/Path | Lab Test | T1B, T1C, T1D, T1E, T1F, T1G, T1H |
| 14 | Diagnostic Tests | Functional Tests | T2x |
| 15 | Other Medical Services | Durable Medical Equipment/Supplies | Dxx |
| 16 | Other Medical Services | Ambulance | O1A |
| 17 | Other Medical Services | Chiropractic | O1B |
| 18 | Other Medical Services | Enteral/Parenteral | O1C |

TABLE 24-continued

Type of Service Codes and BETOS Codes

| Type Of Service Code Used for Processing | Service Category | Type of Service Code | BETOS Code |
|---|---|---|---|
| 19 | Other Medical Services | Chemotherapy | O1D |
| 20 | Other Medical Services | Other Drugs | O1E |
| 21 | Other Medical Services | Vision/hearing/ speech Services | O1F |
| 22 | Other Medical Services | Immunization | O1G |
| 23 | Other Medical Services | Other NEC Services | Y1, Y2, Z1, Z2 |

The fourth function of the PATAN output process is to implement the maximum duration rule for episodes of care, which is 180 days.

For chronic conditions (e.g., diabetes, asthma, ischemic heart disease), an episode of care begins when a CLI is initially found during the study period that has a defined ICD.9 code that has been assigned to that medical condition. Then, chronic conditions may continue on indefinitely as recognized by the window period of 365 days. However, for the purposes of physician efficiency analysis, chronic conditions are considered to have a 180-day duration. Therefore, a chronic condition ends 180 days after identifying the first CLI with a diagnosis (defined ICD.9 code) for the specific chronic condition. The rule determines that the patient is present for 180 days during the study period after the first CLI with a diagnosis for the specific chronic condition.

For acute conditions (e.g., upper respiratory infections, otitis media, conjunctivitis), the maximum allowable duration for the physician efficiency analysis also is 180 days. The embodiment recognizes that this maximum allowable duration may be varied.

Step 7: Store PATAN Output File

The PATAN Output File is stored in episode of care identifier order (Field 1 in Table 25). Table 25 lists the fields present on the PATAN Output File.

TABLE 25

Fields in the PATAN Output File

| Field Number | Field Descriptive Name | Notes |
|---|---|---|
| (Section A) Non-Repeated Episode Fields | | |
| 1 | Episode ID | The unique episode ID for each medical condition treatment episode. |
| 2 | Medical Condition Number | The medical condition internal ID number. |
| 3 | SOI | Severity of Illness index, where 1 is the least severe and 3 is the most severe or difficult to treat as defined for the medical condition. |
| 4 | Episode Duration | The duration of the medical condition treatment episode, in days. |
| 5 | Total Episode Charges | The total allowed charges for the treatment episode, in dollars. |
| 6 | Professional Charges | Total allowed charges claimed by professional (excludes Rx and facility) physicians. |
| 7 | Physician ID | Identifies each physician that had significant involvement in the treatment for the episode. If multiple physicians were significantly involved in treating the episode, multiple rows are output for the episode, one for each physician. |
| 8 | Physician Specialty | Identifies the specialty number associated with the physician. Since the specialty is determined by the PROVSPEC module, this field contains the value 0 in the version of the output from PATAN. |
| 9 | Physician Marketbasket | Identifies the marketbasket number associated with the physician. Since the marketbasket is determined by the PROVSPEC module, this field contains the value 0 in the version of the output from PATAN. |
| 10 | Physician Aggregate Grouping Code Number | Identifies the aggregate grouping number associated with the physician. Since the aggregate grouping number is determined by the PROVSPEC module, this field contains the value 0 in the version of the output from PATAN. |
| 11 | [not valid for commercial population] | This field is not valid for the commercial population. Always contains the value 1. |
| 12 | Physician Charges | The is the charge component amount of the Professional Charges field (see above referenced field) that is attributable to the physician identified by the Physician ID field (see above referenced field). |
| 13 | Patient Age | The age of the patient at the beginning of the study period. |
| (Section B) Repeated Episode Fields for Each Service Category (11 times per row) | | |
| 1 | Service Category Utilization | Eleven fields that contain utilization data at the service category level. |
| 2 | Service Category Charges | Eleven fields, ten of which contain charges in dollars at the service category level (field 9 is not used because the system of the present invention does not break out charge data for inpatient admits). |
| (Section C) Repeated Episode Fields for Each Sub-Service Category (21 times per row) | | |
| 1 | Sub-Service Category Utilization | Twenty-one fields that contain utilization data at the sub-service category level. |

TABLE 25-continued

Fields in the PATAN Output File

| Field Number | Field Descriptive Name | Notes |
|---|---|---|
| 2 | Sub-Service Category Charges | Twenty-one fields, twenty of which contain charges in dollars at the sub-service category level (field 14 is not used because the system of the present invention does not break out charge data for inpatient admits). |

Step 8: Sort PATAN Output File by Provider ID: PROVSORT1

The PATAN Output File is sorted by the primary sort key of physician identifier. The secondary sort key is the episodes assigned to a physician.

Step 9: Read in Episode Assignments from PROVSORT1

The episode assignments by physician from PROVSORT1 are read into the physician specialty module (PROVSPEC). PROVSPEC completes several of the missing fields in the PATAN Output File (refer to Table 25): (1) physician specialty (Field 8); (2) physician marketbasket (Field 9); and (3) physician aggregate grouping code number (Field 10).

Step 10: Assign Specialty Type to Physician

The PROVSPEC module employs a rule to select the most appropriate physician specialty when a physician has more than one specialty type assigned in the physician provider file. This processing step is helpful in selecting a specialty type that is most reflective of the physician's actual practice during the study period.

The rule examines all episodes associated with a physician and assigns each episode to one of the 31 marketbasket specialty types (refer to Table 26). A marketbasket consists of the most common conditions treated by each physician specialty type. The term physician is used broadly, and includes other professionals delivering medical care services, such as chiropractors, acupuncturists, podiatrists, nurse practitioners, and physical therapists.

Medical conditions are tracked to a specialty-specific marketbasket if they generally account for 60% to 80% of the episodes treated by that specialist type. The medical conditions are selected for the marketbasket in work effort order, which is a function of the prevalence rate of a condition and the average charges to treat a patient's episode of care. The embodiment recognizes that additional marketbaskets may be developed for other specialty types.

Several examples of medical conditions in special-specific marketbaskets are as follows. Hypertension, low back pain, and sinusitis are within the general internist marketbasket. Otitis media, upper respiratory infections, sinusitis, and rhinitis are within the pediatric marketbasket. Obstetrics/gynecology: single newborn normal delivery, cervicitis, and endometriosis are within the obstetrics/gynecology marketbasket. External abdominal hernias, cholilithiasis, and cystic breast disease are within the general surgeon marketbasket.

The composition of medical conditions in each specialty-specific marketbasket does not (generally) change over time. This means that any trend increase reflected by the specialty-specific marketbasket is independent of changes in patient demographics and health status. Instead, the trend reflects price increases, volume increases, and intensity of service increases in the treatment of the static set of medical conditions.

The physician specialty assignment rule eliminates any specialty types not already assigned to the physician in the physician provider file. The rule then looks for the marketbaskets with the most episodes among those remaining. For example, consider a physician who has been identified in the physician provider file as a general internist and a cardiologist. During analysis, the rule finds the following marketbasket specialty types associated with the physician's episodes: 37% of episodes are associated with Marketbasket 10, gastroenterology; 34% with Marketbasket 2, general internists; and 29% with Marketbasket 4, cardiology.

Even though 37% of the physician's episodes have been identified as gastroenterology, the physician cannot be assigned to the gastroenterology marketbasket because gastroenterology was not included as a specialty type in the physician provider file.

The physician is observed to have more episodes in the general internists marketbasket than in the cardiology marketbasket. Thus, this physician might be assigned for efficiency analysis into the general internists marketbasket. However, a second rule is now applied before assigning this physician as a general internist and running the general internists marketbasket. The second rule states that if a physician has an assigned primary care physician (PCP) designation (i.e., family/general practitioner, general internist, or pediatrician), but also an assigned non-PCP specialty type, then the PCP designation is ignored and the physician is assigned to the specialty that has the next most episodes that is not a PCP designation. If another specialty type is not present, then the physician is assigned the PCP designation of family/general practitioner, general internist, or pediatrician as defined in the physician provider file.

Using this rule, the physician would be placed in Marketbasket 4, cardiology, because general internist is defined as a PCP. Therefore, the rules assign the physician for efficiency analysis as a cardiologist.

TABLE 26

Marketbasket Specialty Types

| Market-Basket Number | Marketbasket Specialty Type |
|---|---|
| 1 | Family and General Physicians |
| 2 | General Internists |
| 3 | Allergy |
| 4 | Cardiology |
| 5 | Cardiothoracic Surgery |
| 6 | Chiropractic |
| 7 | Dermatology |
| 8 | Emergency Medicine |
| 9 | Endocrinology |
| 10 | Gastroenterology |
| 11 | General Surgery |
| 12 | Nephrology |
| 13 | Neurology |
| 14 | Neurosurgery |
| 15 | Obstetrics/Gynecology (OB/GYN) |
| 16 | Oncology/Hematology |
| 17 | Ophthalmology |

TABLE 26-continued

Marketbasket Specialty Types

| Market-Basket Number | Marketbasket Specialty Type |
|---|---|
| 18 | Oral Maxillary |
| 19 | Orthopedics |
| 20 | Otolaryngology (ENT) |
| 21 | Pediatrics |
| 22 | Plastic Surgery |
| 23 | Podiatry |
| 24 | Psychiatry |
| 25 | Psychology |
| 26 | Pulmonology |
| 27 | Rheumatology |
| 28 | Sports/Physical Medicine |
| 29 | Urology |
| 30 | Vascular Surgery |
| 31 | Critical Care (Intensivist) |

Step 11: Assign Physician to Marketbasket Based on Specialty Type

After the physician has been assigned to a specialty type, the physician is then assigned to a marketbasket. The physician specialty codes in Table 3 are mapped to the marketbasket specialty types in Table 26. Both Table 3 and Table 26 are accessed to assign physicians to a marketbasket.

Step 12: Assign Physician to Report Group

Report group structures are important because they allow the formation of peer groups to which physicians can be compared. PROVSPEC provides a tool to build report group structures that interest the user. The tool provides flexibility in building report groups reflecting comparisons that are relevant to the user. Example report groups include geographic regions, physician groups, and benefit plan designs.

The basis for creating report groups is the Detailed Grouping Code (refer to Table 1, Field 35). A Detailed Grouping Code is a client-specified identifier that is the base data element aggregated to form a report group. For example, zip codes or tax identification numbers can be Detailed Grouping Codes.

An Aggregate Grouping Code represents a group of Detailed Grouping Codes (refer to Table 25, Section A, Field 10). The Aggregate Grouping Code is a number the user chooses. The output of the system of the present invention contains information organized by Aggregate Grouping Code. Therefore, the aggregate groups the user develops are the foundation for report group structures contained in output files and printed reports.

The process of developing a report group structure is a now described. First, the user decides on a grouping structure. When formulating a grouping structure, the user needs to consider the nature of the comparison. For example, one comparison may be geographic comparisons based on zip code of physician place of service. The grouping structure should assure that each group has a large enough member base to make comparisons meaningful.

Second, an Aggregate Grouping Code is assigned to each group that has been defined. The code is a positive integer that has been selected. It is used by the system of the present invention to represent the groups. For example, when comparing on the basis of geographic regions, each Aggregate Grouping Code might represent a specific region that has been defined by identifying individual zip codes.

Detail codes are then determined based on the comparison to be made. For example, for geographic comparisons, the detail codes might be physician office address zip codes.

Each Detailed Grouping Code is then assigned to an Aggregate Grouping Code. The user does this by creating a simple two-column table in which the first column is the Detailed Grouping Code and the second column is the Aggregate Grouping Code. The task is accomplished by developing a spreadsheet for relatively small groups or with a database program for larger groups.

The grouping map is then saved as a file, and referenced in the RUN.INI File. The user may name the file as desired, and the user needs to edit the RUN.INI File so that it includes the correct file name. Output files and reports are organized using the report group structure that has been defined.

A geographic region analysis might use physician office zip codes as the basis for forming groups. The user would employ the following process to build the report group structure: identify the geographic regions of interest; assign each region an arbitrary code number; each physician must then be identified as belonging to a region; and assign or map physician office zip codes to the code numbers representing geographic regions. Table 27 shows how the user can map zip codes to regions.

TABLE 27

Grouping by Geographic Region

| Detailed Grouping Code | Aggregate Grouping Code |
|---|---|
| Physician's office Zip Code | Code number representing a client-defined geographic region |

A physician group analysis might use physician identification numbers as the basis for forming groups. In this embodiment, the user employs the following process to build the report group structure: identify the physician groups of interest; assign each physician group an arbitrary code number; identify each physician as belonging to a group; and assign or map physician identification numbers to the code numbers representing physician groups. Table 28 shows how the user would map physician identification numbers to the code numbers representing physician groups.

TABLE 28

Grouping by Physician Group

| Detailed Grouping Code | Aggregate Grouping Code |
|---|---|
| Physician ID | Number representing a physician group |

Step 13: Determine Eligible Physicians and Episode Assignments

This step involves three main functions. The first function is to filter or eliminate physicians with an assigned specialty type that cannot be assigned to one of the 31 marketbaskets. For example, there is no radiologist marketbasket, so radiologists would be removed by this rule.

The second function is to eliminate physicians that are not in a report group of interest. This rule examines the physician's assigned Detailed Grouping Code as compared to the Aggregate Grouping Codes of Interest. If the Detailed Grouping Code does not match to an Aggregate Grouping Code of interest for an established RUN.INI File run, then the physician is filtered out from further analysis.

The third function is to filter out episode assignments not in a marketbasket. For physicians in a Report Group of interest for an established RUN.INI File run, episode assignment rows in the PROVSORT1 input file that are not relevant to the marketbasket in which the physician will be profiled are filtered by PROVSPEC processing. This PROVSPEC rule checks to ensure that the medical conditions treated by the physician are included in the FILE_MBCONDITIONS File for the physician's marketbasket (refer to Table 6, Parameters in the RUN.INI File). Medical conditions that are not in the physician's marketbasket are removed from analysis.

Another PROVSPEC rule checks to ensure that the age of the patient falls within the age range specified in the FILE_SPECAGE File for a defined marketbasket (refer to Table 6, Parameters in the RUN.INI File). If not, that patient's episode of care is removed from analysis. The user can modify the FILE_SPECAGE File.

With respect to the FILE_MBCONDITIONS File, both commercial and Medicare marketbaskets have been defined. There are a total of 31 commercial marketbaskets by physician specialty type. Commercial means a population of individuals under 65 years of age that are not eligible to receive Medicare benefits. There are a total of 31 Medicare marketbaskets by physician specialty type. Medicare means a population of individuals 65 years of age and older that are eligible to receive Medicare benefits.

Each medical condition in a specialty-specific marketbasket is assigned a weight factor that reflects the importance or relevance of that medical condition to the marketbasket. However, in an embodiment, no one medical condition receives more than a 30% weight factor to prevent a physician's treatment pattern for that condition from dominating the results of a marketbasket.

The weight factors are used to compute the overall marketbasket weighted average value of a charge or utilization service category—across medical conditions—for a peer group or a physician. The sum of the weight factors in a marketbasket equals 1.00.

Therefore, regardless of a physician's (or peer group's) actual episode work effort, the rule standardizes each physician's actual work effort to a static set of weight factors. These weight factors represent the work effort that an average specialty-specific physician treats in medical practice, where work effort is a function of the prevalence rate and the average charges to treat an episode of care. This standardized weighting allows for an apples-to-apples comparison of one physician's marketbasket results to another physician's marketbasket results.

Tables 29-60 present the 31 commercial marketbaskets listed in Table 26, Marketbasket Specialty Types. The last column in each marketbasket table presents the weight factor for each medical condition. It is to be understood that the medical conditions and severity-of-illness levels may change for a marketbasket.

TABLE 29

| | 1. FAMILY AND GENERAL PRACTITIONERS | | | |
|---|---|---|---|---|
| Order Number | Medical Condition Number | SOI Level | Medical Condition Short Description | Marketbasket Weight |
| 1 | 10.2 | 1 | Hypertension | 0.100 |
| 2 | 31.9 | 1 | Low back pain | 0.050 |
| 3 | 31.8 | 1 | Cervical spine pain | 0.025 |
| 4 | 31.4 | 1 | Bursitis | 0.050 |
| 5 | 33.15 | 1 | Degenerative joint disease | 0.025 |
| 6 | 17.1 | 1 | Diabetes w/no complications | 0.050 |
| 7 | 7.2 | 1 | Sinusitis | 0.050 |
| 8 | 7.1 | 1 | Rhinitis | 0.050 |

TABLE 29-continued

| | 1. FAMILY AND GENERAL PRACTITIONERS | | | |
|---|---|---|---|---|
| Order Number | Medical Condition Number | SOI Level | Medical Condition Short Description | Marketbasket Weight |
| 9 | 9.4 | 1 | Acute bronchitis | 0.050 |
| 10 | 9.1 | 1 | Upper respiratory infections | 0.050 |
| 11 | 9.7 | 1 | Pneumonia | 0.050 |
| 12 | 13.13 | 1 | Noninfect gastroent & colitis | 0.050 |
| 13 | 9.11 | 1 | Asthma | 0.025 |
| 14 | 10.13 | 1 | Ischemic heart disease | 0.025 |
| 15 | 36.19 | 1 | Chest pain | 0.025 |
| 16 | 13.6 | 1 | Gastroesophageal reflux | 0.025 |
| 17 | 13.5 | 1 | Gastritis and duodenitis | 0.025 |
| 18 | 19.4 | 1 | Disorders of lipid metabolism | 0.025 |
| 19 | 16.3 | 1 | Hypothyroidism | 0.025 |
| 20 | 22.3 | 1 | Urinary tract infections | 0.025 |
| 21 | 34.17 | 1 | Nonpsychotic depression | 0.025 |
| 22 | 34.14 | 1 | Personality & disturb dsdr | 0.025 |
| 23 | 29.9 | 1 | Dermatitis and eczema | 0.025 |
| 24 | 4.3 | 1 | Headaches | 0.020 |
| 25 | 31.3 | 1 | Other arthropathy disorders | 0.020 |
| 26 | 20.4 | 1 | Anemia disorders | 0.020 |
| 27 | 36.17 | 1 | Abdominal pain | 0.020 |
| 28 | 29.6 | 1 | Skin keratoses | 0.015 |
| 29 | 29.1 | 1 | Ill-defined integument sym | 0.015 |
| 30 | 36.15 | 1 | General presenting symptoms | 0.015 |
| | | | | 1.000 |

TABLE 30

| | 2. GENERAL INTERNISTS | | | |
|---|---|---|---|---|
| Order Number | Medical Condition Number | SOI Level | Medical Condition Short Description | Marketbasket Weight |
| 1 | 10.2 | 1 | Hypertension | 0.100 |
| 2 | 31.9 | 1 | Low back pain | 0.050 |
| 3 | 31.8 | 1 | Cervical spine pain | 0.025 |
| 4 | 31.4 | 1 | Bursitis | 0.050 |
| 5 | 33.15 | 1 | Degenerative joint disease | 0.025 |
| 6 | 17.1 | 1 | Diabetes w/no complications | 0.050 |
| 7 | 7.2 | 1 | Sinusitis | 0.050 |
| 8 | 7.1 | 1 | Rhinitis | 0.050 |
| 9 | 9.4 | 1 | Acute bronchitis | 0.050 |
| 10 | 9.1 | 1 | Upper respiratory infections | 0.050 |
| 11 | 9.7 | 1 | Pneumonia | 0.050 |
| 12 | 13.13 | 1 | Noninfect gastroent & colitis | 0.050 |
| 13 | 9.11 | 1 | Asthma | 0.025 |
| 14 | 10.13 | 1 | Ischemic heart disease | 0.025 |
| 15 | 36.19 | 1 | Chest pain | 0.025 |
| 16 | 13.6 | 1 | Gastroesophageal reflux | 0.025 |
| 17 | 13.5 | 1 | Gastritis and duodenitis | 0.025 |
| 18 | 19.4 | 1 | Disorders of lipid metabolism | 0.025 |
| 19 | 16.3 | 1 | Hypothyroidism | 0.025 |
| 20 | 22.3 | 1 | Urinary tract infections | 0.025 |
| 21 | 34.17 | 1 | Nonpsychotic depression | 0.025 |
| 22 | 34.14 | 1 | Personality & disturb dsdr | 0.025 |
| 23 | 29.9 | 1 | Dermatitis and eczema | 0.025 |
| 24 | 4.3 | 1 | Headaches | 0.020 |
| 25 | 31.3 | 1 | Other arthropathy disorders | 0.020 |
| 26 | 20.4 | 1 | Anemia disorders | 0.020 |
| 27 | 36.17 | 1 | Abdominal pain | 0.020 |
| 28 | 29.6 | 1 | Skin keratoses | 0.015 |
| 29 | 29.1 | 1 | Ill-defined integument sym | 0.015 |
| 30 | 36.15 | 1 | General presenting symptoms | 0.015 |
| | | | | 1.000 |

TABLE 31

3. ALLERGY

| Order Number | Medical Condition Number | SOI Level | Medical Condition Short Description | Market-basket Weight |
|---|---|---|---|---|
| 1 | 7.1 | 1 | Rhinitis | 0.175 |
| 2 | 7.2 | 1 | Sinusitis | 0.150 |
| 3 | 9.11 | 1 | Asthma | 0.150 |
| 4 | 9.1 | 1 | Upper respiratory infections | 0.075 |
| 5 | 9.2 | 1 | Dz upper respiratory tract | 0.050 |
| 6 | 9.10 | 1 | Chronic bronchitis | 0.050 |
| 7 | 9.4 | 1 | Acute bronchitis | 0.050 |
| 8 | 7.4 | 1 | Deviated nasal septum | 0.050 |
| 9 | 9.3 | 1 | Lower respiratory diseases | 0.050 |
| 10 | 29.8 | 1 | Urticaria | 0.050 |
| 11 | 36.12 | 1 | Toxic effects of substances | 0.050 |
| 12 | 29.9 | 1 | Dermatitis and eczema | 0.025 |
| 13 | 5.2 | 1 | Conjunctivitis | 0.025 |
| 14 | 6.5 | 1 | Otitis media | 0.025 |
| 15 | 9.5 | 1 | Hypertrophy tonsils & aden | 0.025 |
| | | | | 1.000 |

TABLE 32

4. CARDIOLOGY

| Order Number | Medical Condition Number | SOI Level | Medical Condition Short Description | Market-basket Weight |
|---|---|---|---|---|
| 1 | 10.13 | 1 | Ischemic heart disease | 0.150 |
| 2 | 10.13 | 2 | Ischemic heart disease | 0.050 |
| 3 | 17.4 | 1 | Diabetes with circulatory | 0.050 |
| 4 | 17.4 | 2 | Diabetes with circulatory | 0.050 |
| 5 | 10.21 | 1 | Acute myocardial infrct, active | 0.075 |
| 6 | 10.22 | 1 | Acute myocardial infrct, fup | 0.025 |
| 7 | 10.2 | 1 | Hypertension | 0.075 |
| 8 | 10.5 | 1 | Supraventricular arrhythmias | 0.050 |
| 9 | 10.4 | 1 | Ventricular arrhythmias | 0.050 |
| 10 | 10.1 | 1 | Abnormal heart beat | 0.050 |
| 11 | 10.14 | 1 | Heart value disorders | 0.050 |
| 12 | 36.19 | 1 | Chest pain | 0.050 |
| 13 | 10.10 | 1 | Conduction disorders | 0.050 |
| 14 | 10.16 | 1 | Congestive heart failure | 0.050 |
| 15 | 10.17 | 1 | Cardiomyopathy | 0.050 |
| 16 | 19.4 | 1 | Disorders of lipid metabolism | 0.025 |
| 17 | 10.11 | 1 | Other heart disease | 0.025 |
| 18 | 10.8 | 1 | Angina pectoris | 0.025 |
| 19 | 10.12 | 1 | Rheumatic heart disease | 0.025 |
| 20 | 36.18 | 1 | Dyspnea | 0.025 |
| | | | | 1.000 |

TABLE 33

5. CARDIOTHORACIC SURGERY

| Order Number | Medical Condition Number | SOI Level | Medical Condition Short Description | Market-basket Weight |
|---|---|---|---|---|
| 1 | 10.13 | 1 | Ischemic heart disease | 0.175 |
| 2 | 10.13 | 2 | Ischemic heart disease | 0.025 |
| 3 | 10.21 | 1 | Acute myocardial infrct, active | 0.100 |
| 4 | 10.22 | 1 | Acute myocardial infrct, fup | 0.025 |
| 5 | 17.4 | 1 | Diabetes with circulatory | 0.050 |
| 6 | 17.4 | 2 | Diabetes with circulatory | 0.025 |
| 7 | 9.12 | 1 | Benign neop bronchus & lung | 0.050 |
| 8 | 9.19 | 1 | Malig neop bron/lung, active | 0.050 |
| 9 | 11.8 | 1 | Generalized arteriosclerosis | 0.050 |
| 10 | 12.5 | 1 | Varicose veins lower extrem | 0.050 |
| 11 | 9.9 | 1 | Pleurisy | 0.050 |
| 12 | 9.15 | 1 | Spon pneumothorax | 0.050 |
| 13 | 10.12 | 1 | Rheumatic heart disease | 0.050 |
| 14 | 10.10 | 1 | Conduction disorders | 0.025 |
| 15 | 10.14 | 1 | Heart value disorders | 0.025 |
| 16 | 10.19 | 1 | Aortic aneurysm, initial | 0.025 |
| 17 | 10.20 | 1 | Aortic aneurysm, fup | 0.025 |
| 18 | 10.16 | 1 | Congestive heart failure | 0.025 |
| 19 | 10.17 | 1 | Cardiomyopathy | 0.025 |
| 20 | 11.7 | 1 | Disorders of arteries | 0.025 |
| 21 | 15.4 | 1 | Cholelithiasis | 0.025 |
| 22 | 30.2 | 1 | Cystic breast disease | 0.025 |
| 23 | 11.12 | 1 | Occlusion of cerebral arteries | 0.025 |
| | | | | 1.000 |

TABLE 34

6. CHIROPRACTIC

| Order Number | Medical Condition Number | SOI Level | Medical Condition Short Description | Market-basket Weight |
|---|---|---|---|---|
| 1 | 31.9 | 1 | Low back pain | 0.225 |
| 2 | 31.9 | 2 | Low back pain | 0.075 |
| 3 | 31.6 | 1 | Nonallopathic lesions | 0.150 |
| 4 | 31.6 | 2 | Nonallopathic lesions | 0.050 |
| 5 | 31.8 | 1 | Cervical spine pain | 0.150 |
| 6 | 31.8 | 2 | Cervical spine pain | 0.050 |
| 7 | 31.3 | 1 | Other arthropathy disorders | 0.100 |
| 8 | 4.7 | 1 | Nerve root and plexus dsdr | 0.050 |
| 9 | 31.13 | 1 | Minor injury of trunk | 0.050 |
| 10 | 31.12 | 1 | Scoliosis | 0.025 |
| 11 | 33.15 | 1 | Degenerative joint disease | 0.025 |
| 12 | 31.4 | 1 | Bursitis | 0.025 |
| 13 | 4.1 | 1 | Neuritis upper, lower limbs | 0.025 |
| | | | | 1.000 |

TABLE 35

7. DERMATOLOGY

| Order Number | Medical Condition Number | SOI Level | Medical Condition Short Description | Market-basket Weight |
|---|---|---|---|---|
| 1 | 29.17 | 1 | Acne | 0.125 |
| 2 | 29.19 | 1 | Benign neoplasm of skin | 0.075 |
| 3 | 29.9 | 1 | Dermatitis and eczema | 0.075 |
| 4 | 29.23 | 1 | Psoriasis and pityriasis | 0.075 |
| 5 | 29.26 | 1 | Other malignancy of skin | 0.075 |
| 6 | 29.14 | 1 | Dermatophytoses | 0.050 |
| 7 | 2.9 | 1 | Viral warts | 0.050 |
| 8 | 29.6 | 1 | Skin keratoses | 0.050 |
| 9 | 29.13 | 1 | Rosacea | 0.050 |
| 10 | 30.1 | 1 | Inflammatory disease of breast | 0.050 |
| 11 | 29.21 | 1 | Dz of hair and hair follicles | 0.050 |
| 12 | 29.5 | 1 | Other dsdr skin/subcutan tiss | 0.025 |
| 13 | 29.15 | 1 | Sebaceous cyst | 0.025 |
| 14 | 29.24 | 1 | Carcinoma in situ of skin | 0.025 |
| 15 | 29.8 | 1 | Urticaria | 0.025 |
| 16 | 29.22 | 1 | Erythematous condition | 0.025 |
| 17 | 21.2 | 1 | Hemangioma | 0.025 |
| 18 | 29.10 | 1 | Cellul & abscess, finger/toe | 0.025 |
| 19 | 2.8 | 1 | Herpes simplex | 0.025 |

TABLE 35-continued

7. DERMATOLOGY

| Order Number | Medical Condition Number | SOI Level | Medical Condition Short Description | Market-basket Weight |
|---|---|---|---|---|
| 20 | 29.28 | 1 | Malig melanoma of skin, initial | 0.025 |
| 21 | 29.20 | 1 | Dz of nail, excluding infections | 0.025 |
| 22 | 11.1 | 1 | Pigmented nevus | 0.025 |
| | | | | 1.000 |

TABLE 36

8. EMERGENCY MEDICINE

| Order Number | Medical Condition Number | SOI Level | Medical Condition Short Description | Market-basket Weight |
|---|---|---|---|---|
| 1 | 32.5 | 1 | Open wound hand & fingers | 0.075 |
| 2 | 8.5 | 1 | Open wound face & mouth | 0.075 |
| 3 | 36.19 | 1 | Chest pain | 0.050 |
| 4 | 11.3 | 1 | Contusion of head and neck | 0.050 |
| 5 | 11.5 | 1 | Cerebral laceration | 0.025 |
| 6 | 11.4 | 1 | Concussion | 0.025 |
| 7 | 32.13 | 1 | Fracture of radius and ulna | 0.050 |
| 8 | 32.11 | 1 | Fracture of hand bones | 0.050 |
| 9 | 32.1 | 1 | Contusion of upper limb | 0.050 |
| 10 | 33.2 | 1 | Sprain/strain of foot and ankle | 0.050 |
| 11 | 33.1 | 1 | Contusion of lower limb | 0.050 |
| 12 | 33.6 | 1 | Open wound of leg | 0.050 |
| 13 | 33.22 | 1 | Derangement of knee | 0.025 |
| 14 | 13.13 | 1 | Noninfect gastroent & colitis | 0.050 |
| 15 | 9.1 | 1 | Upper respiratory infections | 0.050 |
| 16 | 9.4 | 1 | Acute bronchitis | 0.025 |
| 17 | 36.17 | 1 | Abdominal pain | 0.025 |
| 18 | 31.9 | 1 | Low back pain | 0.025 |
| 19 | 31.8 | 1 | Cervical spine pain | 0.025 |
| 20 | 31.4 | 1 | Bursitis | 0.025 |
| 21 | 10.22 | 1 | Acute myocardial infrct, fup | 0.025 |
| 22 | 17.1 | 1 | Diabetes w/no complications | 0.025 |
| 23 | 4.3 | 1 | Headaches | 0.020 |
| 24 | 9.11 | 1 | Asthma | 0.020 |
| 25 | 10.2 | 1 | Hypertension | 0.020 |
| 26 | 22.11 | 1 | Calculus of kidney and ureter | 0.020 |
| 27 | 15.4 | 1 | Cholelithiasis | 0.020 |
| | | | | 1.000 |

TABLE 37

9. ENDOCRINOLOGY

| Order Number | Medical Condition Number | SOI Level | Medical Condition Short Description | Market-basket Weight |
|---|---|---|---|---|
| 1 | 25.2 | 1 | Infertility female | 0.175 |
| 2 | 23.10 | 1 | Endometriosis | 0.125 |
| 3 | 17.1 | 1 | Diabetes w/no complications | 0.125 |
| 4 | 17.2 | 1 | Diabetes with ophthalmic | 0.050 |
| 5 | 16.3 | 1 | Hypothyroidism | 0.075 |
| 6 | 16.4 | 1 | Hyperthyroidism | 0.050 |
| 7 | 16.2 | 1 | Goiter | 0.050 |
| 8 | 23.7 | 1 | Menstrual disorders | 0.050 |
| 9 | 23.6 | 1 | Ovarian dysfunction | 0.050 |
| 10 | 23.11 | 1 | Ovarian cyst | 0.025 |
| 11 | 19.4 | 1 | Disorders of lipid metabolism | 0.050 |
| 12 | 19.4 | 2 | Disorders of lipid metabolism | 0.025 |
| 13 | 18.1 | 1 | Other endocrine disorders | 0.025 |
| 14 | 19.6 | 1 | Other disorders of metabolism | 0.025 |
| 15 | 18.3 | 1 | Disorders of pituitary gland | 0.025 |
| 16 | 18.4 | 1 | Benign neop of pituitary gland | 0.025 |

TABLE 37-continued

9. ENDOCRINOLOGY

| Order Number | Medical Condition Number | SOI Level | Medical Condition Short Description | Market-basket Weight |
|---|---|---|---|---|
| 17 | 18.2 | 1 | Disorders of adrenal gland | 0.025 |
| 18 | 10.2 | 1 | Hypertension | 0.025 |
| | | | | 1.000 |

TABLE 38

10. GASTROENTEROLOGY

| Order Number | Medical Condition Number | SOI Level | Medical Condition Short Description | Market-basket Weight |
|---|---|---|---|---|
| 1 | 13.13 | 1 | Noninfect gastroent & colitis | 0.125 |
| 2 | 13.9 | 1 | Irritable colon | 0.050 |
| 3 | 13.6 | 1 | Gastroesophageal reflux | 0.100 |
| 4 | 13.4 | 1 | Other disorders of esophagus | 0.050 |
| 5 | 13.17 | 1 | Benign neop colon/rectum | 0.075 |
| 6 | 13.5 | 1 | Gastritis and duodenitis | 0.075 |
| 7 | 13.20 | 1 | Crohn's disease | 0.075 |
| 8 | 13.10 | 1 | Peptic ulcer | 0.075 |
| 9 | 13.11 | 1 | Diverticula of intestine | 0.050 |
| 10 | 13.21 | 1 | Gastrointestinal hemorrhage | 0.050 |
| 11 | 13.12 | 1 | Other diseases of intestine | 0.050 |
| 12 | 12.2 | 1 | Hemorrhoids | 0.050 |
| 13 | 14.2 | 1 | Diaphragmatic hernia | 0.025 |
| 14 | 13.8 | 1 | Dsdr stomach & duodenum | 0.025 |
| 15 | 13.7 | 1 | Functional digestive diseases | 0.025 |
| 16 | 15.7 | 1 | Hepatitis | 0.020 |
| 17 | 15.10 | 1 | Chronic liver disease | 0.020 |
| 18 | 15.9 | 1 | Diseases of pancreas | 0.020 |
| 19 | 15.4 | 1 | Cholelithiasis | 0.020 |
| 20 | 36.17 | 1 | Abdominal pain | 0.020 |
| | | | | 1.000 |

TABLE 39

11. GENERAL SURGERY

| Order Number | Medical Condition Number | SOI Level | Medical Condition Short Description | Market-basket Weight |
|---|---|---|---|---|
| 1 | 14.3 | 1 | External abdominal hernias | 0.125 |
| 2 | 15.4 | 1 | Cholelithiasis | 0.125 |
| 3 | 30.1 | 1 | Inflammatory disease of breast | 0.075 |
| 4 | 30.2 | 1 | Cystic breast disease | 0.050 |
| 5 | 30.3 | 1 | Benign neoplasm of breast | 0.050 |
| 6 | 12.2 | 1 | Hemorrhoids | 0.050 |
| 7 | 29.15 | 1 | Sebaceous cyst | 0.050 |
| 8 | 29.18 | 1 | Lipoma | 0.050 |
| 9 | 13.14 | 1 | Appendicitis | 0.050 |
| 10 | 30.8 | 1 | Malig neop of breast, initial | 0.050 |
| 11 | 30.10 | 1 | Malig neop of breast, fup | 0.025 |
| 12 | 12.1 | 1 | Anal fissure and fistula | 0.050 |
| 13 | 13.17 | 1 | Benign neop colon/rectum | 0.025 |
| 14 | 13.13 | 1 | Noninfect gastroent & colitis | 0.025 |
| 15 | 13.18 | 1 | Intestinal obstruction | 0.025 |
| 16 | 13.12 | 1 | Other diseases of intestine | 0.025 |
| 17 | 29.19 | 1 | Benign neoplasm of skin | 0.025 |
| 18 | 12.5 | 1 | Varicose veins lower extrem | 0.025 |
| 19 | 29.16 | 1 | Pilonidal cyst | 0.020 |
| 20 | 29.6 | 1 | Skin keratoses | 0.020 |
| 21 | 2.9 | 1 | Viral warts | 0.020 |
| 22 | 13.30 | 1 | Malig neop of colon, initial | 0.020 |
| 23 | 29.26 | 1 | Other malignancy of skin | 0.020 |
| | | | | 1.000 |

TABLE 40

12. NEPHROLOGY

| Order Number | Medical Condition Number | SOI Level | Medical Condition Short Description | Market-basket Weight |
|---|---|---|---|---|
| 1 | 22.15 | 1 | Renal failure | 0.150 |
| 2 | 22.15 | 2 | Renal failure | 0.075 |
| 3 | 17.5 | 1 | Diabetes with renal | 0.100 |
| 4 | 17.5 | 2 | Diabetes with renal | 0.075 |
| 5 | 22.12 | 1 | Glomerulonephritis | 0.075 |
| 6 | 10.2 | 1 | Hypertension | 0.075 |
| 7 | 22.9 | 1 | Cong anom kidney and ureter | 0.075 |
| 8 | 22.10 | 1 | Disorders of kidney and ureter | 0.075 |
| 9 | 22.17 | 1 | Kidney transplant, follow-up | 0.050 |
| 10 | 19.2 | 1 | Dsdr of fluids and electrolytes | 0.050 |
| 11 | 22.11 | 1 | Calculus of kidney and ureter | 0.050 |
| 12 | 19.4 | 1 | Disorders of lipid metabolism | 0.050 |
| 13 | 19.6 | 1 | Other disorders of metabolism | 0.050 |
| 14 | 22.3 | 1 | Urinary tract infections | 0.050 |
| | | | | 1.000 |

TABLE 41

13. NEUROLOGY

| Order Number | Medical Condition Number | SOI Level | Medical Condition Short Description | Market-basket Weight |
|---|---|---|---|---|
| 1 | 4.3 | 1 | Headaches | 0.150 |
| 2 | 4.18 | 1 | Seizure disorders | 0.125 |
| 3 | 31.9 | 1 | Low back pain | 0.075 |
| 4 | 31.8 | 1 | Cervical spine pain | 0.050 |
| 5 | 4.5 | 1 | Carpal tunnel syndrome | 0.050 |
| 6 | 4.20 | 1 | Other CNS diseases | 0.075 |
| 7 | 4.19 | 1 | Multiple sclerosis | 0.050 |
| 8 | 4.2 | 1 | Peripheral neuropathy | 0.050 |
| 9 | 4.1 | 1 | Neuritis upper, lower limbs | 0.050 |
| 10 | 6.8 | 1 | Vertiginous syndromes | 0.050 |
| 11 | 4.8 | 1 | Tremor disorders | 0.050 |
| 12 | 4.17 | 1 | Parkinson's disease | 0.025 |
| 13 | 11.12 | 1 | Occulsion of cerebral arteries | 0.025 |
| 14 | 11.10 | 1 | Transient cerebral ischemia | 0.025 |
| 15 | 4.21 | 1 | Muscular dystrophies | 0.025 |
| 16 | 4.12 | 1 | Paralytic syndromes | 0.025 |
| 17 | 4.4 | 1 | Disorders of cranial nerves | 0.025 |
| 18 | 34.20 | 1 | Sleep apnea | 0.025 |
| 19 | 4.14 | 1 | Benign neoplasm of CNS | 0.025 |
| 20 | 31.3 | 1 | Other arthropathy disorders | 0.025 |
| | | | | 1.000 |

TABLE 42

14. NEUROSURGERY

| Order Number | Medical Condition Number | SOI Level | Medical Condition Short Description | Market-basket Weight |
|---|---|---|---|---|
| 1 | 31.9 | 1 | Low back pain | 0.200 |
| 2 | 31.9 | 2 | Low back pain | 0.100 |
| 3 | 31.8 | 1 | Cervical spine pain | 0.125 |
| 4 | 4.5 | 1 | Carpal tunnel syndrome | 0.075 |
| 5 | 4.14 | 1 | Benign neoplasm of CNS | 0.075 |
| 6 | 4.24 | 1 | Malig neop brain, initial | 0.075 |
| 7 | 18.4 | 1 | Benign neop of pituitary gland | 0.050 |
| 8 | 31.21 | 1 | Fracture of vertebra | 0.050 |
| 9 | 11.4 | 1 | Concussion | 0.050 |
| 10 | 4.20 | 1 | Other CNS diseases | 0.050 |
| 11 | 4.16 | 1 | Cong anomalies nerv sys | 0.050 |
| 12 | 31.2 | 1 | Congenital anomalies of spine | 0.050 |
| 13 | 4.4 | 1 | Disorders of cranial nerves | 0.025 |
| 14 | 11.10 | 1 | Transient cerebral ischemia | 0.025 |
| | | | | 1.000 |

TABLE 43

15. OBSTETRICS/GYNECOLOGY (OB/GYN)

| Order Number | Medical Condition Number | SOI Level | Medical Condition Short Description | Market-basket Weight |
|---|---|---|---|---|
| 1 | 26.4 | 1 | Single newborn, normal | 0.225 |
| 2 | 26.5 | 1 | Single newborn, complicated | 0.075 |
| 3 | 23.2 | 1 | Cervicitis and vaginitis | 0.050 |
| 4 | 23.1 | 1 | Disorders of cervix and vagina | 0.050 |
| 5 | 23.9 | 1 | Benign neoplasm of uterus | 0.050 |
| 6 | 1.2 | 1 | Gynecological exam | 0.050 |
| 7 | 23.10 | 1 | Endometriosis | 0.050 |
| 8 | 23.4 | 1 | Other disorders of uterus | 0.025 |
| 9 | 23.5 | 1 | Other dsdr female genital org | 0.050 |
| 10 | 23.7 | 1 | Menstrual disorders | 0.050 |
| 11 | 23.8 | 1 | Menopausal symptoms | 0.050 |
| 12 | 23.11 | 1 | Ovarian cyst | 0.050 |
| 13 | 23.3 | 1 | Uterovaginal prolapse | 0.050 |
| 14 | 25.2 | 1 | Infertility female | 0.025 |
| 15 | 26.3 | 1 | Spont and induced abortions | 0.025 |
| 16 | 25.1 | 1 | Contraceptive management | 0.025 |
| 17 | 30.2 | 1 | Cystic breast disease | 0.025 |
| 18 | 30.1 | 1 | Inflammatory disease of breast | 0.025 |
| 19 | 22.3 | 1 | Urinary tract infections | 0.025 |
| 20 | 2.9 | 1 | Viral warts | 0.025 |
| | | | | 1.000 |

TABLE 44

16. ONCOLOGY/HEMATOLOGY

| Order Number | Medical Condition Number | SOI Level | Medical Condition Short Description | Market-basket Weight |
|---|---|---|---|---|
| 1 | 30.8 | 1 | Malig neop of breast, initial | 0.075 |
| 2 | 30.9 | 1 | Malig neop of breast, active | 0.100 |
| 3 | 30.10 | 1 | Malig neop of breast, fup | 0.050 |
| 4 | 24.9 | 1 | Malig neop of prostate, active | 0.075 |
| 5 | 24.10 | 1 | Malig neop of prostate, inactive | 0.075 |
| 6 | 9.19 | 1 | Malig neop bron/lung, active | 0.075 |
| 7 | 9.20 | 1 | Malig neop bron/lung, inactive | 0.050 |
| 8 | 13.31 | 1 | Malig neop of colon, active | 0.025 |
| 9 | 13.32 | 1 | Malig neop of colon, fup | 0.025 |
| 10 | 20.3 | 1 | Diseases of white blood cells | 0.075 |
| 11 | 20.6 | 1 | Thrombocytopenia | 0.050 |
| 12 | 20.5 | 1 | Aplastic anemias | 0.050 |
| 13 | 20.4 | 1 | Anemia disorders | 0.050 |
| 14 | 20.2 | 1 | Dz of blood forming organs | 0.050 |
| 15 | 21.6 | 1 | Lymphoma, inactive | 0.050 |
| 16 | 21.11 | 1 | Leukemia, inactive | 0.050 |
| 17 | 21.8 | 1 | Hodgkin's disease, inactive | 0.050 |
| 18 | 23.9 | 1 | Benign neoplasm of uterus | 0.025 |
| | | | | 1.000 |

TABLE 46

17. OPHTHALMOLOGY

| Order Number | Medical Condition Number | SOI Level | Medical Condition Short Description | Market-basket Weight |
|---|---|---|---|---|
| 1 | 5.17 | 1 | Cataract | 0.175 |
| 2 | 5.17 | 2 | Cataract | 0.075 |
| 3 | 5.16 | 1 | Glaucoma | 0.100 |
| 4 | 5.16 | 2 | Glaucoma | 0.050 |
| 5 | 5.10 | 1 | Strabismus | 0.075 |
| 6 | 5.20 | 1 | Retinal detach & defects | 0.050 |
| 7 | 5.18 | 1 | Other retinal disorders | 0.050 |
| 8 | 17.2 | 1 | Diabetes with ophthalmic | 0.050 |
| 9 | 5.2 | 1 | Conjunctivitis | 0.050 |
| 10 | 5.3 | 1 | Other dsdr of conjunctiva | 0.025 |
| 11 | 5.4 | 1 | Infections of the eyelids | 0.025 |
| 12 | 5.14 | 1 | Disorders of vitreous body | 0.025 |
| 13 | 5.6 | 1 | Dsdr of lacrimal system | 0.025 |
| 14 | 5.15 | 1 | Other eye disorders | 0.025 |
| 15 | 5.7 | 1 | Keratitis | 0.025 |
| 16 | 5.8 | 1 | Other disorders of cornea | 0.025 |
| 17 | 5.21 | 1 | Blindness & visual disturb | 0.025 |
| 18 | 5.19 | 1 | Macular degeneration | 0.025 |
| 19 | 5.9 | 1 | Dsdr iris and ciliary body | 0.025 |
| 20 | 5.11 | 1 | External eye injury | 0.025 |
| 21 | 5.13 | 1 | Internal eye injury | 0.025 |
| 22 | 5.5 | 1 | Disorders of eyelids | 0.025 |
| | | | | 1.000 |

TABLE 47

18. ORAL MAXILLARY

| Order Number | Medical Condition Number | SOI Level | Medical Condition Short Description | Market-basket Weight |
|---|---|---|---|---|
| 1 | 8.12 | 1 | Diseases of jaw | 0.125 |
| 2 | 8.10 | 1 | TMJ disorder | 0.125 |
| 3 | 8.6 | 1 | Anomalies of jaw size | 0.125 |
| 4 | 8.7 | 1 | Other dentofacial anom | 0.100 |
| 5 | 8.4 | 1 | Disorders of teeth | 0.100 |
| 6 | 8.14 | 1 | Diseases of oral soft tissue | 0.075 |
| 7 | 8.16 | 1 | Jaw fracture | 0.075 |
| 8 | 8.5 | 1 | Open wound face & mouth | 0.075 |
| 9 | 8.13 | 1 | Diseases of salivary glands | 0.050 |
| 10 | 8.15 | 1 | Benign neop of oral cavity | 0.050 |
| 11 | 8.9 | 1 | Other dz supporting struct | 0.050 |
| 12 | 8.2 | 1 | Cong anomalies oral cavity | 0.050 |
| | | | | 1.000 |

TABLE 48

19. ORTHOPEDICS

| Order Number | Medical Condition Number | SOI Level | Medical Condition Short Description | Market-basket Weight |
|---|---|---|---|---|
| 1 | 33.22 | 1 | Derangement of knee | 0.100 |
| 2 | 33.21 | 1 | Other joint derangement | 0.050 |
| 3 | 31.4 | 1 | Bursitis | 0.100 |
| 4 | 31.4 | 2 | Bursitis | 0.025 |
| 5 | 31.9 | 1 | Low back pain | 0.075 |
| 6 | 31.9 | 2 | Low back pain | 0.025 |
| 7 | 31.8 | 1 | Cervical spine pain | 0.050 |
| 8 | 33.15 | 1 | Degenerative joint disease | 0.075 |
| 9 | 32.11 | 1 | Fracture of hand bones | 0.050 |
| 10 | 32.13 | 1 | Fracture of radius and ulna | 0.050 |
| 11 | 32.14 | 1 | Fracture of humerus | 0.050 |
| 12 | 33.16 | 1 | Fracture of foot bones | 0.025 |
| 13 | 33.17 | 1 | Fracture of ankle | 0.025 |
| 14 | 33.19 | 1 | Fracture of tibia and fibula | 0.025 |
| 15 | 4.5 | 1 | Carpal tunnel syndrome | 0.050 |
| 16 | 33.9 | 1 | Dislocation of knee | 0.050 |
| 17 | 31.12 | 1 | Scoliosis | 0.025 |
| 18 | 32.2 | 1 | Sprain/strain of wrist & finger | 0.025 |
| 19 | 33.2 | 1 | Sprain/strain of foot and ankle | 0.025 |
| 20 | 33.3 | 1 | Sprain/strain of leg | 0.020 |
| 21 | 4.1 | 1 | Neuritis upper, lower limbs | 0.020 |
| 22 | 31.3 | 1 | Other arthropathy disorders | 0.020 |
| 23 | 32.1 | 1 | Contusion of upper limb | 0.020 |
| 24 | 33.1 | 1 | Contusion of lower limb | 0.020 |
| | | | | 1.000 |

TABLE 49

20. OTOLARYNGOLOGY (ENT)

| Order Number | Medical Condition Number | SOI Level | Medical Condition Short Description | Market-basket Weight |
|---|---|---|---|---|
| 1 | 6.5 | 1 | Otitis media | 0.150 |
| 2 | 7.2 | 1 | Sinusitis | 0.075 |
| 3 | 7.2 | 2 | Sinusitis | 0.050 |
| 4 | 7.1 | 1 | Rhinitis | 0.075 |
| 5 | 9.5 | 1 | Hypertrophy tonsils & aden | 0.075 |
| 6 | 7.4 | 1 | Deviated nasal septum | 0.075 |
| 7 | 6.10 | 1 | Hearing loss | 0.050 |
| 8 | 6.8 | 1 | Vertiginous syndromes | 0.050 |
| 9 | 9.2 | 1 | Dz upper respiratory tract | 0.050 |
| 10 | 9.1 | 1 | Upper respiratory infections | 0.050 |
| 11 | 7.5 | 1 | Nasal bone fracture | 0.025 |
| 12 | 6.1 | 1 | Otitis externa | 0.025 |
| 13 | 6.6 | 1 | Dsdr of tympanic membrane | 0.025 |
| 14 | 6.7 | 1 | Disorders of middle ear | 0.025 |
| 15 | 6.4 | 1 | Other disorders of ear | 0.025 |
| 16 | 4.3 | 1 | Headaches | 0.025 |
| 17 | 6.2 | 1 | Wax in ear | 0.025 |
| 18 | 2.10 | 1 | Infectious mononucleosis | 0.025 |
| 19 | 8.13 | 1 | Diseases of salivary glands | 0.025 |
| 20 | 8.15 | 1 | Benign neop of oral cavity | 0.025 |
| 21 | 8.14 | 1 | Diseases of oral soft tissue | 0.025 |
| 22 | 16.2 | 1 | Goiter | 0.025 |
| | | | | 1.000 |

TABLE 50

21. PEDIATRICS

| Order Number | Medical Condition Number | SOI Level | Medical Condition Short Description | Market-basket Weight |
|---|---|---|---|---|
| 1 | 6.5 | 1 | Otitis media | 0.175 |
| 2 | 9.1 | 1 | Upper respiratory infections | 0.125 |
| 3 | 7.2 | 1 | Sinusitis | 0.100 |
| 4 | 9.4 | 1 | Acute bronchitis | 0.075 |
| 5 | 9.11 | 1 | Asthma | 0.050 |
| 6 | 7.1 | 1 | Rhinitis | 0.050 |
| 7 | 9.7 | 1 | Pneumonia | 0.050 |
| 8 | 13.13 | 1 | Noninfect gastroent & colitis | 0.050 |
| 9 | 13.3 | 1 | Infect diarrhea/gastroenteritis | 0.025 |
| 10 | 29.9 | 1 | Dermatitis and eczema | 0.050 |
| 11 | 2.6 | 1 | Other viral diseases | 0.025 |
| 12 | 5.2 | 1 | Conjunctivitis | 0.025 |
| 13 | 22.3 | 1 | Urinary tract infections | 0.025 |
| 14 | 6.1 | 1 | Otitis externa | 0.025 |

TABLE 50-continued

21. PEDIATRICS

| Order Number | Medical Condition Number | SOI Level | Medical Condition Short Description | Market-basket Weight |
|---|---|---|---|---|
| 15 | 36.16 | 1 | Non-specific exanthem | 0.025 |
| 16 | 34.14 | 1 | Personality & disturb dsdr | 0.025 |
| 17 | 2.9 | 1 | Viral warts | 0.025 |
| 18 | 29.7 | 1 | Impetigo | 0.025 |
| 19 | 29.14 | 1 | Dermatophytoses | 0.025 |
| 20 | 36.17 | 1 | Abdominal pain | 0.025 |
|  |  |  |  | 1.000 |

TABLE 51

22. PLASTIC SURGERY

| Order Number | Medical Condition Number | SOI Level | Medical Condition Short Description | Market-basket Weight |
|---|---|---|---|---|
| 1 | 30.1 | 1 | Inflammatory disease of breast | 0.175 |
| 2 | 30.2 | 1 | Cystic breast disease | 0.075 |
| 3 | 29.19 | 1 | Benign neoplasm of skin | 0.125 |
| 4 | 8.5 | 1 | Open wound face & mouth | 0.100 |
| 5 | 32.5 | 1 | Open wound hand & fingers | 0.075 |
| 6 | 6.3 | 1 | Open wound of ear | 0.025 |
| 7 | 4.5 | 1 | Carpal tunnel syndrome | 0.050 |
| 8 | 29.6 | 1 | Skin keratoses | 0.050 |
| 9 | 29.26 | 1 | Other malignancy of skin | 0.050 |
| 10 | 21.2 | 1 | Hemangioma | 0.050 |
| 11 | 29.15 | 1 | Sebaceous cyst | 0.050 |
| 12 | 29.18 | 1 | Lipoma | 0.050 |
| 13 | 29.5 | 1 | Other dsdr skin/subcutan tiss | 0.050 |
| 14 | 7.4 | 1 | Deviated nasal septum | 0.025 |
| 15 | 29.28 | 1 | Malig melanoma of skin, initial | 0.025 |
| 16 | 30.10 | 1 | Malig neop of breast, fup | 0.025 |
|  |  |  |  | 1.000 |

TABLE 52

23. PODIATRY

| Order Number | Medical Condition Number | SOI Level | Medical Condition Short Description | Market-basket Weight |
|---|---|---|---|---|
| 1 | 33.14 | 1 | Hammer toe | 0.125 |
| 2 | 33.14 | 2 | Hammer toe | 0.050 |
| 3 | 29.20 | 1 | Dz of nail, excluding infections | 0.100 |
| 4 | 31.4 | 1 | Bursitis | 0.100 |
| 5 | 29.10 | 1 | Cellul & abscess, finger/toe | 0.075 |
| 6 | 2.9 | 1 | Viral warts | 0.075 |
| 7 | 31.3 | 1 | Other arthropathy disorders | 0.075 |
| 8 | 33.11 | 1 | Cong deformities lower limb | 0.075 |
| 9 | 31.9 | 1 | Low back pain | 0.050 |
| 10 | 33.22 | 1 | Derangement of knee | 0.050 |
| 11 | 29.14 | 1 | Dermatophytoses | 0.050 |
| 12 | 4.1 | 1 | Neuritis upper, lower limbs | 0.050 |
| 13 | 33.16 | 1 | Fracture of foot bones | 0.050 |
| 14 | 33.15 | 1 | Degenerative joint disease | 0.025 |
| 15 | 33.13 | 1 | Benign neop of lower limb | 0.025 |
| 16 | 29.25 | 1 | Chronic skin ulcer | 0.025 |
|  |  |  |  | 1.000 |

TABLE 53

24. PSYCHIATRY

| Order Number | Medical Condition Number | SOI Level | Medical Condition Short Description | Market-basket Weight |
|---|---|---|---|---|
| 1 | 34.21 | 1 | Major depression | 0.175 |
| 2 | 34.21 | 2 | Major depression | 0.050 |
| 3 | 34.14 | 1 | Personality & disturb dsdr | 0.150 |
| 4 | 34.14 | 2 | Personality & disturb dsdr | 0.050 |
| 5 | 34.17 | 1 | Nonpsychotic depression | 0.100 |
| 6 | 34.13 | 1 | Anxiety disorders | 0.075 |
| 7 | 34.6 | 1 | Other neurotic disorders | 0.075 |
| 8 | 34.24 | 1 | Bipolar depression | 0.050 |
| 9 | 34.20 | 1 | Sleep apnea | 0.025 |
| 10 | 34.5 | 1 | Insomnia | 0.025 |
| 11 | 34.18 | 1 | Obsessive-compulsive dsdr | 0.025 |
| 12 | 34.29 | 1 | Alcohol dependence | 0.025 |
| 13 | 34.30 | 1 | Drug dependence | 0.025 |
| 14 | 34.32 | 1 | Schizophrenia | 0.025 |
| 15 | 34.31 | 1 | Organic dementias | 0.025 |
| 16 | 34.12 | 1 | Phobic disorders | 0.025 |
| 17 | 34.23 | 1 | Manic depression | 0.025 |
| 18 | 34.15 | 1 | Other nonorganic psychoses | 0.025 |
| 19 | 34.25 | 1 | Bulimia | 0.025 |
|  |  |  |  | 1.000 |

TABLE 54

25. PSYCHOLOGY

| Order Number | Medical Condition Number | SOI Level | Medical Condition Short Description | Market-basket Weight |
|---|---|---|---|---|
| 1 | 34.14 | 1 | Personality & disturb dsdr | 0.175 |
| 2 | 34.14 | 2 | Personality & disturb dsdr | 0.075 |
| 3 | 34.21 | 1 | Major depression | 0.125 |
| 4 | 34.21 | 2 | Major depression | 0.050 |
| 5 | 34.17 | 1 | Nonpsychotic depression | 0.125 |
| 6 | 34.13 | 1 | Anxiety disorders | 0.075 |
| 7 | 34.6 | 1 | Other neurotic disorders | 0.075 |
| 8 | 34.18 | 1 | Obsessive-compulsive dsdr | 0.050 |
| 9 | 34.29 | 1 | Alcohol dependence | 0.050 |
| 10 | 34.30 | 1 | Drug dependence | 0.025 |
| 11 | 34.26 | 1 | Anorexia nervosa | 0.025 |
| 12 | 34.25 | 1 | Bulimia | 0.025 |
| 13 | 34.12 | 1 | Phobic disorders | 0.025 |
| 14 | 34.8 | 1 | Sexual deviations | 0.025 |
| 15 | 34.24 | 1 | Bipolar depression | 0.025 |
| 16 | 34.31 | 1 | Organic dementias | 0.025 |
| 17 | 34.15 | 1 | Other nonorganic psychoses | 0.025 |
|  |  |  |  | 1.000 |

TABLE 55

26. PULMONOLOGY

| Order Number | Medical Condition Number | SOI Level | Medical Condition Short Description | Market-basket Weight |
|---|---|---|---|---|
| 1 | 9.14 | 1 | COPD | 0.150 |
| 2 | 9.11 | 1 | Asthma | 0.150 |
| 3 | 34.20 | 1 | Sleep apnea | 0.075 |
| 4 | 9.10 | 1 | Chronic bronchitis | 0.075 |
| 5 | 9.4 | 1 | Acute bronchitis | 0.050 |
| 6 | 9.7 | 1 | Pneumonia | 0.050 |
| 7 | 9.3 | 1 | Lower respiratory diseases | 0.050 |
| 8 | 10.2 | 1 | Hypertension | 0.050 |
| 9 | 7.2 | 1 | Sinusitis | 0.050 |
| 10 | 7.1 | 1 | Rhinitis | 0.050 |
| 11 | 9.9 | 1 | Pleurisy | 0.050 |

TABLE 55-continued

26. PULMONOLOGY

| Order Number | Medical Condition Number | SOI Level | Medical Condition Short Description | Market-basket Weight |
|---|---|---|---|---|
| 12 | 19.7 | 1 | Cystic fibrosis | 0.050 |
| 13 | 9.1 | 1 | Upper respiratory infections | 0.050 |
| 14 | 36.18 | 1 | Dyspnea | 0.050 |
| 15 | 9.19 | 1 | Malig neop bron/lung, active | 0.025 |
| 16 | 9.20 | 1 | Malig neop bron/lung, inactive | 0.025 |
| | | | | 1.000 |

TABLE 56

27. RHEUMATOLOGY

| Order Number | Medical Condition Number | SOI Level | Medical Condition Short Description | Market-basket Weight |
|---|---|---|---|---|
| 1 | 31.19 | 1 | Rheumatoid arthritis | 0.175 |
| 2 | 31.18 | 1 | Diffuse connective tiss dsdr | 0.150 |
| 3 | 33.15 | 1 | Degenerative joint disease | 0.125 |
| 4 | 31.9 | 1 | Low back pain | 0.075 |
| 5 | 31.8 | 1 | Cervical spine pain | 0.050 |
| 6 | 31.3 | 1 | Other arthropathy disorders | 0.050 |
| 7 | 31.4 | 1 | Bursitis | 0.075 |
| 8 | 29.23 | 1 | Psoriasis and pityriasis | 0.050 |
| 9 | 19.5 | 1 | Gout | 0.050 |
| 10 | 4.5 | 1 | Carpal tunnel syndrome | 0.050 |
| 11 | 31.14 | 1 | Osteoporosis | 0.025 |
| 12 | 31.5 | 1 | Other dsdr bone & cartilage | 0.025 |
| 13 | 4.7 | 1 | Nerve root and plexus dsdr | 0.025 |
| 14 | 11.7 | 1 | Disorders of arteries | 0.025 |
| 15 | 19.4 | 1 | Disorders of lipid metabolism | 0.025 |
| 16 | 33.22 | 1 | Derangement of knee | 0.025 |
| | | | | 1.000 |

TABLE 57

28. SPORTS/PHYSICAL MEDICINE

| Order Number | Medical Condition Number | SOI Level | Medical Condition Short Description | Market-basket Weight |
|---|---|---|---|---|
| 1 | 31.4 | 1 | Bursitis | 0.175 |
| 2 | 31.4 | 2 | Bursitis | 0.025 |
| 3 | 31.9 | 1 | Low back pain | 0.100 |
| 4 | 31.8 | 1 | Cervical spine pain | 0.050 |
| 5 | 33.22 | 1 | Derangement of knee | 0.075 |
| 6 | 33.15 | 1 | Degenerative joint disease | 0.075 |
| 7 | 33.21 | 1 | Other joint derangement | 0.075 |
| 8 | 31.3 | 1 | Other arthropathy disorders | 0.050 |
| 9 | 32.3 | 1 | Sprain/strain of upper arm | 0.075 |
| 10 | 32.2 | 1 | Sprain/strain of wrist & finger | 0.050 |
| 11 | 33.2 | 1 | Sprain/strain of foot and ankle | 0.050 |
| 12 | 33.3 | 1 | Sprain/strain of leg | 0.050 |
| 13 | 33.4 | 1 | Sprain/strain of hip and thigh | 0.050 |
| 14 | 11.4 | 1 | Concussion | 0.050 |
| 15 | 32.13 | 1 | Fracture of radius and ulna | 0.025 |
| 16 | 4.5 | 1 | Carpal tunnel syndrome | 0.025 |
| | | | | 1.000 |

TABLE 58

29. UROLOGY

| Order Number | Medical Condition Number | SOI Level | Medical Condition Short Description | Market-basket Weight |
|---|---|---|---|---|
| 1 | 22.11 | 1 | Calculus of kidney and ureter | 0.150 |
| 2 | 24.6 | 1 | Prostatic hypertro & prostatitis | 0.125 |
| 3 | 23.3 | 1 | Uterovaginal prolapse | 0.075 |
| 4 | 22.10 | 1 | Disorders of kidney and ureter | 0.075 |
| 5 | 22.3 | 1 | Urinary tract infections | 0.075 |
| 6 | 24.4 | 1 | Disorders of penis | 0.075 |
| 7 | 24.9 | 1 | Malig neop of prostate, active | 0.075 |
| 8 | 24.10 | 1 | Malig neop of prostate, inactive | 0.025 |
| 9 | 22.5 | 1 | Urethral stricture | 0.050 |
| 10 | 24.3 | 1 | Dsdr of male genital organs | 0.050 |
| 11 | 25.4 | 1 | Infertility male | 0.050 |
| 12 | 22.4 | 1 | Urethritis | 0.025 |
| 13 | 24.2 | 1 | Orchitis and epididymitis | 0.025 |
| 14 | 12.4 | 1 | Varicose veins of other sites | 0.025 |
| 15 | 22.6 | 1 | Other disorders of bladder | 0.025 |
| 16 | 24.1 | 1 | Hyrocele | 0.025 |
| 17 | 14.3 | 1 | External abdominal hernias | 0.025 |
| 18 | 2.9 | 1 | Viral warts | 0.025 |
| | | | | 1.000 |

TABLE 59

30. VASCULAR SURGERY

| Order Number | Medical Condition Number | SOI Level | Medical Condition Short Description | Market-basket Weight |
|---|---|---|---|---|
| 1 | 14.3 | 1 | External abdominal hernias | 0.100 |
| 2 | 15.4 | 1 | Cholelithiasis | 0.100 |
| 3 | 30.2 | 1 | Cystic breast disease | 0.075 |
| 4 | 30.1 | 1 | Inflammatory disease of breast | 0.075 |
| 5 | 30.3 | 1 | Benign neoplasm of breast | 0.050 |
| 6 | 12.5 | 1 | Varicose veins lower extrem | 0.075 |
| 7 | 11.8 | 1 | Generalized arteriosclerosis | 0.050 |
| 8 | 11.8 | 2 | Generalized arteriosclerosis | 0.025 |
| 9 | 13.14 | 1 | Appendicitis | 0.050 |
| 10 | 12.3 | 1 | Other peripheral vascular dz | 0.050 |
| 11 | 11.12 | 1 | Occulsion of cerebral arteries | 0.050 |
| 12 | 11.7 | 1 | Disorders of arteries | 0.050 |
| 13 | 29.18 | 1 | Lipoma | 0.050 |
| 14 | 29.15 | 1 | Sebaceous cyst | 0.050 |
| 15 | 13.17 | 1 | Benign neop colon/rectum | 0.025 |
| 16 | 12.6 | 1 | Thrombophlebitis | 0.025 |
| 17 | 29.19 | 1 | Benign neoplasm of skin | 0.025 |
| 18 | 12.2 | 1 | Hemorrhoids | 0.025 |
| 19 | 17.1 | 1 | Diabetes w/no complications | 0.025 |
| 20 | 17.4 | 1 | Diabetes with circulatory | 0.025 |
| | | | | 1.000 |

TABLE 60

31. CRITICAL CARE (INTENSIVIST)

| Order Number | Medical Condition Number | SOI Level | Medical Condition Short Description | Market-basket Weight |
|---|---|---|---|---|
| 1 | 9.14 | 1 | COPD | 0.150 |
| 2 | 9.11 | 1 | Asthma | 0.150 |
| 3 | 34.20 | 1 | Sleep apnea | 0.075 |
| 4 | 9.10 | 1 | Chronic bronchitis | 0.075 |
| 5 | 9.4 | 1 | Acute bronchitis | 0.050 |
| 6 | 9.7 | 1 | Pneumonia | 0.050 |
| 7 | 9.3 | 1 | Lower respiratory diseases | 0.050 |
| 8 | 10.2 | 1 | Hypertension | 0.050 |
| 9 | 7.2 | 1 | Sinusitis | 0.050 |

TABLE 60-continued

31. CRITICAL CARE (INTENSIVIST)

| Order Number | Medical Condition Number | SOI Level | Medical Condition Short Description | Market-basket Weight |
|---|---|---|---|---|
| 10 | 7.1 | 1 | Rhinitis | 0.050 |
| 11 | 9.9 | 1 | Pleurisy | 0.050 |
| 12 | 19.7 | 1 | Cystic fibrosis | 0.050 |
| 13 | 9.1 | 1 | Upper respiratory infections | 0.050 |
| 14 | 36.18 | 1 | Dyspnea | 0.050 |
| 15 | 9.19 | 1 | Malig neop bron/lung, active | 0.025 |
| 16 | 9.20 | 1 | Malig neop bron/lung, inactive | 0.025 |
|   |   |   |   | 1.000 |

Step 14: Perform PROVSPEC Output Process

The PROVSPEC output process involves the completion of Fields 8-10 in Table 25, Fields in the PATAN Output File. Field 8 indicates the physician specialty. Field 9 indicates the physician marketbasket. Field 10 indicates the physician aggregate grouping code number.

Step 15: Store PROSPEC Output File

The PROSPEC Output File is stored with the same fields and in the same order as Table 25, Fields in the PATAN Output File. However, Fields 8-10 have now been completed.

Step 16: Sort PROVSPEC Output File: PROVSORT2

In an embodiment, the PROVSPEC Output File is sorted by three main sort keys. The primary sort key is report group. The secondary sort key is marketbasket identifier. The third sort key is physician identifier.

Step 17: Read in Episode Assignments to PROVAN from PROVSORT2

The episode assignments from PROVSORT2 are read into the physician analysis module (PROVAN). PROVAN produces the physician efficiency scores and several output files at the conclusion of processing.

Step 18: Perform High Outlier Analysis

There are two high-end outlier analysis rules. Both rules are performed at the marketbasket and physician specialty level. Both rules are performed after episodes have been assigned to individual physicians (or physician groups, if the analysis is at the physician group level instead of the individual physician level).

The first high-end outlier rule is as follows. A percent of a physician's most expensive episodes are eliminated by medical condition and severity-of-illness (SOI) level. The user select the percent to be eliminated from the choices available for the parameter SWITCH_HIGHOUTPERCENT in the RUN.INI file (refer to Table 6, Parameters in the RUN.INI File). Episodes are removed from each medical condition in the physician's marketbasket separately, starting with the most expensive episode and continuing in order of expense until the specified percent of episodes is reached.

If a physician has fewer than the number of condition-specific episodes required to satisfy the high outlier rule described above (for example, fewer than 20 episodes when the threshold is set at 5%), then the user may analyze the condition further, as described below under the SWITCH_HIGHOUTDIFF parameter.

In determining the number of condition-specific episodes available for this analysis, all episodes are excluded from the count if they fall below the low outlier threshold set by the parameter SWITCH_LOWOUTDOLLAR, which is described in the low outliers step.

The second high-end outlier rule is as follows. The parameter SWITCH_HIGHOUTDIFF in the RUN.INI file is used to determine whether a single episode should be removed as a high-outlier (refer to Table 6, Parameters in the RUN.INI File). This high-end outlier parameter is applied when one high-end outlier cannot be removed under the SWITCH_HIGHOUTPERCENT parameter. The user sets the value of this parameter to a whole number representing a percentage. If the charges for the most expensive episode are at least the defined percentage greater than the charges for the next most expensive episode, the most expensive episode is removed as a high outlier.

For example, consider a physician whose highest upper respiratory infection episode charge is $500 and whose second highest upper respiratory infection charge is $165 and SWITCH_HIGHOUTDIFF set at 200%. To be eliminated, the physician's most expensive episode must be 200% of the next most expensive episode. Since $500 is more than 200% of $165, the high charge episode will be removed as a high outlier. If the high-charge episode had been $300, it would not be removed, since $300 is only 82% greater than $165.

A maximum of one episode for each medical condition in the physician's marketbasket may be removed by this analysis. Although the user can set SWITCH_HIGHOUTDIFF to any amount, for most effective analysis, the recommended setting is between 150% and 250%.

Step 19: Perform Low Outlier Analysis

There are two low-end outlier analysis rules. Both rules are performed at the marketbasket and physician specialty level. Both rules are performed before episodes have been assigned to individual physicians (or physician groups, if the analysis is at the physician group level instead of the individual physician level).

The first low-end outlier analysis is performed with respect to all episodes by medical condition and severity-of-illness (SOI) level that are assigned to a report group. For this analysis, all physicians are examined within the same medical specialty and within the same Aggregate Report Group.

A percent of the least expensive episodes is eliminated by medical condition and SOI level. The user selects the percent to be eliminated from the choices available for the parameter SWITCH_LOWOUTPERCENT in the RUN.INI file (refer to Table 6, Parameters in the RUN.INI File). Episodes are removed from each medical condition separately, starting with the least expensive episode and continuing until the specified percent of episodes is reached. For example, assume there are 500 episodes of upper respiratory infection (URI), SOI-1 level, assigned to a peer group of general internists, and the user selects 5% low-end outliers. Then, the 25 lowest charge episodes (500×0.25) are removed from analysis.

The second low-end outlier rule is as follows. Any remaining condition-specific episodes are eliminated with less than a defined threshold of charges. The user sets the threshold, which can be any whole number representing dollars in the RUN.INI file using the parameter SWITCH_LOWOUTDOLLAR (refer to Table 6, Parameters in the RUN.INI File). In the above example, assume after applying the 5% low-end outlier analysis, the user found that episodes of URI, SOI-1 level remained that are less than $20. By setting the parameter SWITCH_LOWOUTDOLLAR to $20, any remaining URI, SOI-1 level episodes less than $20 would be removed from analysis.

Step 20: Calculate Physician Condition-Specific Episode Statistics

For condition-specific, SOI-level episodes assigned to a physician, the episode means (averages) and standard deviations are calculated for utilization and charges in the following service and sub-service categories: (1) overall condition-specific, SOI-level episode duration (in days; refer to Table 61); (2) overall condition-specific, SOI-level episode charges (refer to Table 62); (3) service category condition-specific, SOI-level episode utilization (refer to Table 61); (4) service category condition-specific, SOI-level episode charges (refer to Table 62); (5) sub-service category condition-specific, SOI-level episode utilization (refer to Table 63); and (6) sub-service category condition-specific, SOI-level episode charges (refer to Table 64).

In an embodiment, there are 11 service category utilization fields (Fields 1-11 in Tables 61 and 62) that are set up within the service category utilization section of the PATAN and PROVSPEC output displays. The system of the present invention does not break out charges for inpatient facility admissions so Field 9 is not used and contains a zero as a placeholder (refer to Table 62).

In an embodiment, there are 21 category utilization fields (Fields 1-21 in Tables 63 and 64) that are set up within the service category utilization section of the PATAN and PROVSPEC output displays. The system of the present invention does not break out charges for inpatient facility admissions so Field 14 is not used and contains a zero as a placeholder (refer to Table 64).

The zero field in the service and sub-service categories for utilization data (Tables 61 and 63) corresponds to the average episode duration. The zero field in the service and sub-service categories for charges (Tables 62 and 64) corresponds to the average charges per episode.

It is to be understood that other statistics can be calculated for condition-specific, SOI-level episodes assigned to a physician. In an embodiment, different service and sub-service categories may be calculated for episode utilization and charges. In an embodiment, episodes can be assigned to physician groups (and not only individual physicians), and the physician group's episode means and standard deviations may be calculated for utilization and charges.

TABLE 61

Service Category Fields Used for Utilization Data

| Utilization Field | Service Category |
| --- | --- |
| 0 | Episode Duration (Days) |
| 1 | Professional Visits |
| 2 | Laboratory/Pathology |
| 3 | Diagnostic Tests |
| 4 | Medical/Surgical |
| 5 | Prescription Drugs |
| 6 | Inpatient Professional |
| 7 | Outpatient Facility |
| 8 | Inpatient Facility Days |
| 9 | Inpatient Facility Admits |
| 10 | Alternate Facility |
| 11 | Other Medical Care |

TABLE 62

Service Category Fields Used for Charge Data

| Charge Field | Service Category |
| --- | --- |
| 0 | Overall Charges |
| 1 | Professional Visits |
| 2 | Lab/Path |
| 3 | Diagnostic Tests |
| 4 | Medical/Surgical |
| 5 | Prescriptions Drugs |
| 6 | Inpatient Professional |
| 7 | Outpatient Facility |
| 8 | Inpatient Facility Days |
| 9 | [Not used] |
| 10 | Alternate Facility |
| 11 | Other Medical Care |

TABLE 63

Sub-Service Category Fields Used for Utilization Data

| Utilization Field | Sub-service category |
| --- | --- |
| 0 | Episode Duration (Days) |
| 1 | Professional Visits |
| 2 | Lab |
| 3 | Pathology |
| 4 | Imaging |
| 5 | Invasive Testing |
| 6 | Functional Testing |
| 7 | Medical Procedures |
| 8 | Surgical Procedures |
| 9 | Prescription Drugs |
| 10 | Inpatient Professional |
| 11 | Emergency Room Facility |
| 12 | Other Outpatient Facility |
| 13 | Inpatient Facility Days |
| 14 | Inpatient Facility Admits |
| 15 | Alternate Facility |
| 16 | Physical Therapy |
| 17 | Dialysis |
| 18 | Chemotherapy/Radiology |
| 19 | Anesthesia |
| 20 | Durable Medical Equipment |
| 21 | Other Medical Care |

TABLE 64

Sub-Service Category Fields Used for Charge Data

| Charge Field | Sub-service category |
| --- | --- |
| 0 | Overall charges |
| 1 | Professional Visits |
| 2 | Lab |
| 3 | Pathology |
| 4 | Imaging |
| 5 | Invasive Testing |
| 6 | Functional Testing |
| 7 | Medical Procedures |
| 8 | Surgical Procedures |
| 9 | Prescription Drugs |
| 10 | Inpatient Professional |
| 11 | Emergency Room Facility |
| 12 | Other Outpatient Facility |
| 13 | Inpatient Facility Days |
| 14 | [Not used] |
| 15 | Alternate Facility |
| 16 | Physical Therapy |
| 17 | Dialysis |
| 18 | Chemotherapy/Radiology |
| 19 | Anesthesia |
| 20 | Durable Medical Equipment |
| 21 | Other Medical Care |

Step 21: Determine Minimum Episode Number

A physician should have a minimum number of non-outlier episodes for medical conditions within a marketbasket of medical conditions. The system of the present invention recognizes that a physician should have a minimum number of non-outlier episodes in each of three specialty-specific medical conditions to receive an efficiency measurement score. This episode is called the N×3 rule because it requires N episodes in each of three medical conditions.

The user specifies the number of episodes (N) using the parameter SWITCH_MINEPCOUNT in the RUN.INI file (refer to Table 6, Parameters in the RUN.INI File). This parameter sets the requirement for the number of episodes a physician should treat to be included in the analysis, thus implementing part of the N×3 rule. For example, if the N value is changed from two to four, the rule would require four non-outlier episodes in each of three conditions, and the rule would become, in effect, a "4×3" rule.

In the N×3 rule, the N equals the number of episodes of a specific medical condition a physician should treat during the study period. The user can change this number. The three equals the minimum number of medical conditions in which the physician should treat episodes. The medical conditions need to be in the physician's marketbasket.

For example, if N in the N×3 rule is set to two, then a physician needs to have two non-outlier episodes in three medical conditions (2×3) in a respective specialty-specific marketbasket. Therefore, regardless of specialty type, each physician needs to have a minimum six non-outlier episodes of care to receive an efficiency score.

Continuing our example, with N set to two episodes, and assuming a physician meets the minimum episode number criteria in three medical conditions (e.g., 2×3), then the following method is employed before formulating a weighted average treatment pattern. For a physician with less than two episodes for any medical condition in a marketbasket, the physician-specific results are replaced with that of the peer group results for the medical condition of interest. For the scenario just defined, the peer group's condition-specific results will be used when formulating the physician's weighted average treatment pattern results for at least one medical condition in the marketbasket.

Therefore, an additional rule applies when a physician has fewer than the required number of condition-specific episodes (as set by the value of N). Substitute the specialty-specific, peer group results for a medical condition when a physician has less than the required number of condition-specific episodes.

It is to be understood that other, similar methods and rules may be employed to ensure a physician has a minimum number of assigned, non-outlier episodes for medical conditions.

Step 22: Remove Physicians Failing Minimum Episode Number

This rule involves removing those physicians from further analysis that do not meet the minimum number of assigned episodes rule. For example, using the N×3 rule and assuming N is set to 2 episodes, then physicians without a minimum of 6 non-outlier episodes meeting the 2×3 rule are removed from further analysis.

Step 23: Calculate Peer Group Condition-Specific Episode Statistics

Using only those episodes of care assigned to physicians meeting the minimum non-outlier episode rule (i.e., physicians that passed the minimum episode rule and, therefore, are included in further analysis), the peer group medical condition, SOI-level episode means (averages) and standard deviations are calculated for utilization and charges. Each episode of care is counted once and only once in formulating the peer group condition-specific, SOI-level means and standard deviations.

Similar to the physician-level episode statistics, the peer group condition-specific, SOI-level statistics are calculated for utilization and charges using the same service and sub-service categories as defined in Tables 61-64.

For condition-specific, SOI-level episodes assigned to the peer group, the episode means (averages) and standard deviations are calculated for utilization and charges in the following service and sub-service categories: (1) overall condition-specific, SOI-level episode duration (in days; refer to Table 61); (2) overall condition-specific, SOI-level episode charges (refer to Table 62); (3) service category condition-specific, SOI-level episode utilization (refer to Table 61); (4) service category condition-specific, SOI-level episode charges (refer to Table 62); (5) sub-service category condition-specific, SOI-level episode utilization (refer to Table 63); and (6) sub-service category condition-specific, SOI-level episode charges (refer to Table 64). It is to be understood that other statistics can be calculated for the peer group condition-specific, SOI-level episodes, and that different service and sub-service categories may be calculated for episode utilization and charges.

Step 24: Calculate Peer Group Weighted Episode Statistics Across Medical Conditions Each medical condition in a specialty-specific marketbasket is assigned a weight factor that reflects the importance or relevance of that medical condition to the marketbasket. The weight factors are used to compute the overall marketbasket weighted mean and standard deviation across all medical conditions in the marketbasket. The sum of the weight factors in a marketbasket equals 1.00 (refer to the specialty-specific marketbaskets, Tables 29-60). This step is referred to as the indirect standardization rule.

The system of the present invention uses an indirect standardization technique for weighting together the episodes within the core group of medical conditions. The weighted mean and standard deviation are computed as the sum of the condition-specific utilization or charge amounts per episode multiplied by the weight value assigned to that condition in the marketbasket. Both the condition-specific means and variances (i.e., the square of the standard deviation) are multiplied by the weight values. The sum of all the condition-specific products is the weighted mean and standard deviation for the peer group in the marketbasket.

An example of the indirect standardization rule is presented for general internists. The general internist marketbasket consists of episodes in 30 medical conditions, SOI-1 class only (refer to Table 30, general internist marketbasket). Upper respiratory infections (URIs), sinusitis, acute bronchitis, and low back pain are medical conditions within the general internist marketbasket.

For simplicity, assume only four medical conditions comprise the general internist marketbasket: upper respiratory infections (URIs), sinusitis, acute bronchitis, and low back pain. A total of four medical conditions in the marketbasket classes will receive a weight factor. Assume the standardized weights are distributed as follows: URI=0.30; sinusitis=0.30; and acute bronchitis=0.20; and back pain=0.20. These weight factors sum to 1.00. The peer group treats a total of 4,500 non-outlier episodes: 1,350 episodes of URI; 1,350 episodes of sinusitis; 900 episodes of acute bronchitis; and 900 episodes of low back pain.

The weighted average is now formulated for the peer group's overall episode charges. The peer group's condition-specific means and standard deviations (SD) are as follows: URI=$150 per episode (SD=$50); sinusitis=$200 per episode (SD=$70); acute bronchitis=$175 per episode (SD=$55); and back pain=$300 per episode (SD=$90).

Using these assumptions, the marketbasket weighted mean and standard deviation (SD) are calculated for the general internist peer group. The weighted overall charge mean is $200 ((0.30×$150)+(0.30×$200)+(0.20×$175)+(0.20×$300)). The calculation does not use the peer group's actual episode composition to calculate the weighted average. Instead, the predetermined standard marketbasket weights are used.

The variances are weighted together, which is the SD squared. After adding the variances together, the square root is performed to formulate the weighted average SD, which is $67 ((0.30×$2,500)+(0.30×$4,900)+(0.20×$3,025)+(0.20×$8,100)=$4,445; and the square root of $4,445=$67).

Therefore, the general internist peer group's weighted overall charge mean and SD are as follows: mean=$200 per episode; SD=$67 per episode; number of episodes N=4,500.

In a similar manner, the weighted statistics are calculated for the peer group's episode duration (in days), service category utilization and charges (refer to Tables 61 and 62), and sub-service category utilization and charges (refer to Tables 63 and 64).

Step 25: Calculate Physician Weighted Episode Statistics Across Medical Conditions For the individual physician (or alternatively, physician group), the same indirect standardization weighting calculations are performed using the physician's condition-specific utilization and charges per episode and the same specialty-specific marketbasket weights. The sum of all the condition-specific products is the weighted mean and standard deviation result for the physician.

Assume there continue to be only four medical conditions that comprise the general internist marketbasket: upper respiratory infections (URIs), sinusitis, acute bronchitis, and low back pain. A total of four medical conditions in the marketbasket classes will receive a weight factor. Also, assume the same standardized weights as for the peer group: URI=0.30; sinusitis=0.30; and acute bronchitis=0.20; and back pain=0.20. These weight factors sum to 1.00.

Without detailing the calculations here, assume the physician's weighted overall charge mean and SD are $254 per episode and $56 per episode, respectively. The number of physician episodes (N) is 53.

In a similar manner, the weighted statistics are calculated for the physician's episode duration, service category utilization and charges, and sub-service category utilization and charges.

Step 26: Determine Physician's Efficiency Scores

The physician's marketbasket weighted statistics are now compared to that of the specialty-specific peer group. This comparison is more meaningful (than just comparing treatment patterns for one medical condition) because the weighted statistics present a more realistic efficiency evaluation of the physician's overall work effort.

The overall efficiency score for the physician (or physician group) is calculated by dividing the physician's weighted overall mean charges by the peer group's weighted overall mean charges. Using the general internist example, the overall efficiency score equals 1.27 (or $254 per episode/$200 per episode. The 1.27 ratio may be interpreted as follows. The efficiency of the physician's weighted average treatment pattern is 27% more resource intensive than the peer group's weighted average treatment pattern. The general internist in the example had $54 per episode in excess charges ($254 per episode versus the peer group of $200 per episode).

If the efficiency score is more than 1.00, then the physician's treatment pattern efficiency is more resource intensive than the peer group's treatment pattern. On the other hand, if the efficiency score is less than 1.00, then the physician's treatment pattern efficiency is less resource intensive than the peer group's treatment pattern.

An efficiency score may be calculated for each medical condition in a specialty-specific marketbasket. The medical condition efficiency score for the physician is calculated by dividing the physician's condition-specific mean charges by the peer group's condition-specific mean charges.

An efficiency score may be calculated for each service category in an episode of care. The overall service efficiency score for the physician is calculated by dividing the physician's weighted service category mean utilization or charges by the peer group's weighted service category mean utilization or charges, respectively.

The medical condition service efficiency score for a physician is calculated by dividing the physician's condition-specific service mean utilization or charges by the peer group's condition-specific mean utilization or charges, respectively.

In addition, an efficiency score may be calculated for each sub-service category in an episode of care. The overall sub-service efficiency score for the physician is calculated by dividing the physician's weighted sub-service category mean utilization or charges by the peer group's weighted sub-service category mean utilization or charges, respectively. The medical condition sub-service efficiency score for a physician is calculated by dividing the physician's condition-specific sub-service category mean utilization or charges by the peer group's condition-specific sub-service mean utilization or charges, respectively.

An efficiency score may be calculated for the duration of an episode of care. The overall duration efficiency score for the physician is calculated by dividing the physician's weighted overall mean duration by the peer group's weighted overall mean duration. A condition-specific duration efficiency score may be calculated by dividing the physician's condition-specific mean duration by the peer group's condition-specific mean duration.

Step 27: Perform Test to Determine Whether Physician's Efficiency Scores are Statistically Different from Peer Group The student t-test is used to determine whether the physician's (or physician group's) efficiency score is statistically significantly different from the peer group. In the calculation, the physician's actual number of episodes is used as well as the peer group's actual number of episodes. For the general internist example, the physician's number of episodes is N equals 53, and the peer group's number of episodes is N equals 4,500.

At a determined level of confidence, the physician's marketbasket treatment pattern is determined to be statistically significantly different from the peer group average. The user chooses the desired level of confidence (either 0.10 level or 0.25 level) using the parameter SWITCH_CONFLEVEL in the RUN.INI file, which sets the p-value for statistical confidence (refer to Table 6, Parameters in the RUN.INI File). However, different p-values may be selected other than the 0.10 and 0.25 levels.

Step 28: Assign Physicians to an Interval

After receiving an efficiency score, physicians of a specific specialty type are separated into quartiles (1, 2, 3, and 4). Quartile 1 physicians use fewer medical resources to treat a marketbasket of condition-specific episodes as compared to their physician peer group. Quartile 2 and Quartile 3 physicians are the next quartiles of physicians in terms of the amount of resources used to treat the same marketbasket of condition-specific episodes. Quartile 4 physicians use greater medical resources to treat the same marketbasket of condition-specific episodes as compared to the physician peer group.

Physicians of a specific specialty type also are separated into deciles (1, 2, 3, 4, 5, 6, 7, 8, 9, and 10). Decile 1 physicians use fewer medical resources to treat a marketbasket of condition-specific episodes as compared to their physician peer group. Decile 2 through 9 physicians are the next deciles of physicians in terms of the amount of resources used to treat the same marketbasket of condition-specific episodes. Decile 10 physicians use the greatest amount of medical resources to treat the same marketbasket of condition-specific episodes as compared to the physician peer group.

The quartile and decile assignments are fields displayed on the PROVAN Output File. The embodiment recognizes that other physician interval assignments may be used other than quartile and decile.

Step 29: Store PROVAN Output Files

The system of the present invention stores two output files at the conclusion of processing. One file is entitled the Weighted Average Results File (default file name in RUN.INI File is Score.tab). The other file is entitled the Medical Condition Results File (default file name in RUN.INI File is Detail.tab).

These files are output from the PROVAN module. Table 65 provides an overview of the two output files. The table shows that the Weighted Average Results File produces physician-level (or physician group-level) results for the 11 service categories and 21 sub-service categories. However, the Medical Condition Results File produces physician-level (or physician group-level) results only for the 11 service categories. The embodiment recognizes that both PROVAN Output Files may produce results for the 21 sub-service categories as well as other formulated service and sub-service categories.

TABLE 65

PROVAN Output Files

| Descriptive File Name | Default File Name in RUN.INI | Description of Content | 11 Service Category Level Output | 21 Sub-service Category Output |
|---|---|---|---|---|
| Weighted Average Results File | Score.tab | Physician-level weighted average marketbasket results on utilization and charges per episode of care within a marketbasket of interest | YES | YES |
| Medical Condition Results File | Detail.tab | Physician-level medical condition level results on utilization and charges per episode of care within a marketbasket of interest | YES | NO |

The Weighted Average Results File presents the weighted average specialty-specific marketbasket results for a physician versus the comparator peer group. The file contains one output row per physician. Fields in each row show a weighted average result for each of the 11 service categories and each of the 21 sub-service categories. Fields are delimited by tab characters and, therefore, field width is variable.

The fields in the Weighted Average Results File are divided into sections as presented in Table 66.

TABLE 66

Sections in the Weighted Average Results File

| Section | Title |
|---|---|
| A | Non-Repeated Physician Fields |
| B | Repeated Physician Fields for Each Service Category |
| C | Non-Repeated Peer Group Fields |
| D | Repeated Peer Group Fields for Each Service Category |
| E | Repeated Physician Fields for Each Sub-Service Category |
| F | Repeated Peer Group Fields for Each Sub-Service Category |

Section A contains non-repeated physician fields (16 fields). The fields described in Section A contain physician data. Each field appears once in the Weighted Average Results File (refer to Table 67).

Section B contains repeated physician fields for each service category (6 fields repeated 11 times). Section B lists six fields that contain physician output data at the service category level. For convenience, the six fields, taken together, are called a group. In the Weighted Average Results File, the group of six fields listed in Section B repeats 11 times, once for each of the service categories, in the order listed in Tables 61 and 62.

Section C contains non-repeated peer group fields (2 fields). The fields described in Section C contain peer group data. Each field appears once in the Weighted Average Results File, in the order they are listed in Table 67.

Section D contains repeated peer group fields for each service category (2 fields repeated 11 times). Section D lists two fields that contain peer group output data at the service category level. The two fields, taken together, are a group. In the Weighted Average Results File (Table 67), the group of two fields listed in Section D repeats 11 times, once for each of the service categories in the order listed in Tables 61 and 62.

Section E contains repeated physician fields for each sub-service category (4 fields repeated 21 times). Section E lists four fields that contain physician output data at the sub-service category level. The four fields, taken together, are a group. In the Weighted Average Results File, the group of four fields listed in Section E repeats 21 times, once for each of the sub-service categories in the order listed in Tables 63 and 64.

Section F contains repeated peer group fields for each sub-service category (2 fields repeated 21 times). Section F lists two fields that contain peer group output data at the sub-service category level. The two fields, taken together, are a group. In the Weighted Average Results file, the group of two fields listed in Section F repeats 21 times, once for each of the sub-service categories in the order listed in Tables 63 and 64.

Table 67 presents the fields included in the Weighted Average Results File, listed in the order in which they appear. In the repeated field sections, the asterisk (*) indicates a sequential number of the service category or sub-service category number as presented in Tables 61-64.

TABLE 67

Fields in the Weighted Average Results File

| Field Number | Field Descriptive Name | Notes |
|---|---|---|
| Section A - Non-Repeated Physician Fields (16 fields) | | |
| 1 | Physician ID<br>Field name: ProvID | The unique physician ID for each profiled physician, as defined in the input files. |
| 2 | Physician Specialty Number<br>Field name: ProvSpec | The specialty number, as defined in the data mapping section. |
| 3 | Physician marketbasket number<br>Field name: MktBasket | The marketbasket number, as defined in the data mapping section. |
| 4 | Aggregate group number<br>Field name: AggGroup | The aggregate group number, as defined in the grouping structure table. |
| 5 | Pass N x N rule<br>Field name: PassN x N | 1 = The physician passed the N x 3 rule<br>0 = The physician failed the N x 3 rule |
| 6 | Quartile number<br>Field name: Quartile | The quartile number of the physician based on overall charge efficiency.<br>1 = lowest relative resource intensity<br>4 = highest relative resource intensity |
| 7 | Decile number<br>Field name: Decile | The decile number of the physician based on overall charge efficiency.<br>1 = lowest relative resource intensity<br>10 = highest relative resource intensity |
| 8 | Episode volume category<br>Field name: epcountbin | Indicates relative volume of total episodes for the physician. 1 = 25 or fewer episodes, 2 = 26 to 50 episodes, 3 = greater than 50 episodes. |
| 9 | Physician episode count<br>Field name: provider_episode_count | The total number of episodes for the physician, after outliers are removed. |
| 10 | Peer group episode count<br>Field name: peergroup_episode_count | The total number of episodes forming the peer group, after outliers are removed. |
| 11 | Physician weighted average episode duration<br>Field name: Prov_MBCCatUtl0 | Weighted average episode duration in days. |
| 12 | Physician relative efficiency score based on episode duration<br>Field name: Prov_ScoreCatUtl0 | Score as compared to peer group based on relative weighted average episode duration in days. |
| 13 | Physician episode duration t-test statistical significance indicator<br>Field name: Prov_TScoreCatUtl_sigdiff0 | 1 = result of physician t-test for average weighted episode duration is statistically significant at the selected confidence level.<br>0 = not statistically significant at selected confidence level. |
| 14 | Physician overall weighted average episode charges<br>Field name: Prov_MBCCatChg0 | Overall weighted average episode charges in dollars, across all service categories. |
| 15 | Physician overall relative efficiency score based on episode charges<br>Field name: Prov_ScoreCatChg0 | Score as compared to peer group based on overall relative weighted average episode charges in dollars. |
| 16 | Physician episode charges t-test statistical significance indicator<br>Field name: Prov_TScoreCatChg_sigdiff0 | 1 = result of physician t-test for average weighted episode charges is statistically significant at the selected confidence level.<br>0 = not statistically significant at selected confidence level. |
| Section B - Repeated Physician Fields for Each Service Category (6 fields repeated 11 times) | | |
| 1 | Physician weighted average per episode utilization for the service category<br>Field name: Prov_MBCCatUtl* | Weighted average per episode utilization for the service category (service category 8 contains inpatient days per episode, service category 9 contains inpatient admits per episode) |
| 2 | Physician relative efficiency score based on per episode utilization for the service category | Score as compared to peer group based on relative weighted average per episode utilization for the service category |

TABLE 67-continued

Fields in the Weighted Average Results File

| Field Number | Field Descriptive Name | Notes |
|---|---|---|
|   | Field name: Prov__ScoreCatUtl* | |
| 3 | Physician per-episode utilization t-test statistical significance indicator  Field name: Prov__TScoreCatUtl__sigdiff* | 1 = result of physician t-test for average weighted utilization for the service category is statistically significant at the selected confidence level.  0 = not statistically significant at selected confidence level. |
| 4 | Physician weighted average episode charges for the service category  Field name: Prov__MBCCatChg* | Weighted average episode charges in dollars, for the service category |
| 5 | Physician relative efficiency score based on episode charges for the service category  Field name: Prov__ScoreCatChg* | Score as compared to peer group based on relative weighted average episode charges in dollars, for the service category |
| 6 | Physician episode charges t-test statistical significance indicator for the service category  Field name: Prov__TScoreCatChg__sigdiff* | 1 = result of physician t-test for average weighted episode charges for the service category is statistically significant at the selected confidence level.  0 = not statistically significant at selected confidence level. |
| Section C - Non-Repeated Peer Group Fields (2 fields) | | |
| 1 | Peer Group overall weighted average episode duration  Field name: Peer__MBCCatUtl0 | Peer Group overall weighted average episode duration in days |
| 2 | Peer Group overall weighted average episode charges in dollars  Field name: Peer__MBCCatChg0 | Peer Group overall weighted average episode charges in dollars, across all service categories |
| (Section D) Repeated Peer Group Fields for Each Service Category (2 fields repeated 11 times) | | |
| 1 | Peer Group weighted average episode utilization for the service category  Field name: Peer__MBCCatUtl* | Peer Group weighted average episode utilization for the service category |
| 2 | Peer Group weighted average episode charges in dollars for the service category  Field name: Peer__MBCCatChg* | Peer Group weighted average episode charges in dollars for the service category |
| Section E - Repeated Physician Fields for Each Sub-Service Category (4 fields repeated 21 times) | | |
| 1 | Physician weighted average per episode utilization for the sub-service category  Field name: Prov__MBCSubUtl* | Weighted average per episode utilization for the sub-service category (sub-service category 13 contains inpatient days per episode, sub-service category 14 contains inpatient admits per episode) |
| 2 | Physician per-episode utilization t-test statistical significance indicator  Field name: Prov__TScoreSubUtl__sigdiff* | 1 = result of physician t-test for average weighted utilization for the sub-service category is statistically significant at the selected confidence level.  0 = not statistically significant at selected confidence level. |
| 3 | Physician weighted average episode charges for the sub-service category  Field name: Prov__MBCSubChg* | Weighted average episode charges in dollars, for the sub-service category |
| 4 | Physician episode charges t-test statistical significance indicator for the sub-service category  Field name: Prov__TScoreSubChg__sigdiff* | 1 = result of physician t-test for average weighted episode charges for the sub-service category is statistically significant at the selected confidence level.  0 = not statistically significant at selected confidence level. |
| Section F - Repeated Peer Group Fields for Each Sub-Service Category (2 fields repeated 21 times) | | |
| 1 | Peer Group weighted average episode utilization for the sub-category  Field name: Peer__MBCSubUtl* | Peer Group weighted average episode utilization for the sub-service category |
| 2 | Peer Group weighted average episode charges in dollars for the sub-service category  Field name: Peer__MBCSubChg* | Peer Group weighted average episode charges in dollars for the sub-service category |

The Medical Condition Results File presents the specialty-specific medical condition results for a physician versus the comparator peer group. Table 65 shows that medical condition average utilization and charge results are available for each of the 11 service categories tracked in the system of the present invention (e.g., lab/path services).

The Medical Condition Results File contains rows of data on medical conditions for each physician. There are up to 36 rows per physician (up to 35 medical conditions, plus the weighted average row). These rows of data are identified by the Marketbasket Condition Number field (Field 11 in Table 68).

The overall weighted average information has been carried over for each physician from the Weighted Average Results File and reported in the Medical Conditions Results file as well. For each physician, the weighted average output row is identified in the Marketbasket Condition Number field with the number "0". The rows of medical condition information for each physician begin with row "1" and continue until there is a row for the weighted average of each medical condition in the physician's specialty marketbasket.

Table 68 presents the fields included in the Medical Condition Results File, listed in the order in which they appear. In the repeated field sections, the asterisk (*) indicates a sequential number of the service category number as presented in Tables 61 and 62.

TABLE 68

Fields in the Medical Condition Results File

| Field Number | Field Descriptive Name | Notes |
|---|---|---|
| | Section A - Fundamental Information (19 fields) | |
| 1 | Physician ID<br>Field name: ProvID | The unique physician ID for each profiled physician, as defined in the input files. |
| 2 | Physician Specialty Number<br>Field name: ProvSpec | The specialty number, as defined in the data mapping section. |
| 3 | Physician marketbasket number<br>Field name: MktBasket | The marketbasket number, as defined in the data mapping section. |
| 4 | Aggregate group number<br>Field name: AggGroup | The aggregate group number, as defined in the grouping structure table. |
| 5 | Pass N × N rule<br>Field name: PassN × N | 1 = The physician passed the N × 3 rule<br>0 = The physician failed the N × 3 rule |
| 6 | Quartile number<br>Field name: Quartile | The quartile number of the physician based on overall charge efficiency.<br>1 = lowest relative resource intensity<br>4 = highest relative resource intensity |
| 7 | Decile number<br>Field name: Decile | The decile number of the physician based on overall charge efficiency.<br>1 = lowest relative resource intensity<br>10 = highest relative resource intensity |
| 8 | Episode volume category<br>Field name: epcountbin | Indicates relative volume of total episodes for the physician.<br>1 = 25 or fewer episodes<br>2 = 26 to 50 episodes<br>3 = greater than 50 episodes |
| 9 | Physician episode count<br>Field name: provider_episode_count | The total number of episodes for the physician, after outliers are removed. |
| 10 | Peer group episode count<br>Field name: peergroup_episode_count | The total number of episodes forming the peer group, after outliers are removed. |
| 11 | Marketbasket condition number<br>Field name: MBCondition | The sequential number of the condition within the marketbasket, as defined in the market conditions table which is specified by the RUN.INI parameter FILE_MBCONDITIONS. |
| 12 | Physician average episode duration<br>Field name: Prov_MBCatUtl0 | Average episode duration in days. For the "0" row, this field contains the weighted average episode duration in days. For all other rows, this field contains the average medical condition duration in days. |
| 13 | Physician relative efficiency score based on episode duration<br>Field name: Prov_ScoreCatUtl0 | Score as compared to peer group based on relative average episode duration in days. |
| 14 | Physician t-score for average episode duration<br>Field name: Prov_TScoreCatUtl0 | t-test score result as compared to peer group on relative average episode duration in days. |
| 15 | Physician episode duration t-test statistical significance indicator<br>Field name: Prov_TScoreCatUtl_sigdiff0 | 1 = result of physician t-test for average episode duration is statistically significant at the selected confidence level.<br>0 = not statistically significant at selected confidence level. |
| 16 | Physician average episode charges<br>Field name: Prov_MBCatChg0 | Average episode charges in dollars, across all service categories. For the "0" row, this field contains the weighted overall average episode charges. For all other rows, this field contains the overall average medical condition charges per episode. |
| 17 | Physician relative efficiency score based on episode charges<br>Field name: Prov_ScoreCatChg0 | Score as compared to peer group based on relative average episode charges in dollars. |

TABLE 68-continued

Fields in the Medical Condition Results File

| Field Number | Field Descriptive Name | Notes |
|---|---|---|
| 18 | Physician t-score for average episode charges<br>Field name:<br>Prov_TScoreCatChg0 | t-test score result as compared to peer group on relative average episode charges in dollars. |
| 19 | Physician episode charges t-test statistical significance indicator<br>Field name:<br>Prov_TScoreCatChg_sigdiff0 | 1 = result of physician t-test for average episode charges is statistically significant at the selected confidence level.<br>0 = not statistically significant at selected confidence level. |
| colspan="2" Section B - Repeated Physician Fields for Each Service Category (8 fields repeated 11 times) | | |
| 1 | Physician average per episode utilization for the service category<br>Field name:<br>Prov_MBCCatUtl* | Average per episode utilization for the service category (service category 8 contains inpatient days per episode, service category 9 contains inpatient admits per episode). For the "0" row, this field contains the weighted average utilization for the service category. For all other rows, this field contains the average medical condition utilization for the service category. |
| 2 | Physician relative efficiency score based on per episode utilization for the service category<br>Field name:<br>Prov_ScoreCatUtl* | Score as compared to peer group based on relative average per episode utilization for the service category |
| 3 | Physician t-score for the service category utilization<br>Field name:<br>Prov_TScoreCatUtl* | t-test score result as compared to peer group on relative average per episode utilization for the service category |
| 4 | Physician per-episode utilization t-test statistical significance indicator<br>Field name:<br>Prov_TScoreCatUtl_sigdiff* | 1 = result of physician t-test for average utilization for the service category is statistically significant at the selected confidence level.<br>0 = not statistically significant at selected confidence level. |
| 5 | Physician average episode charges for the service category<br>Field name:<br>Prov_MBCCatChg* | Average episode charges in dollars, for the service category. For the "0" row, this field contains the weighted average charges for the service category. For all other rows, this field contains the average medical condition charges for the service category. |
| 6 | Physician relative efficiency score based on episode charges for the service category<br>Field name:<br>Prov_ScoreCatChg* | Score as compared to peer group based on relative average episode charges in dollars, for the service category |
| 7 | Physician t-score for average episode charges for the service category<br>Field name:<br>Prov_TScoreCatChg* | t-test score result as compared to peer group on relative average episode charges in dollars for the service category |
| 8 | Physician episode charges t-test statistical significance indicator for the service category<br>Field name:<br>Prov_TScoreCatChg_sigdiff* | 1 = result of physician t-test for average episode charges for the service category is statistically significant at the selected confidence level.<br>0 = not statistically significant at selected confidence level. |
| colspan="2" Section C - Non-Repeated Peer Group Fields (2 fields) | | |
| 1 | Peer Group average episode duration<br>Field name:<br>Peer_MBCCatUtl0 | Peer Group average episode duration in days. For the "0" row, this field contains the weighted average episode duration in days. For all other rows, this field contains the average medical condition duration in days. |
| 2 | Peer Group average episode charges in dollars<br>Field name:<br>Peer_MBCCatChg0 | Peer Group average episode charges in dollars, across all service categories. For the "0" row, this field contains the weighted overall average episode charges. For all other rows, this field contains the overall average medical condition charges per episode. |
| colspan="2" Section D - Repeated Peer Group Fields for Each Service Category (2 fields repeated 11 times) | | |
| 1 | Peer Group average episode utilization for the service category<br>Field name:<br>Peer_MBCCatUtl* | Peer Group average episode utilization for the service category (service category 8 contains inpatient days per episode, service category 9 contains inpatient admits per episode). For the "0" row, this field contains the weighted average utilization for the service category. For all other rows, this field contains the average medical condition utilization for the service category.. |

TABLE 68-continued

Fields in the Medical Condition Results File

| Field Number | Field Descriptive Name | Notes |
|---|---|---|
| 2 | Peer Group average episode charges in dollars for the service category<br>Field name:<br>Peer_MBCCatChg* | Peer Group average episode charges in dollars for the service category. For the "0" row, this field contains the weighted average charges for the service category. For all other rows, this field contains the average medical condition charges for the service category. |

Step 30: Produce Reports

The open structure of the PROVAN Output Files allows the user to produce many types of physician-level (or physician group-level) reports.

The system of the present invention also produces reports using the PROVAN Output Files that provide the user with physician-level (or physician group-level) information to help understand what underlies the physician's overall efficiency score. These reports are called the Practitioner Efficiency Measurement Reports.

Practitioner Efficiency Measurement Reports provide statistical analysis at the overall weighted average level that identifies physician charges and utilization that are significantly different from peer group results. The Reports may also provide statistical analysis at the medical condition level.

For each of the 31 specialty types with a marketbasket of medical conditions, there is a corresponding Practitioner Efficiency Measurement Report. The Practitioner Efficiency Measurement Reports present the details behind a practitioner's efficiency measurement score.

The Practitioner Efficiency Measurement Report consists of two reports for each of the 31 practitioner specialty types. Report 1 is entitled Average Charges per Episode of Care. This report presents a physician's overall weighted average charges per episode as well as the overall weighted average charge per episode for the peer group. These two charge values form the foundation for the practitioner's efficiency score. Report 2 is entitled Average Utilization per Episode of Care. This report presents a physician's corresponding weighted average utilization patterns per episode as well as the peer group's weighted average utilization patterns per episode.

FIG. 8 presents a detailed description of Report 1, the Average Charges per Episode of Care. Results from a general internist are compared to a peer group of general internists.

The headings at the top of the FIG. 8 report are as follows. The practitioner name is the name of the physician receiving an efficiency score. Specialty type refers to the specialty of the physician receiving an efficiency score. The attached general internist's specialty type is shown as General Internist. The practitioner ID is the unique identification number that is assigned to the physician receiving an efficiency score. The system of the present invention organizes the information output and reports based on aggregate group name. Aggregate group name is the name of the aggregate group relevant to the current report. For example, if a comparison is made on the basis of geographic regions, the aggregate group name might represent a specific region defined by identifying individual zip codes. The quartile is assigned to each physician after each specialty-specific physician in a region receives an efficiency score. The decile is assigned to each physician after each specialty-specific physician in a region receives an efficiency score. The efficiency score for a physician is calculated by dividing the physician's weighted average overall mean charge by the peer group's weighted average overall mean charge. The attached general internist's efficiency score is 1.32, indicating that the internist's treatment pattern efficiency is 32% more resource intensive than the peer group's practice. The significant difference allows the user to observe whether the physician's efficiency score is statistically significantly different from the peer group average. 'Yes' means the physician's efficiency score is significantly different from the peer group's efficiency score. The user may employ two different levels of confidence (0.10 confidence level and 0.25 confidence level). The attached general internist's efficiency score is statistically significantly different than the peer group—indicated by the Yes in this field.

The body of the report headings are as follows. The medical condition name is the condition within a specialty-specific marketbasket. For the general internist marketbasket, this column lists the conditions generally treated by general internists. The peer group weighted average is at the top of the medical condition column. This row presents the peer group's weighted average charge per episode results. For example, the general internist peer group's overall weighted average charges are $205 per episode (see Column 4 of the FIG. 8 report). The practitioner weighted average row is directly under the peer group weighted average row, and entitled "Practitioner Weighted Avg." This row presents each physician's weighted average charge per episode results. For example, the general internist's overall weighted average charges are $269 per episode (see Column 4 of the FIG. 8 report). The star next to the $269 per episode indicates that the weighted average results are statistically significantly different (p<0.25) from the peer group's weighted average results.

The SOI column presents the severity-of-illness (SOI) of the episodes being examined for a medical condition. There are up to three SOI levels for each medical condition, with SOI-1 being the least severe (routine, noncomplicated), and SOI-3 being the most severe. The episode count column presents the number of eligible episodes being examined for the peer group and the physician. For the general internist peer group, there are 46,656 eligible episodes. For the general internist physician, there are 217 eligible episodes. The general internist's 217 eligible episode count is the sum of the condition-specific episodes listed in this column. The Report shows the general internist treated 43 episodes of hypertension, 23 episodes of diabetes with no complications, 3 episodes of diabetes with circulatory involvement, 26 episodes of disorders of lipid metabolism, etc.).

The average charge per episode column presents the overall weighted average charge per episode results for the specialty-specific peer group. For example, the general internist peer group's overall weighted average charges are $205 per episode (see Column 4 of the FIG. 8 report). Directly under the peer group weighted average row is the physician's weighted average charge per episode. For the general internist, the overall weighted average charges are $269 per episode. The star next to the physician's $269 per episode indicates that the overall weighted average results are statistically significantly different (p<0.25) from the peer group's weighted average results.

The average charge per episode column is followed by service categories related to charges. The sum of these service category columns equals the overall average charge per episode. The service category report headings are as follows. There are five professional outpatient and ambulatory services columns that present professional outpatient and ambulatory charges. The services are physician-related and are not facility-billed services. The first column is professional visits (prof visits). This column presents the average charges per episode for professional visits incurred in the physician office, clinic, or outpatient department of a hospital. The second column is diagnostic tests (diag tests). This column presents the average charges per episode for diagnostic tests incurred in the physician office, clinic, outpatient department of a hospital, or surgicenter. Diagnostic tests represent imaging tests (X-rays, CAT scans, MRIs, etc.), functional tests (EKGs, echocardiograms, etc.), and invasive tests. The third column is laboratory and pathology (lab/path). This column presents the average charges per episode for laboratory and pathology services incurred in the physician office, clinic, outpatient department of a hospital, or surgicenter. The fourth column is medical and surgical procedures (med/surg). This column presents the average charges per episode for medical and surgical procedures incurred in the physician office, clinic, outpatient department of a hospital, or surgicenter. The fifth column is prescription drugs (Rx). This column presents the average charges per episode for outpatient and ambulatory prescription drugs.

There is one professional inpatient services column. This service-related column presents professional inpatient services. These services are physician related, and not facility billed services. This column presents the average charges per episode for all inpatient professional services.

There is one outpatient facility column and one inpatient facility column. These service-related columns present facility services. These services are facility-related and are not professional-billed services. The facility outpatient services (outpt facility) column presents the average charges per episode for all outpatient facility services incurred in an outpatient department of a hospital or surgicenter. The facility inpatient admissions (hosp inpt admits) column presents the average charges per episode for all hospital inpatient facility services.

There is one alternative care site services column. This service-related column presents facility services incurred in skilled nursing facilities and halfway homes. These services are facility-related and are not professional-billed services. This column presents the average charges per episode for skilled nursing facility and halfway home services.

There is one other medical services column. This service-related column presents other professional medical services. These services are physician-related and are not facility-billed services. The other medical services (other med) column presents the average charges per episode for other medical services incurred in the physician office, clinic, outpatient department of a hospital, and dialysis center. Other medical services include physical therapy, chiropractic services (other than professional visits), chemotherapy and radiation, dental, durable medical equipment, and ambulance services.

FIG. 9 presents a detailed description of Report 2, the Average Utilization per Episode of Care. Results are observed from an actual general internist as compared to a peer group of general internists.

The headings at the top of the FIG. 9 report are the same as for Report 1, Average Charges per Episode (refer to FIG. 8).

The body of the report headings are as follows. The medical condition name is the condition within a specialty-specific marketbasket. For the general internist marketbasket, this column lists the conditions generally treated by general internists. The peer group weighted average is at the top of the medical condition column. This row presents the peer group's weighted average utilization per episode results. The service categories present the peer group's corresponding average utilization per episode to the Report 1 defined average charges per episode. The practitioner weighted average row is directly under the peer group weighted average row is a row entitled Practitioner Weighted Average. This row presents each physician's weighted average utilization per episode results. The service category columns present the physician's corresponding average utilization per episode to the Report 1 defined average charges per episode. The star next to a physician's average utilization per episode result indicates that weighted average results are statistically significantly different (p<0.25) from the peer group's weighted average results.

The SOI column presents the severity-of-illness (SOI) of the episodes being examined for a medical condition. There are up to three SOI levels for each medical condition, with SOI-1 being the least severe (routine, noncomplicated), and SOI-3 being the most severe. The episode count column presents the number of eligible episodes being examined for the peer group and the physician. For the general internist peer group, there are 46,656 eligible episodes; and for the general internist physician, there are 217 eligible episodes.

The average episode duration (days) column presents the weighted average episode duration per episode results for the specialty-specific peer group. For example, the general internist peer group's weighted average duration is 122.8 days per episode (see Column 4). Directly under the peer group weighted average row is the physician's weighted average duration per episode. For the general internist physician, the overall weighted average duration is 123.6 days per episode. There is no star next to the physician's 123.6 days per episode. This indicates that the weighted average duration results are not statistically significantly different (p<0.25) from the peer group's weighted average duration results. Column 4 also presents the average duration per episode for each medical condition treated by the general internist physician. For instance, the general internist treated SOI-1 hypertension for an average 180.0 days per episode, SOI-1 low back pain for 29.4 days per episode, and acute bronchitis for 1.2 days per episode.

The average episode duration column is followed by 11 service categories related to utilization. The service category report headings are as follows. There are five professional outpatient and ambulatory services columns that present the physician's corresponding average utilization per episode to the Report 1 defined average charges per episode. The services are physician related, and not facility billed services. The first column is professional visits (prof visits). This column presents the average number of visits per episode for professional visits incurred in the physician office, clinic, or outpatient department of a hospital. The numerator unit is visits. The second column is diagnostic tests (diag tests). This column presents the average number of diagnostic tests per episode for diagnostic tests incurred in the physician office, clinic, outpatient department of a hospital, or surgicenter. The numerator unit is services or tests. The third column is laboratory and pathology (lab/path). This column presents the average number of lab/path services per episode for laboratory and pathology services incurred in the physician office, clinic, outpatient department of a hospital, or surgicenter. The numerator unit is services. The fourth column is medical and surgical procedures (med/surg). This column presents the average number of med/surg procedures per episode for medical and surgical procedures incurred in the physician office, clinic, outpatient department of a hospital, or surgicenter. The numerator unit is services or procedures. The fifth column is prescription drugs (Rx). This column presents the average number of prescription drug fills per episode for outpatient and ambulatory prescription drugs. The numerator unit is prescription drug fills.

There is one professional inpatient services column. This service-related column presents professional inpatient services. This column presents the physician's corresponding average inpatient professional services to the Report 1 defined average charges per episode. These services are physician related, and not facility billed services. Professional inpatient services (prof inpt): This column presents the average professional services per episode for all inpatient professional services. The numerator unit is services.

There are three facility services columns (one outpatient facility and two inpatient facility). These service-related columns present the facility services. The columns present the facility's corresponding average utilization per episode to the Report 1 defined average charges per episode. These services are facility related, and not professional billed services. The facility outpatient visits (outpt facility) column presents the average visits per episode for all outpatient facility services incurred in an outpatient department of a hospital or surgicenter. The numerator unit is visits. The facility inpatient admissions (hosp inpt admits) column presents the average number of admissions per episode for all hospital inpatient facility services. The numerator unit is admissions. The facility inpatient days (hosp inpt days) column presents the average number of inpatient days per episode for all hospital inpatient facility services. The numerator unit is hospital inpatient days.

There is one alternative care site services column. This service-related column presents facility services incurred in skilled nursing facilities and halfway homes. This column presents the facility's corresponding average services per episode to the Report 1 defined average charges per episode. These services are facility related, and not professional billed services. The alternative sites (altern sites) column presents the average services per episode for all skilled nursing facility and halfway home services. The numerator unit is services.

There is one other medical services column. This service-related column presents other professional medical services. This column presents the physician's corresponding average services per episode to the Report 1 defined average charges per episode. These services are physician related, and not facility billed services. The numerator unit is services.

While various embodiments for physician efficiency measurement and patient health risk stratification has been described and illustrated in detail, it is to be understood that various modifications can be made to embodiments of the present invention without departing from the spirit thereof.

What is claimed is:

1. A healthcare analytics computer system for determining a health care provider efficiency score from a plurality of patient treatment information records, said healthcare analytics computer system comprising a memory device for storing data and a processor in communication with said memory device, said processor programmed to:

store, in said memory device, a mapping table that associates each of a plurality of predefined medical conditions with at least one of a plurality of diagnosis codes, and a specialty table that associates each of a plurality of predefined practice areas with a respective subset of the predefined medical conditions, wherein for each subset, each predefined medical condition is associated with a weight factor indicative of a predetermined relevance of that predefined medical condition to the corresponding predefined practice area;

receive the plurality of patient treatment information records, wherein each of the plurality of patient treatment information records includes a patient identifier associated with one of a plurality of patients, a health care provider identifier associated with one of a plurality of health care providers, at least one of the diagnosis codes, at least one of a plurality of service codes, a service charge, and a service date, wherein each at least one service code is associated with a service rendered to the patient by the one of the plurality of health care providers;

derive a plurality of episode of care records from the plurality of patient treatment information records, wherein each episode of care record links the patient treatment information records associated with a particular episode of one of the predefined medical conditions for one of the patients, wherein the particular episode is identified from the plurality of patient treatment information records by:

grouping, for each patient identifier, the patient treatment information records by predefined medical condition based on the diagnosis codes in the patient treatment information records and the mapping table; and applying predefined window periods to each of the groupings to identify start and end dates for the particular episode of the predefined medical condition;

assign each of the episode of care records to at least one of the plurality of health care providers, wherein each of the plurality of healthcare providers is associated in said memory device with one of the plurality of predefined practice areas;

calculate, for each health care provider in a selected one of the practice areas, a provider average charge per episode for each predefined medical condition in the subset corresponding to the selected practice area, based on the service charges in the patient treatment information records associated with each episode of care record associated with the predefined medical condition and assigned to the health care provider;

calculate, for a peer group of the health care providers in the selected practice area, a peer group average charge per episode for each predefined medical condition in the corresponding subset, based on the service charges in the patient treatment information records associated with each episode of care record associated with the predefined medical condition and assigned to one of the health care providers in the peer group;

calculate a relevance-weighted overall provider charge per episode by:

modifying the provider average charge per episode for each predefined medical condition in the corresponding subset by applying the respective weight factor associated with the predefined medical condition; and combining the modified provider average charge per episode for the predefined medical conditions to obtain the relevance-weighted overall provider charge per episode;

calculate a relevance-weighted overall peer group charge per episode by:

modifying the peer group average charge per episode for each predefined medical condition in the corresponding subset by applying the respective weight factor associated with the predefined medical condition; and combining the modified peer group average charge per episode for the predefined medical conditions to obtain the relevance-weighted overall peer group charge per episode;

determine the efficiency score for each health care provider in the selected one of the practice areas by comparing the relevance-weighted overall provider charge per episode to the relevance-weighted overall peer group charge per episode; and report the efficiency scores for each health care provider in the selected one of the practice areas.

2. The healthcare analytics computer system of claim 1, wherein said processor is further programmed to store, in said memory device, a value for each of the predefined window periods, wherein the value varies among the predefined medical conditions.

3. The healthcare analytics computer system of claim 1, wherein said processor is programmed to:

store, in said memory device, a trigger association between (i) at least one of the plurality of service codes corresponding to at least one of the preselected medical conditions, and (ii) one of a plurality of stages of the at least one preselected medical condition;

assign the particular episode of the at least one preselected medical condition to at least one of the plurality of stages of the at least one preselected medical condition by comparing the service codes in the corresponding patient treatment information records to the trigger association; and treat each of the plurality of stages of the at least one preselected medical condition as separate medical conditions for purposes of calculating the provider average charge per episode, the peer group average charge per episode, the relevance-weighted overall provider charge per episode, and the relevance-weighted overall peer group charge per episode.

4. The healthcare analytics computer system of claim 1, wherein said processor is programmed to assign a severity-of-illness classification to each of the episode of care records based on the diagnosis codes in the patient treatment information records associated with the particular episode.

5. The healthcare analytics computer system of claim 4, wherein said processor is programmed to assign the severity-of-illness classification based on a count of a subset of the diagnosis codes associated with the particular episode, wherein the subset of diagnosis codes is predefined as indicating a relatively more severe instance of the associated predefined medical condition.

6. The healthcare analytics computer system of claim 4, wherein said processor is programmed to calculate the provider average charge per episode and the peer group average charge per episode for each predefined medical condition in the subset corresponding to the selected practice area at each severity of illness classification associated with the predefined medical condition.

7. The healthcare analytics computer system of claim 1, wherein said processor is programmed to:

report, for each health care provider, the relevance-weighted overall provider charge per episode for each predefined medical condition in the corresponding subset; and identify in the report whether the relevance-weighted overall provider charge per episode is statistically significantly different from the relevance-weighted overall peer group charge per episode.

8. A computer-implemented method for determining a health care provider efficiency score from a plurality of patient treatment information records implemented on a healthcare analytics computer system, the healthcare analytics computer system comprising a memory device for storing data and a processor in communication with the memory device, said method comprising:

storing, in the memory device, a mapping table that associates each of a plurality of predefined medical conditions with at least one of a plurality of diagnosis codes, and a specialty table that associates each of a plurality of predefined practice areas with a respective subset of the predefined medical conditions, wherein for each subset, each predefined medical condition is associated with a weight factor indicative of a predetermined relevance of that predefined medical condition to the corresponding predefined practice area;

receiving the plurality of patient treatment information records, wherein each of the plurality of patient treatment information records includes a patient identifier associated with one of a plurality of patients, a health care provider identifier associated with one of a plurality of health care providers, at least one of the diagnosis codes, at least one of a plurality of service codes, a service charge, and a service date, wherein each at least one service code is associated with a service rendered to the patient by the one of the plurality of health care providers;

deriving a plurality of episode of care records from the plurality of patient treatment information records, wherein each episode of care record links the patient treatment information records associated with a particular episode of one of the predefined medical conditions for one of the patients, wherein the particular episode is identified from the plurality of patient treatment information records by:

grouping, for each patient identifier, the patient treatment information records by predefined medical condition based on the diagnosis codes in the patient treatment information records and the mapping table; and applying predefined window periods to each of the groupings to identify start and end dates for the particular episode of the predefined medical condition;

assigning each of the episode of care records to at least one of the plurality of health care providers, wherein each of the plurality of healthcare providers is associated in the memory device with one of the plurality of predefined practice areas;

calculating, for each health care provider in a selected one of the practice areas, a provider average charge per episode for each predefined medical condition in the subset corresponding to the selected practice area, based on the service charges in the patient treatment information records associated with each episode of care record associated with the predefined medical condition and assigned to the health care provider;

calculating, for a peer group of the health care providers in the selected practice area, a peer group average charge per episode for each predefined medical condition in the corresponding subset, based on the service charges in the patient treatment information records associated with each episode of care record associated with the predefined medical condition and assigned to one of the health care providers in the peer group;

calculating a relevance-weighted overall provider charge per episode by:

modifying the provider average charge per episode for each predefined medical condition in the corresponding subset by applying the respective weight factor associated with the predefined medical condition; and combining the modified provider average charge per episode for the predefined medical conditions to obtain the relevance-weighted overall provider charge per episode;

calculating a relevance-weighted overall peer group charge per episode by:

modifying the peer group average charge per episode for each predefined medical condition in the corresponding subset by applying the respective weight factor associated with the predefined medical condition; and combining the modified peer group average charge per episode for the predefined medical conditions to obtain the relevance-weighted overall peer group charge per episode;

determining the efficiency score for each health care provider in the selected one of the practice areas by comparing the relevance-weighted overall provider charge per episode to the relevance-weighted overall peer group charge per episode; and reporting the efficiency scores for each health care provider in the selected one of the practice areas.

9. The computer-implemented method of claim 8, further comprising storing, in the memory device, a value for each of the predefined window periods, wherein the value varies among the predefined medical conditions.

10. The computer-implemented method of claim 8, further comprising:

storing, in the memory device, a trigger association between (i) at least one of the plurality of service codes corresponding to at least one of the preselected medical conditions, and (ii) one of a plurality of stages of the at least one preselected medical condition;

assigning the particular episode of the at least one preselected medical condition to at least one of the plurality of stages of the at least one preselected medical condition by comparing the service codes in the corresponding patient treatment information records to the trigger association; and treating each of the plurality of stages of the at least one preselected medical condition as separate medical conditions for purposes of calculating the provider average charge per episode, the peer group average charge per episode, the relevance-weighted overall provider charge per episode, and the relevance-weighted overall peer group charge per episode.

11. The computer-implemented method of claim 8 further comprising assigning a severity-of-illness classification to each of the episode of care records based on the diagnosis codes in the patient treatment information records associated with the particular episode.

12. The computer-implemented method of claim 11, further comprising assigning the severity-of-illness classification based on a count of a subset of the diagnosis codes associated with the particular episode, wherein the subset of diagnosis codes is predefined as indicating a relatively more severe instance of the associated predefined medical condition.

13. The computer-implemented method of claim 11, further comprising calculating the provider average charge per episode and the peer group average charge per episode for each predefined medical condition in the subset corresponding to the selected practice area at each severity of illness classification associated with the predefined medical condition.

14. The computer-implemented method of claim 8, further comprising:

reporting, for each health care provider, the relevance-weighted overall provider charge per episode for each predefined medical condition in the corresponding subset; and identifying in the report whether the relevance-weighted overall provider charge per episode is statistically significantly different from the relevance-weighted overall peer group charge per episode.

15. A computer-readable storage device, having processor-executable instructions embodied thereon for determining a health care provider efficiency score from a plurality of patient treatment information records using a healthcare analytics computer system, wherein the healthcare analytics computer system includes at least one processor and a memory device coupled to the processor, wherein, when executed by the healthcare analytics computer system, the processor-executable instructions cause the healthcare analytics computer system to:

store, in the memory device, a mapping table that associates each of a plurality of predefined medical conditions with at least one of a plurality of diagnosis codes, and a specialty table that associates each of a plurality of predefined practice areas with a respective subset of the predefined medical conditions, wherein for each subset, each predefined medical condition is associated with a weight factor indicative of a predetermined relevance of that predefined medical condition to the corresponding predefined practice area;

receive the plurality of patient treatment information records, wherein each of the plurality of patient treatment information records includes a patient identifier associated with one of a plurality of patients, a health care provider identifier associated with one of a plurality of health care providers, at least one of the diagnosis codes, at least one of a plurality of service codes, a service charge, and a service date, wherein each at least one service code is associated with a service rendered to the patient by the one of the plurality of health care providers;

derive a plurality of episode of care records from the plurality of patient treatment information records, wherein each episode of care record links the patient treatment information records associated with a particular episode of one of the predefined medical conditions for one of the patients, wherein the particular episode is identified from the plurality of patient treatment information records by:

grouping, for each patient identifier, the patient treatment information records by predefined medical condition based on the diagnosis codes in the patient treatment information records and the mapping table; and applying predefined window periods to each of the groupings to identify start and end dates for the particular episode of the predefined medical condition;

assign each of the episode of care records to at least one of the plurality of health care providers, wherein each of the plurality of healthcare providers is associated in the memory device with one of the plurality of predefined practice areas;

calculate, for each health care provider in a selected one of the practice areas, a provider average charge per episode for each predefined medical condition in the subset corresponding to the selected practice area, based on the service charges in the patient treatment information records associated with each episode of care record associated with the predefined medical condition and assigned to the health care provider;

calculate, for a peer group of the health care providers in the selected practice area, a peer group average charge per episode for each predefined medical condition in the corresponding subset, based on the service charges in the patient treatment information records associated with each episode of care record associated with the predefined medical condition and assigned to one of the health care providers in the peer group;

calculate a relevance-weighted overall provider charge per episode by:

modifying the provider average charge per episode for each predefined medical condition in the corresponding subset by applying the respective weight factor associated with the predefined medical condition; and combining the modified provider average charge per episode for the predefined medical conditions to obtain the relevance-weighted overall provider charge per episode;

calculate a relevance-weighted overall peer group charge per episode by:

modifying the peer group average charge per episode for each predefined medical condition in the corresponding subset by applying the respective weight factor associated with the predefined medical condition; and combining the modified peer group average charge per episode for the predefined medical conditions to obtain the relevance-weighted overall peer group charge per episode;

determine the efficiency score for each health care provider in the selected one of the practice areas by comparing the relevance-weighted overall provider charge per episode to the relevance-weighted overall peer group charge per episode; and report the efficiency scores for each health care provider in the selected one of the practice areas.

16. The computer-readable storage device of claim 15, wherein the processor-executable instructions cause the healthcare analytics computer system to store, in the memory device, a value for each of the predefined window periods, wherein the value varies among the predefined medical conditions.

17. The computer-readable storage device of claim 15, wherein the processor-executable instructions cause the healthcare analytics computer system to:

store, in the memory device, a trigger association between (i) at least one of the plurality of service codes corresponding to at least one of the preselected medical conditions, and (ii) one of a plurality of stages of the at least one preselected medical condition;

assign the particular episode of the at least one preselected medical condition to at least one of the plurality of stages of the at least one preselected medical condition by comparing the service codes in the corresponding patient treatment information records to the trigger association; and treat each of the plurality of stages of the at least one preselected medical condition as separate medical conditions for purposes of calculating the provider average charge per episode, the peer group average charge per episode, the relevance-weighted overall provider charge per episode, and the relevance-weighted overall peer group charge per episode.

18. The computer-readable storage device of claim 15, wherein the processor-executable instructions cause the healthcare analytics computer system to assign a severity-of-illness classification to each of the episode of care records based on the diagnosis codes in the patient treatment information records associated with the particular episode.

19. The computer-readable storage device of claim 18, wherein the processor-executable instructions cause the healthcare analytics computer system to assign the severity-of-illness classification based on a count of a subset of the diagnosis codes associated with the particular episode, wherein the subset of diagnosis codes is predefined as indicating a relatively more severe instance of the associated predefined medical condition.

20. The computer-readable storage device of claim 18, wherein the processor-executable instructions cause the healthcare analytics computer system to calculate the provider average charge per episode and the peer group average charge per episode for each predefined medical condition in the subset corresponding to the selected practice area at each severity of illness classification associated with the predefined medical condition.

21. The computer-readable storage device of claim 15, wherein the processor-executable instructions cause the healthcare analytics computer system to:

report, for each health care provider, the relevance-weighted overall provider charge per episode for each predefined medical condition in the corresponding subset; and identify in the report whether the relevance-weighted overall provider charge per episode is statistically significantly different from the relevance-weighted overall peer group charge per episode.

* * * * *